(12) United States Patent
Slassi et al.

(10) Patent No.: US 9,441,012 B2
(45) Date of Patent: Sep. 13, 2016

(54) FLUORINATED EPOXYKETONE-BASED COMPOUNDS AND USES THEREOF AS PROTEASOME INHIBITORS

(71) Applicant: FLUORINOV PHARMA INC., Toronto (CA)

(72) Inventors: Abdelmalik Slassi, Mississauga (CA); Peter Dove, Burlington (CA)

(73) Assignee: Trillium Therapeutics Inc., Mississauga, Ontario (CA)

( * ) Notice: Subject to any disclaimer, the term of this patent is extended or adjusted under 35 U.S.C. 154(b) by 0 days.

(21) Appl. No.: 14/420,817

(22) PCT Filed: Aug. 13, 2013

(86) PCT No.: PCT/CA2013/050620
§ 371 (c)(1),
(2) Date: Feb. 10, 2015

(87) PCT Pub. No.: WO2014/026282
PCT Pub. Date: Feb. 20, 2014

(65) Prior Publication Data
US 2015/0203534 A1    Jul. 23, 2015

Related U.S. Application Data

(60) Provisional application No. 61/682,836, filed on Aug. 14, 2012.

(51) Int. Cl.
*A61K 38/06*    (2006.01)
*C07K 5/08*    (2006.01)
*C07K 5/06*    (2006.01)
*C07K 5/062*    (2006.01)
*C07K 5/065*    (2006.01)
*A61K 38/00*    (2006.01)

(52) U.S. Cl.
CPC ............ *C07K 5/0827* (2013.01); *A61K 38/06* (2013.01); *C07K 5/06008* (2013.01); *C07K 5/06043* (2013.01); *C07K 5/06078* (2013.01); *A61K 38/00* (2013.01)

(58) Field of Classification Search
None
See application file for complete search history.

(56) References Cited

U.S. PATENT DOCUMENTS

2007/0293465 A1    12/2007   Shenk et al.
2015/0218212 A1*    8/2015   Slassi .................. C07K 5/1027
                                              514/20.1

FOREIGN PATENT DOCUMENTS

WO    2005111008 A2    11/2005
WO    2007056464 A1     5/2007
WO    2011136905 A2    11/2011

OTHER PUBLICATIONS

Spaltenstein, Andrew et al, "Design and synthesis of novel protease inhibitors. Tripeptide alpha', beta'-epoxyketones as nanomolar inactivators of the proteasome." Tett. Lett. (1996) 37(9) p. 1343-1346.*

Shang, Fu and Taylor, Allen; "Roles for the ubitquitin-proteasome pathway in protein quality control and signaling in the retina: implications in the pathogenesis of age related macular degeneration." Mol. Aspects Med. (2012) 33(4) p. 446-466.*

Zhou, Han Jie et al, "Design and synthesis of an orally bioavailable and selective peptide epoxyketone proeasome inhibitor (pr-047)." J. Med. Chem. (2009) 52 p. 3028-3038.*

Groll, Michael et al, "Crystal structure of epoxomincin 20s proeasome reveals a molecular basis for selectivity of alpha', beta'-epoxyketone proteasome inhbitors." J. Am. Chem. Soc. (2000) 122 p. 1237-1238.*

Sunohara, Kazuhiro et al, "Discovery of n-(2,3,5-triazoyl)mycophenolic amide and mycophenolic epoxyketone as novel inhibitors of human impdh." Bioorg. Med. Chem. Lett. (2013) 23 p. 5140-5144.*

Roush, William R. et al, "Design and synthesis of dipeptidyl alpha', beta'-epoxyketones, potent irreversible inhibitors of the cysteine protease cruzain." Bioorg. Med. Chem. Lett. (1998) 8 p. 2809-2812.*

De Schepper, Stefanie et al, "Inhibition of histone deacetylases by chamydocin induces apoptosis and proteasome-mediated degradation of survivin." J. Pharmacol. Exper. Therapeut. (2003) 304(2) p. 881-888.*

The thermo fisher web page for sulfhydryl reactive crosslinker chemistry, https://www.thermofisher.com/us/en/home/life-science/protein-biology/protein-biology-learning-center/protein-biology-resource-library/pierce-protein-methods/sulfhydryl-reactive-crosslinker-chemistry.html, downloaded Nov. 18, 2015.*

(Continued)

*Primary Examiner* — Maury Audet
*Assistant Examiner* — Fred Reynolds
(74) *Attorney, Agent, or Firm* — Bereskin & Parr LLP/S.E.N.C.R.L., s.r.l.; Patricia Folkins

(57) ABSTRACT

The present application relates to novel fluorinated epoxyketone-based compounds, compositions comprising these compounds and their use, in particular for the treatment of diseases, disorders or conditions mediated by proteasome inhibition, in particular, the present application includes compounds of Formula I, and compositions and uses thereof.

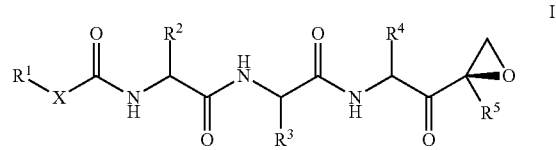

30 Claims, 4 Drawing Sheets

(56) References Cited

OTHER PUBLICATIONS

Lecker, Stewart H. et al, "Muscle protein breakdown and the critical role of the ubiquitin-proteasome pathway in normnal and disease states." J. Nutr. (1999) 129 p. 227S-237S.*

Crawford, Lisa J. et al, "P{Roteasome inhibitors in cancer therapy." J. Cell Commun. Signal. (2011) 5 p. 101-110.*

International Search Report for PCT/CA2013/050620 dated Feb. 17, 2015.

European Extended Search Report for corresponding European Patent Application No. 13829194.3 dated Jan. 12, 2016.

Dharminder, Chauhan, et al., "A novel orally active proteasome inhibitor ONX 0912 triggers in vitro and in vivo cytotoxicity in multiple myeloma", Blood, Vo. 116, No. 23, Dec. 2, 2010, pp. 4906-4915.

* cited by examiner

A

B

A

B

A

B

US 9,441,012 B2

FLUORINATED EPOXYKETONE-BASED COMPOUNDS AND USES THEREOF AS PROTEASOME INHIBITORS

CROSS-REFERENCE TO RELATED APPLICATIONS

This application is a National Stage of co-pending International Application No. PCT/CA2013/050620 filed Aug. 13, 2013 which claims the benefit of priority from U.S. Provisional Patent Application Ser. No. 61/682,836 filed on Aug. 14, 2012, the contents of both of which are incorporated herein by reference in their entirety.

FIELD

The present application relates to novel fluorinated epoxyketone-based compounds, to processes for their preparation, to compositions comprising them, and to their use in therapy. More particularly, it relates to compounds useful in the treatment of diseases, disorders or conditions mediated by or associated with proteasome inhibition.

BACKGROUND

The multi-catalytic proteasome is the ubiquitous proteinase found in cells throughout the plant and animal kingdoms that is responsible for the ubiquitin-dependent degradation of intracellular proteins. Thousands of copies are found in all cells, in both the cytoplasm and the nucleus, which constitute up to 3% of all cellular protein content. Proteasomes serve multiple intracellular functions, including the degradation of damaged proteins and the modulation of many regulatory proteins that affect inflammatory processes, viral shedding, the cell cycle, growth, and differentiation, to name but a few [*Cell* 1994, 79, 13-21; *Nat. Rev. Mol. Cell Biol.* 2005, 6, 79-87; *Semin. Oncol.* 2004, 31, 3-9; *Chem. Biol.* 2001, 8, 739-758].

The ubiquitin-proteasome pathway (UPP), also known as the ubiquitin-proteasome system (UPS), regulates the degradation of intracellular proteins with specificity as to target, time and space. The pathway plays a central role in recognizing and degrading misfolded and abnormal proteins in most mammalian cells [*Nature* 2000, 404, 770-774]. Such a process is very important in maintaining the biological homeostasis and regulation of different cellular processes such as but not limited to cell differentiation, cell cycle control, antigen processing and hormone metabolism [*EMBO J.* 1998, 17, 7151-7160; *Chem. Biol.* 2001, 8, 739-758]. In this pathway, the 26S proteasome is the main proteolytic component, which is found in all eukaryotic cells and is made up of the cylinder-shaped multi-catalytic proteinase complex (MPC) 20S proteasome and two regulatory particle (RP) 19S proteasomes. The 19S proteasome located at each end of the 20S proteasome is made up of 18 subunits, and controls the recognition, unfolding, and translocation of protein substrates into the lumen of the 20S proteasome [*Annu. Rev. Biochem.* 1999, 68, 1015-1068].

X-ray crystallography of the 26S proteasome revealed that the 20S proteasome is composed of 28 protein subunits arranged in four stack rings, with each ring made up of seven α- and β-type subunits, following an α1-7β1-7 stoichiometry [*Science* 1995, 268, 533-539; *Nature* (London) 1997, 386, 463-467]. The two outer chambers are formed by α subunits, while the central chamber, containing the proteolytic active sites, is made up of β subunits. Three of the 14 β subunits are responsible for the post-glutamyl peptide hydrolysis activity (PGPH, attributed to (β1), trypsin-like activity (T-L, (β2), and chymotripsin-like activity (CT-L, β5), respectively, and all these three active subunits hydrolyze the amide bond of protein substrates with the hydrophilic γ-hydroxyl group of the N-terminal threonine (Oγ-Thr1).

Rising interest in the mechanism and function of the proteasomes and the ubiquitin system revealed that it is hard to find any aspect of the cellular metabolic network that is not directly or indirectly affected by the degradation system. This includes, for example the cell cycle, the "quality control" of newly synthesized proteins (ERAD: Endoplasmic Reticulum Associated Protein Degradation), transcription factor regulation, gene expression, cell differentiation and immune response as well as pathologic processes such as cancer, neurodegenerative diseases, lipofuscin formation, diabetes, atherosclerosis, inflammatory processes and cataract formation in addition to the aging process and the degradation of oxidized proteins in order to maintain cell homeostasis. But this seems to be only a small aspect of the general view. The various regulator proteins that are able to change the rate or specificity of proteolysis, fitting it out for highly specialized tasks, or the precise regulation of the half-life of cellular proteins by ubiquitin-mediated degradation shape the proteasome and the ubiquitin-proteasome system into a useful part of cellular function in the three kingdoms of bacteria, plants and animals.

Cancer is a leading cause of death worldwide. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is a method that is useful in treating patients with metastatic cancers or diffuse cancers such as leukemias. However, although chemotherapy can provide a therapeutic benefit, it often fails to result in cure of the disease due to the patient's cancer cells becoming resistant to the chemotherapeutic agent. Therefore, a need exists for additional chemotherapeutics to treat cancer.

The concept of proteasome inhibition as a therapeutic approach in cancer is known. The first-in-class inhibitor bortezomib is a potent, selective, and reversible proteasome inhibitor which targets the 26S proteasome complex and inhibits its function. Proteasomal degradation of misfolded or damaged proteins proceeds by recognition of poly-ubiquitinated proteins by the 19S regulatory subunit of the 26S protease, and subsequent hydrolysis to small polypeptides.

The successful development of bortezomib for treatment of relapsed/refractory multiple myeloma (MM) and mantle cell lymphoma, has shown proteasome inhibition to be a useful therapeutic strategy [*Nat. Rev. Cancer* 2004, 4, 349-360; *Bioorg. Med. Chem. Lett.* 1998, 8, 333-338; *J. Clin. Oncol.* 2002, 20, 4420-4427; *N. Engl. J. Med.* 2003, 348, 2609-2617; *N. Engl. J. Med.* 2005, 352, 2487-2498; *J. Clin. Oncol.* 2007, 25, 3892-3901]. Bortezomib primarily inhibits chymotryptic, without altering tryptic or caspase-like, proteasome activity. Bortezomib has pleiotropic effects on multiple myeloma biology by targeting a) cell-cycle regulatory proteins; b) the unfolded protein response (UPR) pathway via modulating the transcriptional activity of plasma cell differentiation factor X-box binding protein-I (XBP-I); c) p53-mediated apoptosis/MDM2; d) DNA repair mechanisms; and e) classical stress-response pathways via both intrinsic (caspase-9 mediated) and extrinsic (caspase-3 mediated) cell death cascades. Specifically, bortezomib activates c-Jun N-terminal kinase (JNK), which triggers mitochondrial apoptotic signalling: release of cytochrome-c (cyto-c) and second mitochondrial activator of caspases (Smac) from mitochondria to cytosol, followed by activation of caspase-9 and caspase-3.

Although bortezomib has shown clinical success, a significant fraction of patients relapse or are refractory to treatment [*J. Clin. Oncol.* 2005, 23, 676-684; *J. Clin. Oncol.* 2005, 23, 667-675]. Additionally, dose-limiting toxicities (DLT), including a painful peripheral neuropathy and thrombocytopenia, have been reported [*J. Clin. Oncol.* 2006, 24, 3113-3120; *Blood* 2005, 106, 3777-3784]. To date, it is unclear whether these toxicities can be attributed to off-target effects because bortezomib inhibits other enzymes such as serine proteases.

A recently reported structural analogue of the microbial natural product epoxomicin, known as carfilzomib (also called PR-171) was initially identified for its antitumor activity and subsequently shown to be a potent inhibitor of the proteasome [*Cancer Res.* 2007, 67, 6383-6391; *Curr. Opin. Drug Discovery* 2008, 11, 616-625; *J. Am. Chem. Soc.* 2000, 122, 1237-1238; *J. Antibiot.* (Tokyo) 1992, 45, 1746-1752; *Bioorg. Med. Chem. Lett.* 1999, 9, 2283-2288; *Cancer Res.* 1999, 59, 2798-2801; *Proc. Natl. Acad. Sci.* U.S.A. 1999, 96, 10403-10408]. Carfilzomib selectively inhibits the CT-L activity of the 20S proteasome with minimal cross reactivity to other protease classes.

Preclinical studies and phase I clinical studies demonstrated that consecutive daily dosing schedules with carfilzomib are both well-tolerated and promote antitumor activity in hematologic malignancies, including patients previously treated with bortezomib [*Blood* 2007, 110, 3281-3290; *Br. J. Hamaetol.* 2007, 136, 814-828; *Blood* 2007, 110, 409; *Blood* 2007, 110, 411]. Carfilzomib is currently being evaluated in phase I and phase II clinical trials in multiple myeloma, non-Hodgkin's lymphoma, and solid tumors.

Clinical responses to known proteasome inhibitor therapies require frequent dosing (e.g., twice per week) and prolonged treatment. For example, both bortezomib and carfilzomib are administered intravenously (iv) on biweekly or more frequent dosing schedules with a treatment that can extend for over 6 months. Therefore, the development of orally bioavailable proteasome inhibitors that would allow for dosing flexibility and improve patient convenience is desirable.

Proteasome inhibitor-based therapeutics are useful in other diseases beyond clinical oncology. In addition to its role in cancer therapy, the proteasome is linked to the production of the majority of the class I antigens [*Nature* 1992, 357, 375-379]. Therefore excessive inhibition of the proteasome might increase the chance of viral infections. For example, it was reported that replication of the HIV-1 virus could be limited by the degradative actions of the proteasome and that the proteasome inhibitor, MG-132 or lactacystin, enhanced the ability of the virus to replicate [*J. Virol.* 1998, 72, 3845-3850]. In contrast, a number of recent publications have suggested that the ubiquitin-proteasome pathway has a useful role in the processing of retroviral assembly, maturation, and budding [*Proc. Natl. Acad. Soc.* USA 2000, 97, 13069-13074; *Proc. Natl. Acad. Sci.* USA 2000, 97, 13057-13062; *Proc. Natl. Acad. Sci.* USA 2000, 97, 13063-13068]. Proteasome inhibition also interferes with gag polyprotein processing, release, and maturation of HIV-1 and HIV-2, and ubiquitination is required for retroviral release. Hence, proteasome inhibitors can be useful for the treatment of HIV and other viral infections.

Proteasome inhibition also has clinical potential for treatment of inflammatory and autoimmune diseases through multiple pathways, including MHC-mediated antigen presentation, cytokine and cell cycle regulation, and apoptosis [*J. Rheumatol.* 2005, 32, 1192-119]. In inflammatory arthritis, it was shown that NF-κB regulates multiple critical cytokines involved in the pathogenesis of rheumatoid arthritis (RA) [*Arthritis Rheum.* 2004, 50, 2381-2386; *Arthritis Rheum.* 2004, 50, 3541-3548]. In the peptoglycan/polysaccharide-induced inflammatory arthritis model, a proteasome inhibitor improved the arthritis score by suppressing the activation of NF-κB, reducing the expression of cell adhesion molecules and IL-6. In addition, proteasome inhibition may regulate the development of inflammatory arthritis by controlling angiogenesis [*J. Mol. Med.* 2003, 81, 235-245].

Psoriasis is one of the prototypical T cell-mediated diseases, and its development is related to the activation of NF-κB. Administration of a proteasome inhibitor has been reported to reduce the size of psoriatic lesions in human skin explants grafted onto mice. The treatment also resulted in reduced super antigen-mediated T-cell activation, attenuated cell adhesion molecule expression and decreased expression of T-cell activation markers that were significantly elevated during the disease process [*J. Clin. Invest.* 2002, 109, 671-679].

In addition, other studies showed oral proteasome inhibition by bortezomib significantly limited overall inflammation, reduced the activation of NF-κB, lowered cell adhesion molecule expression, inhibited nitric oxide synthase activity, attenuated the circulating levels of IL-6, reduced the arthritic index and swelling observed in the joints of the animals, and improved the histologic appearance of the joints compared with vehicle-treated animals [*Carcinogenesis* 2000, 2, 505-515].

A link between proteasome inhibition, allergy and asthma has also been shown. Abnormal activation of type 2 helper T cells (Th2) results in asthmatic and allergic symptoms [*Nat. Immunol.* 2002, 3, 715-720]. E3 ubiquitin ligase Itch plays a useful role in maintaining immune tolerance mediated through Th2 cells both in vitro and in vivo. Itch deficient mice failed to block the development of airway inflammation in an allergic model [*J. Clin. Invest.* 2006, 116, 1117-1126]. Consistent with these findings, useful therapeutic effects were observed in a rodent model of allergen-induced asthma [*J. Allergy Clin. Immunol.* 1999, 104, 294-300].

Other inflammatory and autoimmune diseases have been linked to the ubiquitin-proteasome system (UPS), such as seronegative spondyloarthropathies (SpA) which are a group of diseases characterized by, but not limited to, axial joint inflammation. Ankylosing spondylitis (AS) is the prototypical SpA. Most patients with AS carry the MHC class I HLA-B27 gene, and therefore much research effort has been directed at understanding the role of this gene in the disease pathogenesis. There has also been interest focused on determining the origin and nature of the peptides being presented by HLA-B27 and the cell surface expression of misfolded HLA-B27, two areas in which the UPS is known to play a role.

The UPS is involved in the regulation or induction of apoptosis. Apoptosis has been implicated in both experimental models and clinical systemic lupus erythematosus (SLE). In mature, activated lymphocytes, the proteasome inhibitor lactacystin induces DNA fragmentation and apoptosis in a dose-dependent fashion, indicating that proteasome suppresses apoptosis in these cells. Altered clearance of auto antigens is thought to allow for targeting by the immune system and the development of autoimmunity. The involvement of UPS in regulating the levels of Ku70 and other autoantigens has been reported [*J. Biol. Chem.* 1998, 273, 31068-31074; *J. Cell. Sci.* 1994, 107 (Pt 11), 3223-3233; *Exp. Cell. Res.* 2006, 312, 488-499].

Proteasome inhibition has also been linked to heart disease. Evidence continues to emerge to support a hypothesis that proteasome functional insufficiency represents a common pathological phenomenon in a large subset of heart disease, compromises protein quality control in heart muscle cells, and thereby acts as a major pathogenic factor promoting the progression of the subset of heart disease to congestive heart failure. This front is represented by the studies on the UPS in cardiac proteinopathy, which have taken advantage of a transgenic mouse model expressing a fluorescence reporter for UPS proteolytic function.

In addition, pharmacological inhibition of the proteasome has been explored experimentally as a potential therapeutic strategy to intervene on some forms of heart disease, such as pressure-overload cardiac hypertrophy, viral myocarditis, and myocardial ischemic injury [*Biochimica et Biophysica Acta*—Gene Regulatory Mechanisms, 1799(9), 2010, 597-668]. Furthermore, initial reports on the effects of proteasome inhibitors in cardiovascular diseases, indicate that proteasome inhibition might be a useful therapeutic strategy for the reduction of the proliferative phenomena of the progression stage of atherogenesis [*Cardiovasc. Res.* 2004, 61, 11-21]. Recent data on the improvement of endothelium-dependent vasorelaxation in vitro, correlating with an increase in endothelial nitric oxide synthase (eNOS) expression, suggest a therapeutic potential of proteasome inhibition in the early stages of atherosclerosis [*FASEB* 2004, 18, 272-279].

Proteasome inhibitors have been shown to exert a substantial anti-inflammatory effect, which was attributed to a reduction in the activity of the factor NF-κB [*Cardiovasc. Res.* 2004, 61, 11-21]. As the pathogenesis of cardiovascular events in diabetic patients involves inflammation, the use of proteasome inhibitors may be a useful therapy. In addition to epidemiological evidence for the role of inflammation in diabetes-associated cardiovascular events, clinical studies of patients on cardio-protective drug regimens have revealed that many of the pharmacotherapies mediate their benefits, at least in part, through anti-inflammatory activities. This is the case for one class of drugs that improves adipose tissue physiology and insulin sensitivity, the peroxisome proliferator-activated receptor-γ (PPARγ) agonists [*Arterioscler. Thromb. Vasc. Biol.* 2002, 22, 717-726]. For example, the PPARγ agonist rosiglitazone, reducing inflammation, may prevent plaque progression to an unstable phenotype in diabetic patients with asymptomatic carotid stenosis, enlisted to undergo carotid endarterectomy for extracranial high-grade (>70%) internal carotid artery stenosis [*Diabetes* 2006, 55, 622-632].

The anti-inflammatory effects of glitazones are felt to be mediated partly by their beneficial effects on glycemia, but there is also evidence that glitazones may directly modulate inflammation via transcription factors such as NF-κB [*Arterioscler. Thromb. Vasc. Biol.* 2002, 22, 717-726]. In line with this, recent data have shown an inhibitory effect of rosiglitazone on ubiquitin-proteasome activity in diabetic lesions [*Diabetes* 2006, 55, 622-632]. At the same level of blood glucose levels, diabetic patients treated with rosiglitazone had the lowest level of ubiquitin and proteasome 20S activity, plaque inflammatory cells, cytokines, oxidative stress and MMP-9 associated with the highest content of plaque interstitial collagen. Patients assigned to rosiglitazone had lesser plaque progression to an unstable phenotype compared with patients assigned to placebo.

For aspirin and statins, two of the most successful drugs in treatment of cardiovascular diseases, a proteasome inhibitory effect has been described [*Mol. Pharmacol.* 2002, 62, 1515-1521].

Drugs that modulate the proteasomal degradation of proteins could be useful agents for the treatment of insulin-resistant and type-2 diabetes, and pharmacological therapies targeting UPS activity may be useful in the treatment of vascular biology disorders associated with diabetes [*Cardiovascular Diabetology* 2007, 6:35, 1-9].

The ubiquitin-proteasome system is also believed to degrade the major contractile skeletal muscle proteins and plays a major role in muscle wasting. Different and multiple events in the ubiquitination, deubiquitination and proteolytic machineries are responsible for the activation of the system and subsequent muscle wasting. However, other proteolytic enzymes act upstream (possibly m-calpain, cathepsin L, and/or caspase-3) and downstream (tri-peptidyl-peptidase II and amino-peptidases) of the UPS, for the complete breakdown of the myofibrillar proteins into free amino acids. Recent studies have identified a few proteins that seem necessary for muscle wasting i.e. the MAFbx (muscle atrophy F-box protein, also called atrogin-1) and MuRF-1 (muscle-specific RING ubiquitin-protein ligases) proteins. The characterization of their signaling pathways is leading to new pharmacological approaches that can be useful to block or partially prevent muscle wasting in human patients [*Essays Biochem.* 2005, 41, 173-86].

The UPS has also been linked to the development of human obesity. For example, it was shown that there is a possible correlation between plasma ubiquitin, 26S proteasome levels, and obesity. The body mass index (BMI), plasma ubiquitin levels, and 26S proteasome activity levels were determined and statistically analyzed. Comparison of the immunoglobulin among the underweight, normal weight, and overweight groups demonstrated that plasma ubiquitin is significantly decreased in obese individuals versus normal controls, and plasma ubiquitin levels were found to be inversely correlated with the BMI. In addition, there was an inverse relationship between 20S proteasome levels in red blood cells and BMI, whereas 26S proteasome activity was found to be dependent quantitatively to S5a in erythrocytes. Furthermore, immunoglobulin is significantly decreased in overweight individuals versus normal controls [*Metabolism* 2009, 58(11), 1643-8].

A wide variety of preclinical and early clinical studies have been performed to test the potential usefulness of proteasome inhibitors for the treatment of neurodegenerative disorders, including Alzheimer's (AD) and Parkinson's (PD) diseases. These CNS disorders are characterized by a selective loss of neurons in specific, but different, regions of the brain, and the result is often a disruption to motor, sensory or cognitive systems, resulting in severe disability of the patient. The pathological characteristic of many neurodegenerative diseases is the presence of distinctive ubiquitin-positive, intra- or extracellular inclusion bodies in affected regions of the brain. In general, these inclusions are made up of insoluble, unfolded, ubiquitylated polypeptides that fail to be targeted and degraded by the 26S proteasome [*J. Pathol.* 1988, 155, 9-15; *Neuron* 2001, 29, 15-32]. Their apparent stability may, in part, be due to decreased levels of 26S proteasomal activity that is associated with increasing age [*Ann. N.Y. Acad. Sci.* 2001, 928, 54-64].

Proteins associated with the UPS are now known to play either a direct or indirect role in familial forms of neurodegenerative disease and, in particular, PD. UPS-mediated post-translational modification and degradation of proteins is useful for most cellular processes such as cell cycling, DNA repair, cell signaling, gene transcription and apoptosis. Historically, it was recognized that the UPS is the major route by which proteins are selected for temporal and spatial degradation in eukaryotic organisms [*Cell* 2004, 116, 181-190; *Nat. Rev. Mol. Cell Biol.* 2003, 4, 192-201]. The key constituents of the inclusions associated with neurodegenerative disorders are mis-folded proteins. The major causes of protein mis-folding and subsequent loss of function are mis-sense mutations, modifications or posttranslational damage of proteins, or expansion of amino acid repeats as is observed in polyglutamine (polyQ) disorders such as Huntington's disease (HD).

Of all the neurodegenerative diseases, PD is most closely associated with aberrant protein processing via the UPS. Indeed, of the known proteins associated with hereditary forms of PD, Parkin and UCH-L1 are components of the UPS, whereas modified and/or mutant α-Synuclein and DJ-1 are degraded by the system [*Nature* 1998, 392, 605-608; *Nature* 1998, 395, 451-452; *J. Biol. Chem.* 2003, 278, 36588-36595].

A wide variety of preclinical and early clinical studies have been performed to test the potential usefulness of proteasome inhibitors for the treatment of Alzheimer's disease [*J. Neurochem.* 1999, 72, 255-261], amyotrophic lateral sclerosis [*J. Neurol. Sci.* 1996, 139, 15-20], autoimmune thyroid disease [*Tissue Antigens.* 1997, 50, 153-163], cachexia [*N. Engl. J. Med.* 1996, 335, 1897-1905; *Am. J. Physiol.* 1999, 277, 332-341], Crohn's disease [*J. Pharmacol. Exp. Ther.* 1997, 282, 1615-1622], Hepatitis B [*Oncogene*, 1998, 16, 2051-2063], inflammatory bowel disease [*Inflamm. Bowel Dis.* 1996, 2, 133-147], sepsis [*Ann. Surg.* 1997, 225, 307-316], systemic lupus erythematosus [*J. Exp. Med.* 1996, 10, 1313-1318], and transplantation rejection and related immunology [*Drug Discov. Today* 1999, 4, 63-70; *Transplantation* 2001, 72, 196-202].

The ubiquitin-proteasome system is also believed to play roles in the pathogenesis of eye diseases. Accumulation of the cytotoxic abnormal proteins in eye tissues is etiologically associated with many age-related eye diseases such as retina degeneration, cataract, and certain types of glaucoma. Age- or stress-induced impairment or overburdening of the UPP appears to contribute to the accumulation of abnormal proteins in eye tissues. Cell cycle and signal transduction are regulated by the conditional UPP-dependent degradation of the regulators of these processes. Impairment or overburdening of the UPP could also result in dysregulation of cell cycle control and signal transduction. The consequences of the improper cell cycle and signal transduction include defects in ocular development, wound healing, angiogenesis, or inflammatory responses. Methods that enhance or preserve UPP function or reduce its burden may be useful strategies for preventing age-related eye diseases [*Pro. Mol. Biol. & Trans. Sc.*, Vol. 109, 2012, 347-396].

The search for subunit selective inhibitors is predominantly conducted by either screening of natural products [*Bioorg. Med. Chem. Lett.* 1999, 9, 3335-3340], rational design [*Chem. Biol.* 2009, 16, 1278-1289], or compound library building [*Proc. Natl. Acad. Sci. USA* 2001, 98, 2967-2972; *Org. Biomol. Chem.* 2007, 5, 1416-1426]. It was noted that in these studies the effect of fluorine functionality in proteasome inhibitors is relatively uncharted [*Bioorg. Med. Chem. Lett.* 2009, 19, 83-86].

The epoxomicin analog PR-047 was recently reported to be an orally-bioavailable candidate that displayed moderate to poor metabolic properties [*J. Med. Chem.* 2009, 52, 3028-3038]. While not wishing to be limited by theory, this poor metabolic property is thought to be due to the methoxy groups in the serine (OMe) side-chains undergoing demethylation to the 0-desmethyl metabolite. A need therefore exists to find a route to block this demethylation pathway to give compounds having useful clinical profile.

SUMMARY

A novel class of halogenated epoxyketone-based proteasome inhibitors of Formula I has been prepared and found to be useful in the treatment of cancers and other proteasome mediated or associated disorders.

Accordingly, the present application includes a compound of Formula I or a pharmaceutically acceptable salt, solvate or prodrug thereof:

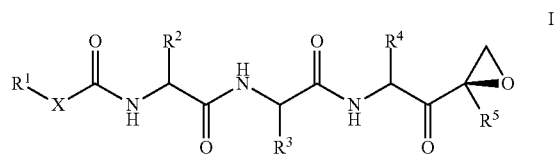

wherein:

$R^1$ is selected from the group consisting of $C_{1-10}$alkyl, $C_{2-10}$alkenyl, $C_{2-10}$alkynyl, $C_{1-10}$haloalkyl, $C_{1-10}$cyanoalkyl, $C_{1-10}$alkoxy, $C_{2-10}$alkenyloxy, $C_{2-10}$alkynyloxy, $C_{3-10}$cycloalkyl, heterocycloalkyl, aryl, heteroaryl, $C_{1-6}$alkylene-O—$C_{1-6}$haloalkyl, $C_{1-6}$alkylene-O—$C_{1-6}$haloalkyl, $C_{2-6}$alkenylene-O—$C_{1-6}$haloalkyl, $C_{2-6}$alkynylene-O—$C_{1-6}$haloalkyl, $C_{1-6}$alkylene-$C_{3-8}$cycloalkyl, $C_{1-6}$alkylene-heterocycloalkyl, $C_{1-6}$alkylene-aryl, $C_{1-6}$alkylene-heteroaryl, $C(O)R^7$, $OC(O)R^7$, $C(O)OR^7$, $C_{1-6}$alkylene-O—$R^7$, $C_{1-6}$alkylene-C(O)$R^7$, $C_{1-6}$alkylene-O—C(O)$R^7$, $C_{1-6}$alkylene-C(O)O$R^7$, $C_{1-6}$alkylene-O—C(O)O$R^7$, $C_{1-6}$alkylene-NR$^7$R$^8$, $C_{1-6}$alkylene-C(O)NR$^7$R$^8$, $C_{1-6}$alkylene-NR$^7$C(O)R$^8$, $C_{1-6}$alkylene-NR$^7$C(O)NR$^7$R$^8$, $C_{1-6}$alkylene-S—R$^7$, $C_{1-6}$alkylene-S(O)R$^7$, $C_{1-6}$alkylene-SO$_2$R$^7$, $C_{1-6}$alkylene-SO$_2$NR$^7$R$^8$, $C_{1-6}$alkylene-NR$^7$SO$_2$R$^8$, $C_{1-6}$alkylene-NR$^7$SO$_2$NR$^7$R$^8$, $C(O)NR^7R^8$ and $C_{1-6}$alkylene-NR$^7$C(O)OR$^8$, wherein any cyclic moiety is optionally substituted with $C_{1-4}$alkyl and/or is optionally fused to a further cyclic moiety;

X is absent or is selected from the group consisting of O, NH, NC$_{1-6}$alkyl, S, S(O), SO$_2$, C(O), $C_{1-6}$alkylene, $C_{2-6}$alkenylene, $C_{2-6}$alkynylene, $C_{1-6}$haloalkylene, $C_{3-8}$cycloalkylene, heterocycloalkylene, arylene and heteroarylene, or X is a combination of two or three of O, NH, NC$_{1-6}$alkyl, S, S(O), SO$_2$, $C_{1-6}$alkylene, $C_{2-6}$alkenylene, $C_{2-6}$alkynylene, $C_{1-6}$haloalkylene, $C_{3-8}$cycloalkylene, heterocycloalkylene, arylene or heteroarylene, bonded together in a linear fashion, provided that two or three of O, NH, NC$_{1-6}$alkyl, S, S(O) and SO$_2$ and not bonded directly to each other;

$R^2$, $R^3$ and $R^4$ are each independently selected from the group consisting of $C_{1-10}$alkyl, $C_{2-10}$alkenyl, $C_{2-10}$alkynyl, $C_{1-10}$haloalkyl, $C_{1-10}$cyanoalkyl, $C_{1-10}$alkoxy, $C_{2-10}$alkenyloxy, $C_{2-10}$alkynyloxy, $C_{3-10}$cycloalkyl, heterocycloalkyl, aryl, heteroaryl, $C_{1-6}$alkylene-O—$C_{1-6}$alkyl, $C_{1-6}$alkylene-O—$C_{1-6}$haloalkyl, $C_{2-6}$alkenylene-O—$C_{1-6}$haloalkyl, $C_{2-6}$alkynylene-O—$C_{1-6}$haloalkyl, $C_{1-6}$alkylene-$C_{3-8}$cycloalkyl, $C_{1-6}$alkylene-heterocycloalkyl, $C_{1-6}$alkylene-aryl, $C_{1-6}$alkylene-heteroaryl, $C(O)R^7$, $OC(O)R^7$, $C(O)OR^7$, $C_{1-6}$alkylene-O—$R^7$, $C_{1-6}$alkylene-C(O)$R^7$, $C_{1-6}$alkylene-O—C(O)$R^7$, $C_{1-6}$alkylene-C(O)OR$^7$, $C_{1-6}$alkylene-O—C (O)OR$^7$, C$_{1-6}$alkylene-NR$^7$R$^5$, C$_{1-6}$alkylene-C(O)NR$^7$R$^8$, C$_{1-6}$alkylene-NR$^7$C(O)R$^8$, C$_{1-6}$alkylene-NR$^7$C(O)NR$^7$R$^8$, C$_{1-6}$alkylene-S—R$^7$, C$_{1-6}$alkylene-S(O)R$^7$, C$_{1-6}$alkylene-SO$_2$R$^7$, C$_{1-6}$alkylene-SO$_2$NR$^7$R$^8$, C$_{1-6}$alkylene-NR$^7$SO$_2$R$^8$, C$_{1-6}$alkylene-NR$^7$SO$_2$NR$^7$R$^8$, C(O)NR$^7$R$^8$ and C$_{1-6}$alkylene-NR$^7$C(O)OR$^8$, wherein any cyclic moiety is optionally fused to a further 5- to 7-membered cyclic moiety, wherein at least one of R$^2$, R$^3$ and R$^4$ is C$_{1-6}$-alkylene-O—C$_{1-6}$haloalkyl, and wherein R$^2$, R$^3$ and R$^4$ are optionally substituted with one or more independently-selected R$^6$ groups;

R$^5$ is selected from the group consisting of H, C$_{1-6}$alkyl, C$_{2-6}$alkenyl, C$_{2-6}$alkynyl, C$_{3-8}$cycloalkyl, C$_{1-6}$alkylene-C$_{3-8}$cycloalkyl, aryl, heteroaryl, and heterocycloalkyl;

R$^6$ is selected from the group consisting of C$_{1-6}$alkyl, OH, halo, O—(C$_{2-3}$alkylene)-O, C$_{1-6}$alkoxy, aryloxy, —NH—C$_{1-6}$alkyl, —N(C$_{1-6}$alkyl)$_2$, C$_{1-6}$alkylene-N(C$_{1-6}$alkyl)$_2$, cycloalkyl, heterocycloalkyl, aryl and heteroaryl; and R$^7$ and R$^8$ are each independently selected from the group consisting of H, C$_{2-6}$alkenyl, C$_{2-6}$alkynyl, C$_{3-10}$cycloalkyl, C$_{1-6}$alkylene-C$_{3-10}$cycloalkyl, heterocycloalkyl, aryl, C$_{1-6}$alkylene-aryl, C$_{1-6}$alkylene-heterocycloalkyl, heteroaryl, and C$_{1-6}$alkylene-heteroaryl, wherein any cyclic moiety is optionally fused to a further cyclic moiety.

The present application also includes a composition comprising one or more compounds of the application and a carrier. In an embodiment, the composition is a pharmaceutical composition comprising one or more compounds of the application and a pharmaceutically acceptable carrier.

The compounds of the application have been shown to inhibitors of proteasome activity. Therefore the compounds of the application are useful for treating diseases, disorders or conditions mediated by or associated with proteasome inhibition. Accordingly, the present application also includes a method of treating a disease, disorder or condition mediated by proteasome inhibition, comprising administering a therapeutically effective amount of one or more compounds of the application to a subject in need thereof.

In a further embodiment, the compounds of the application are used as medicaments. Accordingly, the application also includes a compound of the application for use as a medicament.

The present application also includes a use of one or more compounds of the application for treatment of a disease, disorder or condition mediated by proteasome inhibition, as well as a use of one or more compounds of the application for the preparation of a medicament for treatment of a disease, disorder or condition mediated by proteasome inhibition. The application further includes one or more compounds of the application for use in treating a disease, disorder or condition mediated by proteasome inhibition.

In an embodiment, the disease, disorder or condition mediated by proteasome inhibition is a neoplastic disorder. In an embodiment, the treatment is in an amount effective to ameliorate at least one symptom of the neoplastic disorder, for example, reduced cell proliferation or reduced tumor mass in a subject in need of such treatment.

In an embodiment, the disease, disorder or condition mediated by proteasome inhibition is cancer.

In an embodiment, the disease, disorder or condition mediated by proteasome inhibition is a disease, disorder or condition associated with an uncontrolled and/or abnormal cellular activity affected directly or indirectly by proteasome inhibition. In another embodiment, the uncontrolled and/or abnormal cellular activity that is affected directly or indirectly by proteasome inhibition is proliferative activity in a cell.

The application also includes a method of inhibiting proliferative activity in a cell, comprising administering an effective amount of one or more compounds of the application to the cell.

In a further embodiment the disease, disorder or condition mediated by proteasome inhibition is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

In another embodiment, the disease, disorder or condition mediated by proteasome inhibition is selected from by proteasome inhibition is selected from a viral infection, an inflammatory disease, an autoimmune disease, heart disease, an age-related eye disease and a neurodegenerative disease.

The application additionally provides a process for the preparation of compounds of Formula I. General and specific processes are discussed in more detail and set forth in the Examples below.

In an embodiment of the present application, the compounds of Formula I comprise at least one fluorine atom. Factors to be considered when synthesising fluorine-containing compounds include (a) the relatively small size of the fluorine atom (van der Waals radius of 1.47 Å), comparable to hydrogen (van der Waals radius of 1.20 Å), (b) the highly electron-withdrawing nature of fluorine, (c) the greater stability of the C—F bond compared to the C—H bond and (d) the greater lipophilicity of fluorine compared to hydrogen. The introduction of a fluorine atom into a molecule can alter the physicochemical properties of the compound due to its electronegativity.

The introduction of a halogen atom into a molecule also provides the opportunity for the use of the molecule in radiolabeling applications. For example, $^{18}$F is used as a radiolabel tracer in the sensitive technique of Positron Emission Tomography (PET). Accordingly the present application also includes methods of using the compounds of Formula I for diagnostic and imaging purposes.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings, in which.

DETAILED DESCRIPTION

I. Definitions

Figure 1:
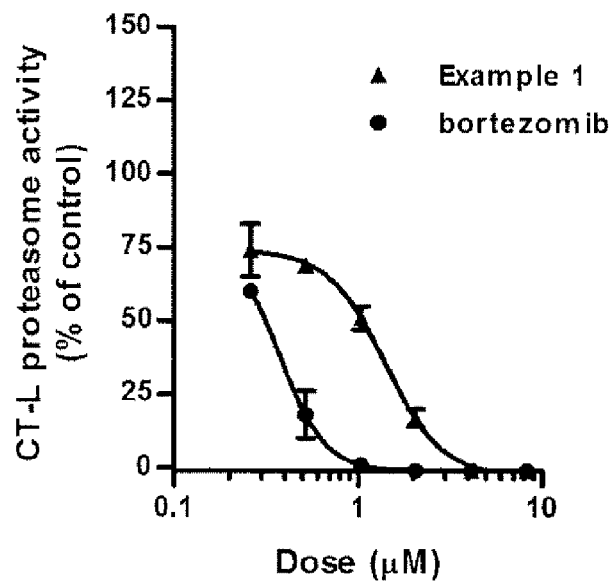
FIG. 1 shows the effect of a representative compound of the application (the compound of Example 1) on the enzymatic activity of purified proteasomes, compared to bortezomib. Purified beta proteasome subunits from the archaebacteria *Thermoplasma acidophilum* (A) or whole cell lysates from the human myeloma cell line LP1 (B).
Figure 1:
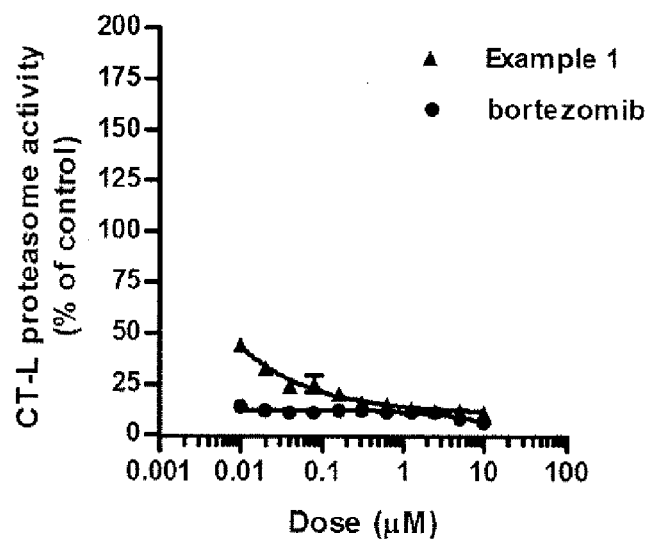

Unless otherwise indicated, the definitions and embodiments described in this and other sections are intended to be applicable to all embodiments and aspects of the application herein described for which they are suitable as would be understood by a person skilled in the art. Unless otherwise specified within this application or unless a person skilled in the art would understand otherwise, the nomenclature used in this application generally follows the examples and rules stated in "Nomenclature of Organic Chemistry" (Pergamon Press, 1979), Sections A, B, C, D, E, F, and H. Optionally, a name of a compound may be generated using a chemical naming program: ACD/ChemSketch, Version 5.09/September 2001, Advanced Chemistry Development, Inc., Toronto, Canada.

The term "compound of the application" or "compound of the present application" and the like as used herein refers to a compound of Formula I, or a pharmaceutically acceptable salt, solvate and/or prodrug thereof.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the species to be transformed, but the selection would be well within the skill of a person trained in the art. All method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

In embodiments of the present application, the compounds described herein having a double bond can exist as geometric isomers, for example cis or trans isomers. It is to be understood that all such geometric isomers and mixtures thereof in any proportion are encompassed within the scope of the present application. It is to be further understood that while the stereochemistry of these compounds may be as shown in any given compound listed herein, such compounds may also contain certain amounts (for example, less than 20%, suitably less than 10%, more suitably less than 5%) of compounds of the present application having alternate stereochemistry.

The compounds of the present application can also exist in different tautomeric forms and it is intended that any tautomeric forms which the compounds form, are included within the scope of the present application.

The compounds of the present application may further exist in varying polymorphic forms and it is contemplated that any polymorphs which form, are included within the scope of the present application.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The expression "proceed to a sufficient extent" as used herein with reference to the reactions or method steps disclosed herein means that the reactions or method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

The term "seven-membered" or "7-membered" as used herein as a prefix refers to a group having a ring that contains seven ring atoms.

The term "six-membered" or "6-membered" as used herein as a prefix refers to a group having a ring that contains six ring atoms.

The term "five-membered" or "5-membered" as used herein as a prefix refers to a group having a ring that contains five ring atoms.

The term "hydrocarbon" as used herein, whether it is used alone or as part of another group, refers to any structure comprising only carbon and hydrogen atoms up to 14 carbon atoms.

The term "hydrocarbon radical" or "hydrocarbyl" as used herein, whether it is used alone or as part of another group, refers to any structure derived as a result of removing a hydrogen atom from a hydrocarbon.

The term "hydrocarbylene" as used herein, whether it is used alone or as part of another group, refers to any structure derived as a result of removing a hydrogen atom from two ends of a hydrocarbon.

The term "alkyl" as used herein, whether it is used alone or as part of another group, means straight or branched chain, saturated hydrocarbyl groups. For example, the term $C_{1-10}$alkyl means an alkyl group having 1, 2, 3, 4, 5, 6, 7, 8, 9 or 10 carbon atoms.

The term "alkylene" as used herein means straight or branched chain, saturated hydrocarbyl group, that is a saturated carbon chain that contains substituents on two of its ends. For example, the term $C_{1-10}$alkylene means an alkylene group having 1, 2, 3, 4, 5, 6, 7, 8, 9 or 10 carbon atoms.

The term "alkenyl" as used herein, whether it is used alone or as part of another group, means straight or branched chain, unsaturated alkenyl groups. For example, the term $C_{2-10}$alkenyl means an alkenyl group having 2, 3, 4, 5, 6, 7, 8, 9 or 10 carbon atoms and at least one double bond, for example 1-3, 1-2 or 1 double bond.

The term "alkenylene" as used herein means straight or branched chain, unsaturated alkenylene group, that is an unsaturated carbon chain that contains substituents on two of its ends. For example, the term $C_{2-6}$alkenylene means an alkenylene group having 2, 3, 4, 5, 6, 7, 8, 9 or 10carbon atoms and at least 1, for example 1-3, 1-2 or 1 double bond.

The term "alkynyl" as used herein, whether it is used alone or as part of another group, means straight or branched chain unsaturated alkynyl groups. The term $C_{2-6}$alkynyl means an alkynyl group having 2, 3, 4, 5 or 6 carbon atoms and at least one triple bond, for example 1-3, 1-2 or 1 triple bond.

The term "alkynylene" as used herein means straight or branched chain, unsaturated alkynylene group, that is an unsaturated carbon chain that contains substituents on two of its ends. The term $C_{2-6}$alkynylene means an alkynylene group having 2, 3, 4, 5 or 6 carbon atoms and at least 1, for example 1-3, 1-2 or 1 triple bond.

The term "haloalkyl" as used herein refers to an alkyl group wherein one or more, including all of the hydrogen atoms are replaced by a halogen atom. In an embodiment, the halogen is fluorine, in which case the haloalkyl is referred to herein as a "fluoroalkyl" group. In another embodiment, the haloalkyl comprises at least one —$CHF_2$ group.

The term "haloalkylene" as used herein refers to an alkylene group wherein one or more, including all of the hydrogen atoms are replaced by a halogen atom. In an embodiment, the halogen is fluorine, in which case the haloalkylene is referred to herein as a "fluoroalkylene" group. In another embodiment, the haloalkylene comprises a branched fluoroalkylene having at least one —$CHF_2$ group.

The term "cyanoalkyl" as used herein refers to an alkyl group that is substituted by at least one cyano group. For example, the term $C_{1-10}$cyanoalkyl means an alkyl group having 1, 2, 3, 4, 5, 6, 7, 8, 9 or 10 carbon atoms and at least one cyano group attached thereto.

The term "alkoxy" as used herein, whether it is used alone or as part of another group, refers to the group "alkyl-O—". For example, the term $C_{1-10}$alkoxy means an alkyl group having 1, 2, 3, 4, 5, 6, 7, 8, 9 or 10 carbon atoms bonded to the oxygen atom of the alkoxy group. Exemplary alkoxy groups include without limitation methoxy, ethoxy, propoxy, isopropoxy, butoxy, t-butoxy and isobutoxy.

The term "alkenyloxy" as used herein, whether it is used alone or as part of another group, refers to the group "alkenyl-O—". For example, the term $C_{2-10}$alkenyloxy means an alkenyl group having 2, 3, 4, 5, 6, 7, 8, 9 or 10 carbon atoms and at least one double bond bonded to the oxygen atom of the alkenyloxy group. An exemplary alkoxy group is an allyloxy group.

The term "alkynyloxy" as used herein, whether it is used alone or as part of another group, refers to the group "alkynyl-O—". For example, the term $C_{2-10}$alkynyloxy means an alkynyl group having 2, 3, 4, 5, 6, 7, 8, 9 or 10 carbon atoms and at least one triple bond bonded to the oxygen atom of the alkynyloxy group. An exemplary alkoxy group is a propargyloxy group.

The term "aryloxy" as used herein, whether it is used alone or as part of another group, refers to the group "aryl-O—". In an embodiment of the present disclosure, the aryl group contains 6, 9, 10 or 14 atoms such as phenyl, naphthyl, indanyl or anthracenyl.

The term "cycloalkyl," as used herein, whether it is used alone or as part of another group, means saturated alkyl groups having at least one cyclic ring. For example, the term $C_{3-10}$cycloalkyl means a cycloalkyl group having 3, 4, 5, 6, 7, 8, 9 or 10 carbon atoms.

The term "cycloalkylene" as used herein refers to a cycloalkyl group that contains substituents on two of its ends.

The term "aryl" as used herein, whether it is used alone or as part of another group, refers to cyclic groups that contain at least one aromatic ring. In an embodiment of the application, the aryl group contains from 6, 9, 10 or 14 atoms, such as phenyl, naphthyl, indanyl or anthracenyl.

The term "arylene" as used herein refers to an aryl group that contains substituents on two of its ends.

The term "heteroarylene" as used herein refers to a heteroaryl group that contains substituents on two of its ends.

The term "heterocycloalkyl" as used herein, whether it is used alone or as part of another group, refers to a non-aromatic, ring-containing group having one or more multivalent heteroatoms, independently selected from the group consisting of N, O and S, as a part of the ring structure and including at least 3 and up to 20 atoms in the ring(s). Heterocycloalkyl groups are either saturated or unsaturated (i.e. contain one or more double bonds) and may contain more than one ring. When a heterocycloalkyl group contains more than one ring, the rings may be fused, bridged, Spiro connected or linked by a single bond.

A first ring group being "fused" with a second ring group means the first ring and the second ring share at least two adjacent atoms there between.

A first ring group being "bridged" with a second ring group means the first ring and the second ring share at least two non-adjacent atoms there between.

A first ring group being "spiro connected" with a second ring group means the first ring and the second ring share one atom there between.

Heterocycloalkyl includes monocyclic heterocycloalkyls such as but not limited to aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. Additionally, heterocycloalkyl includes polycyclic heterocycloalkyls such as but not limited to pyrolizidinyl, and quinolizidinyl. In addition to the polycyclic heterocycloalkyls described above, heterocycloalkyl includes polycyclic heterocycloalkyls wherein the ring fusion between two or more rings includes more than one bond common to both rings and more than two atoms common to both rings. Examples of such bridged heterocycles include but are not limited to quinuclidinyl, diazabicyclo[2.2.1]heptyl and 7-oxabicyclo[2.2.1]heptyl.

The term "heteroaryl" as used herein means a monocyclic ring or a polycyclic ring system containing 5, 6, 7, 8, 9, 10, 11, 12, 13, 14, 15, 16, 17, 18, 19 or 20 atoms, of which one or more, for example 1 to 8, 1 to 6, 1 to 5, or 1 to 4, of the atoms are a heteromoiety selected from O, S, NH and $NC_{1-6}$alkyl, with the remaining atoms being C, CH or $CH_2$, said ring system containing at least one aromatic ring.

Heteroaryl includes for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4 oxadiazolyl.

Heteroaryl also includes polycyclic heteroaryls such as but not limited to indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl and acridinyl.

A five-membered heteroaryl is a heteroaryl with a ring having five ring atoms, where 1, 2 or 3 ring atoms are a heteromoiety selected from O, S, NH and $NC_{1-6}$alkyl, Exemplary five-membered heteroaryls include but are not limited to thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl is a heteroaryl with a ring having six ring atoms wherein 1, 2 or 3 ring atoms are a heteromoiety selected from O, S, NH and $NC_{1-6}$alkyl, Exemplary six-membered heteroaryls include but are not limited to pyridyl, pyrazinyl, pyrimidinyl, triazinyl and pyridazinyl.

The term "cyclic moiety" as used herein refers to any cycloalkyl, aryl, heteroaryl or heterocycloalkyl group as defined herein.

The term "heteromoiety" as used herein refers to a group of atoms containing at least one heteroatom.

As a prefix, the term "substituted" as used herein refers to a structure, molecule or group in which one or more available hydrogen atoms are replaced with one or more other chemical groups. In an embodiment, the chemical group is a $C_{1-4}$alkyl. In another embodiment, the chemical group is a $C_{1-12}$alkyl or a chemical group that contains one or more heteroatoms selected from N, O, S, F, Cl, Br, I, and P. Exemplary chemical groups containing one or more heteroatoms include heterocycloalkyl, heteroaryl, —$NO_2$, —OR, —R'OR, —Cl, —Br, —I, —F, —$CF_3$, —C(O)R, —$NR_2$, —SR, —$SO_2$R, —S(O)R, —CN, —C(O)OR, —C(O)$NR_2$, —NRC(O)R, —NRC(O)OR, —R'$NR_2$, oxo (O), imino (=NR), thio (=S), and oximino (=N—OR), wherein each "R" is hydrogen or a $C_{1-12}$alkyl and "R'" is a $C_{1-12}$alkylene. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any available hydrogen on the phenyl ring.

As a suffix, the term "substituted" as used herein in relation to a first structure, molecule or group, followed by one or more variables or names of chemical groups, refers to a second structure, molecule or group that results from replacing one or more available hydrogen atoms of the first structure, molecule or group with the one or more variables or named chemical groups. For example, a "phenyl substituted by nitro" refers to nitrophenyl.

The term "available hydrogen atoms" as used herein refers to hydrogen atoms on a molecule or group that can be replaced with another group under conditions that will not degrade or decompose the parent compound. Such conditions include the use of protecting groups to protect sensitive functional groups in the molecule while the hydrogen atom is being replaced.

The term "optionally substituted" refers to groups, structures, or molecules that are either substituted or unsubstituted.

The term "amine" or "amino," as used herein, whether it is used alone or as part of another group, refers to radicals of the general formula —NRR', wherein R and R' are each independently selected from hydrogen or a alkyl group, for example $C_{1-6}$alkyl.

The term "halo" as used herein refers to a halogen atom and includes fluoro, chloro, bromo and iodo.

The term "acac" as used herein refers to acetylacetonate.

The term "atm" as used herein refers to atmosphere.

The term "aq." as used herein refers to aqueous.

The terms "Boc" and "t-Boc" as used herein refers to the group tert-butoxycarbonyl.

DCM as used herein refers to dichloromethane.

DIPEA as used herein refers to N,N-diisopropyl ethylamine

DMF as used herein refers to dimethylformamide.

DMSO as used herein refers to dimethylsulfoxide.

EDCl.HCl as used herein refers to N-[3-(dimethylamino) propyl]-N'-ethylcarbodiimide hydrochloride.

EDC as used herein refers to 1-ethyl-3-(3-dimethylaminopropyl)carbodiimide.

$Et_2O$ as used herein refers to diethylether.

EtOAc as used herein refers to ethyl acetate.

Et as used herein refers to the group ethyl.

Fmoc as used herein refers to the group 9-fluorenylmethyloxycarbonyl.

The term "hr(s)" as used herein refers to hour(s).

The term "min(s)" as used herein refers to minute(s).

HOBt as used herein refers to N-hydroxybenzotriazole.

HBTU as used herein refers to O-(benzotriazol-1-yl)-N, N,N',N'-tetramethyluronium hexafluorophosphate.

MeOH as used herein refers to methanol.

Me as used herein refers to the group methyl, t-BuLi as used herein refers to tert-butyllithium.

ON as used herein refers to overnight

RT as used herein refers to room temperature.

TEA as used herein refers to triethylamine.

TFA as used herein refers to trifluoroacetic acid.

THF as used herein refers to tetrahydrofuran.

t-Bu as used herein refers to the group tertiary butyl.

SPE as used herein refers to solid phase extraction, for example using columns containing silica gel for mini-chromatography.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W, Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of suitable protecting groups include, but are not limited to t-Boc, cbz, Ac, Ts, Ms, silyl ethers such as TMSi, TBDMS, TBDPS, Tf, Ns, Bn, Fmoc, benzoyl, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

Cbz as used herein refers to the group carboxybenzyl.

Ac as used herein refers to the group acetyl,

Ts (tosyl) as used herein refers to the group p-toluenesulfonyl.

Ms as used herein refers to the group methanesulfonyl.

TMS as used herein refers to tetramethylsilane.

TMSi as used herein refers to the group trimethylsilyl.

TBDMS as used herein refers to the group t-butyldimethylsilyl,

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

The term "cell" as used herein refers to a single cell or a plurality of cells and includes a cell either in a cell culture or in a subject.

The term "subject" as used herein includes all members of the animal kingdom including mammals, and suitably refers to humans. Thus the methods and uses of the present application are applicable to both human therapy and veterinary applications. In an embodiment, the subject is a mammal. In another embodiment, the subject is human.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject. One non-limiting example of such a carrier is a pharmaceutically acceptable oil typically used for parenteral administration.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt. In another embodiment of the present invention, the compound of Formula I is converted to a pharmaceutically acceptable salt or solvate thereof, in particular an acid addition salt such as a hydrochloride, hydrobromide, phosphate, acetate, fumarate, maleate, tartrate, citrate, methanesulphonate or p-toluenesulphonate A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition described herein to prevent recurrence. Treatment methods comprise administering to a subject a therapeutically effective amount of one or more of the compounds of the application and optionally consist of a single administration, or alternatively comprise a series of administrations. For example, the compounds of the application may be administered at least once a week. However, in another embodiment, the compounds may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required. For example, the compounds are administered to the subject in an amount and for a duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition mediated by proteasome inhibition or manifesting a symptom associated with a disease, disorder or condition mediated by proteasome inhibition.

As used herein, the term "effective amount" or "therapeutically effective amount" means an amount effective, at dosages and for periods of time necessary to achieve the desired result. For example in the context of treating a disease, disorder or condition mediated by proteasome inhibition, an effective amount is an amount that, for example, increases proteasome inhibition compared to the proteasome inhibition without administration of the compound. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

The term "mediated by" or "associated with" as used herein refers to a disease, disorder or condition in a subject wherein at least one of the causes is the specified physiological abnormality, for example an enhanced level of proteasome activity, in particular compared to subjects that do not have the disease, disorder or condition.

The term "administered" as used herein means administration of a therapeutically effective amount of a compound or composition of the application to a cell either in cell culture or in a subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include but are not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers. Prevalent cancers include breast, prostate, colon, lung, liver, brain, ovarian and pancreatic cancers.

The term "cancer" as used herein refers to cellular-proliferative disease states, including but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

II. Compounds of the Application

Compounds of the present application were prepared and found to inhibit uncontrolled and/or abnormal cellular activities affected directly or indirectly by the proteasome. In particular, compounds of the present application exhibited activity as proteasome inhibitors, and are therefore useful in therapy, for example for the treatment of neoplastic disorders such as cancer and neurodegenerative disorders associated directly or indirectly with proteasome inhibition.

Accordingly, the present application includes a compound of Formula I or a pharmaceutically acceptable salt, solvate or prodrug thereof:

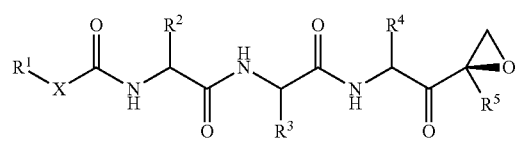

I wherein:

R¹ is selected from the group consisting of C$_{1-10}$alkyl, C$_{2-10}$alkenyl, C$_{2-10}$alkynyl, C$_{1-10}$haloalkyl, C$_{1-10}$cyanoalkyl, C$_{1-10}$alkoxy, C$_{2-10}$alkenyloxy, C$_{2-10}$alkynyloxy, C$_{3-10}$cycloalkyl, heterocycloalkyl, aryl, heteroaryl, C$_{1-6}$alkylene-O—C$_{1-6}$alkyl, C$_{1-6}$alkylene-O—C$_{1-6}$haloalkyl, C$_{2-6}$alkenylene-O—C$_{1-6}$haloalkyl, C$_{2-6}$alkynylene-O—C$_{1-6}$haloalkyl, C$_{1-6}$alkylene-C$_{3-8}$cycloalkyl, C$_{1-6}$alkylene-heterocycloalkyl, C$_{1-6}$alkylene-aryl, C$_{1-6}$alkylene-heteroaryl, C(O)R⁷, OC(O)R⁷, C(O)OR⁷, C$_{1-6}$alkylene-O—R⁷, C$_{1-6}$alkylene-C(O)R⁷, C$_{1-6}$alkylene-O—C(O)R⁷, C$_{1-6}$alkylene-C(O)OR⁷, C$_{1-6}$alkylene-O—C(O)OR⁷, C$_{1-6}$alkylene-NR⁷R⁸, C$_{1-6}$alkylene-C(O)NR⁷R⁸, C$_{1-6}$alkylene-NR⁷C(O)R⁸, C$_{1-6}$alkylene-NR⁷C(O)NR⁷R⁸, C$_{1-6}$alkylene-S—R⁷, C$_{1-6}$alkylene-S(O)R⁷, C$_{1-6}$alkylene-SO$_2$R⁷, C$_{1-6}$alkylene-SO$_2$NR⁷R⁸, C$_{1-6}$alkylene-NR⁷SO$_2$R⁸, C$_{1-6}$alkylene-NR⁷SO$_2$NR⁷R⁸, C(O)NR⁷R⁸ and C$_{1-6}$alkylene-NR⁷C(O)OR⁸, wherein any cyclic moiety is optionally substituted with C$_{1-4}$alkyl and/or is optionally fused to a further cyclic moiety;

X is absent or is selected from the group consisting of O, NH, NC$_{1-6}$alkyl, S, S(O), SO$_2$, C(O), C$_{1-6}$alkylene, C$_{2-6}$alkenylene, C$_{2-6}$alkynylene, C$_{1-6}$haloalkylene, C$_{3-8}$cycloalkylene, heterocycloalkylene, arylene and heteroarylene, or X is a combination of two or three of O, NH, NC$_{1-6}$alkyl, S, S(O), SO$_2$, C$_{1-6}$alkylene, C$_{2-6}$alkenylene, C$_{2-6}$alkynylene, C$_{1-6}$haloalkylene, C$_{3-8}$cycloalkylene, heterocycloalkylene, arylene or heteroarylene, bonded together in a linear fashion, provided that two or three of O, NH, NC$_{1-6}$alkyl, S, S(O) and SO$_2$ and not bonded directly to each other;

R², R³ and R⁴ are each independently selected from the group consisting of C$_{1-10}$alkyl, C$_{2-10}$alkenyl, C$_{2-10}$alkynyl, C$_{1-10}$haloalkyl, C$_{1-10}$cyanoalkyl, C$_{1-10}$alkoxy, C$_{2-10}$alkenyloxy, C$_{2-10}$alkynyloxy, C$_{3-10}$cycloalkyl, heterocycloalkyl, aryl, heteroaryl, C$_{1-6}$alkylene-O—C$_{1-6}$alkyl, C$_{1-6}$alkylene-O—C$_{1-6}$haloalkyl, C$_{2-6}$alkenylene-O—C$_{1-6}$haloalkyl, C$_{2-6}$alkynylene-O—C$_{1-6}$haloalkyl, C$_{1-6}$alkylene-C$_{3-8}$cycloalkyl, C$_{1-6}$alkylene-heterocycloalkyl, C$_{1-6}$alkylene-aryl, C$_{1-6}$alkylene-heteroaryl, C(O)R⁷, OC(O)R⁷, C(O)OR⁷, C$_{1-6}$alkylene-O—R⁷, C$_{1-6}$alkylene-C(O)R⁷, C$_{1-6}$alkylene-O—C(O)R⁷, C$_{1-6}$alkylene-C(O)OR⁷, C$_{1-6}$alkylene-O—C(O)OR⁷, C$_{1-6}$alkylene-NR⁷R⁸, C$_{1-6}$alkylene-C(O)NR⁷R⁸, C$_{1-6}$alkylene-NR⁷C(O)R⁸, C$_{1-6}$alkylene-NR⁷C(O)NR⁷R⁸, C$_{1-6}$alkylene-S—R⁷, C$_{1-6}$alkylene-S(O)R⁷, C$_{1-6}$alkylene-SO$_2$R⁷, C$_{1-6}$alkylene-SO$_2$NR⁷R⁸, C$_{1-6}$alkylene-NR⁷SO$_2$R⁸, C$_{1-6}$alkylene-NR⁷SO$_2$NR⁷R⁸, C(O)NR⁷R⁸ and C$_{1-6}$alkylene-NR⁷C(O)OR⁸, wherein any cyclic moiety is optionally fused to a further 5- to 7-membered cyclic moiety, wherein at least one of R², R³ and R⁴ is C$_{1-6}$-alkylene-O—C$_{1-6}$haloalkyl, and wherein R², R³ and R⁴ are optionally substituted with one or more independently-selected R⁶ groups;

R⁵ is selected from the group consisting of H, C$_{1-6}$alkyl, C$_{2-6}$alkenyl, C$_{2-6}$alkynyl, C$_{3-8}$cycloalkyl, C$_{1-6}$alkylene-C$_{3-8}$cycloalkyl, aryl, heteroaryl, and heterocycloalkyl;

R⁶ is selected from the group consisting of C$_{1-6}$alkyl, OH, halo, O—(C$_{2-3}$alkylene)-O, C$_{1-6}$alkoxy, aryloxy, —NH—C$_{1-6}$alkyl, —N(C$_{1-6}$alkyl)$_2$, C$_{1-6}$alkylene-N(C$_{1-6}$alkyl)$_2$, C$_{1-6}$alkylene-NH—C$_{1-6}$alkyl, cycloalkyl, heterocycloalkyl, aryl and heteroaryl; and R⁷ and R⁸ are each independently selected from the group consisting of H, C$_{1-6}$alkyl, C$_{1-6}$haloalkyl, C$_{2-6}$alkenyl, C$_{2-6}$alkynyl, C$_{3-10}$cycloalkyl, C$_{1-6}$alkylene-C$_{3-10}$cycloalkyl, heterocycloalkyl, aryl, C$_{1-6}$alkylene-aryl, C$_{1-6}$alkylene-heterocycloalkyl, heteroaryl, and C$_{1-6}$alkylene-heteroaryl, wherein any cyclic moiety is optionally fused to a further cyclic moiety.

In an embodiment, R¹ is selected from:
(i) C$_{1-10}$alkyl;
(ii) C$_{2-10}$alkenyl;
(iii) C$_{2-10}$alkynyl;
(iv) substituted or unsubstituted C$_{6-14}$aryl;
(v) substituted or unsubstituted heteroaryl;
(vi) substituted or unsubstituted C$_{3-10}$cycloalkyl; and
(vii) substituted or unsubstituted C$_{3-10}$heterocycloalkyl, wherein the substituents for C$_{6-14}$aryl, heteroaryl, C$_{3-10}$cycloalkyl and C$_{3-10}$heterocycloalkyl are independently selected from C$_{1-4}$alkyl.

In another embodiment, R¹ is selected from:
(i) C$_{1-6}$alkyl;
(ii) C$_{2-6}$alkenyl;
(iii) C$_{2-6}$alkynyl;
(iv) substituted or unsubstituted C$_{6-10}$aryl;
(v) substituted or unsubstituted 5- or 6-membered heteroaryl;
(vi) substituted or unsubstituted C$_{3-8}$cycloalkyl; and
(vii) substituted or unsubstituted C$_{3-8}$heterocycloalkyl, wherein the substituents for C$_{6-10}$aryl, 5- or 6-membered heteroaryl, C$_{3-8}$cycloalkyl and C$_{3-8}$heterocycloalkyl are independently selected from C$_{1-4}$alkyl.

In a further embodiment, R¹ is selected from:
(i) C$_{1-6}$alkyl;
(ii) a substituted or unsubstituted 5- or 6-membered heteroaryl; and
(iii) C$_{3-8}$heterocycloalkyl, wherein the substituents for the 5- or 6-membered heteroaryl are independently selected from C$_{1-4}$alkyl.

It is an embodiment that R¹ is selected from the group consisting of an unsubstituted 5- or 6-membered heteroaryl, a 5- or 6-membered heteroaryl substituted with a C$_{1-4}$alkyl and C$_{3-8}$heterocycloalkyl.

In an embodiment, R¹ is C$_{1-10}$alkyl. In another embodiment, R¹ is C$_{1-6}$alkyl. In a further embodiment, R¹ is t-butyl.

It is an embodiment that R¹ is an unsubstituted 5- or 6-membered heteroaryl, a 5-membered heteroaryl substituted with a C$_{1-4}$alkyl or a 6-membered heterocycloalkyl.

In an embodiment, R¹ is heterocycloalkyl. In another embodiment, R¹ is selected from morpholinyl, 1,4-oxazepanyl, thiomorpholinyl, 1,4-thiazepanyl, 1,4-thiazepanyl-1-oxide, 1,4-thiazepanyl-1,1-dioxide, 1,4-thiazinanyl-1-oxide, 1,4-thiazinanyl-1,1-dioxide, aziridinyl, azetidinyl, pyrrolidinyl, piperazinyl and 1,4-diazepanyl. In another embodiment, R¹ is a 6-membered heterocycloalkyl having one O atom and one N atom as a part of the ring structure. It is an embodiment that R¹ is morpholinyl. In another embodiment of the present application, R¹ is

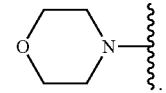

In an embodiment, R¹ is an unsubstituted 5- or 6-membered heteroaryl or a 5- or 6-membered heteroaryl substituted with a C$_{1-4}$alkyl. In another embodiment, R¹ is an unsubstituted 5-membered heteroaryl. In a further embodiment, R¹ is an unsubstituted 6-membered heteroaryl. It is an embodiment that R¹ is a 5-membered heteroaryl, substituted with a C$_{1-4}$alkyl. In another embodiment, R¹ is a 5-membered heteroaryl, substituted with a methyl.

In an embodiment, R¹ is selected from:
(i) substituted or unsubstituted thiazolyl;
(ii) substituted or unsubstituted isothiazolyl;

(iii) substituted or unsubstituted oxazolyl;
(iv) substituted or unsubstituted isooxazolyl;
(v) substituted or unsubstituted thiophenyl;
(vi) substituted or unsubstituted furanyl;
(vii) substituted or unsubstituted 1,2,4-triazolyl;
(viii) substituted or unsubstituted pyridyl;
(ix) substituted or unsubstituted pyrazinyl;
(x) substituted or unsubstituted pyrimidinyl; and
(xi) substituted or unsubstituted 1,2,4-triazinyl,
wherein the substituents for thiazolyl, isothiazolyl, oxazolyl, isooxazolyl, thiophenyl, furanyl, 1,2,4-triazolyl, pyridyl, pyrazinyl, pyrimidinyl and 1,2,4-triazinyl are independently selected from a $C_{1-4}$alkyl such as a methyl.

In another embodiment $R^1$ is selected from:
(i) substituted or unsubstituted isoxazolyl;
(ii) substituted or unsubstituted isothiazolyl;
(iii) substituted or unsubstituted furanyl;
(iv) substituted or unsubstituted thiophenyl;
(v) substituted or unsubstituted oxazolyl;
(vi) substituted or unsubstituted thiazolyl;
(vii) substituted or unsubstituted pyrazolyl; and
(viii) substituted or unsubstituted imidazolyl,
wherein the substituents for isoxazolyl, isothiazolyl, furanyl, thiophenyl, oxazolyl, thiazolyl, pyrazolyl and imidazolyl are independently selected from a $C_{1-4}$alkyl such as a methyl.

In another embodiment, $R^1$ is selected from:
(i) substituted or unsubstituted isoxazolyl;
(ii) substituted or unsubstituted furanyl; and
(iii) substituted or unsubstituted thiazolyl,
wherein the substituents for isooxazolyl, furanyl and thiazolyl are independently selected from a $C_{1-4}$alkyl such as a methyl.

In another embodiment, $R^1$ is selected from:

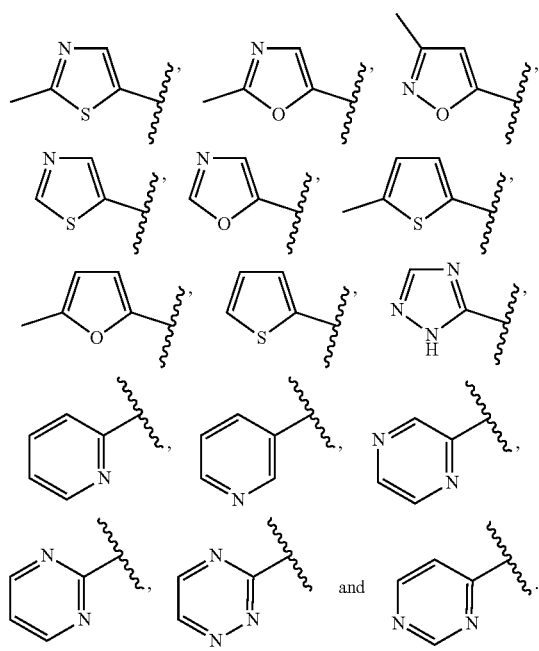

In an embodiment, X is absent or is selected from O, NH, $NC_{1-6}$alkyl, S, $C_{1-6}$alkylene, $C_{2-6}$alkenylene and $C_{2-6}$alkynylene. In another embodiment, X is absent. In a further embodiment, X is O or $C_{1-6}$alkylene. It is an embodiment that X is O. In another embodiment, X is $C_{1-6}$alkylene. In a further embodiment X is —$CH_2$—.

In an embodiment, X is O and $R^1$ is $C_{1-6}$alkyl. In another embodiment, X is O and $R^1$ is t-butyl.

In another embodiment, X is $C_{1-6}$alkylene and $R^1$ is $C_{3-8}$heterocycloalkyl. In a further embodiment, X is $C_{1-4}$alkylene and $R^1$ is a 6-membered heterocycloalkyl. It is an embodiment of the present application that X and $R^1$ together form the structure:

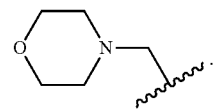

In other embodiments, X is absent and $R^1$ is substituted or unsubstituted heteroaryl, wherein the substituents for heteroaryl are independently selected from a $C_{1-4}$alkyl such as a methyl. It will be appreciated that in such embodiments of the present application, the heteroaryl embodiments can be as discussed above in respect of $R^1$.

In an embodiment, $R^2$, $R^3$ and $R^4$ are each independently selected from the group consisting of $C_{1-10}$alkyl, $C_{2-10}$alkenyl, $C_{2-10}$alkynyl, $C_{1-6}$alkylene$C_{6-14}$aryl, $C_{1-6}$alkylene-heteroaryl, $C_{1-6}$alkylene$C_{3-8}$cycloalkyl, $C_{1-6}$alkylene-O—$C_{1-6}$alkyl, $C_{1-6}$alkylene-O—$C_{1-6}$haloalkyl, $C_{2-6}$alkenylene-O—$C_{1-6}$haloalkyl and $C_{2-6}$alkynylene-O—$C_{1-6}$haloalkyl, wherein at least one of $R^2$, $R^3$ and $R^4$ is $C_{1-6}$-alkylene-O—$C_{1-6}$haloalkyl. In another embodiment, $R^2$, $R^3$ and $R^4$ are each independently selected from the group consisting of $C_{1-6}$alkyl, $C_{1-6}$alkylene$C_{6-10}$aryl, $C_{1-6}$alkylene-O—$C_{1-4}$alkyl and $C_{1-6}$alkylene-O—$C_{1-4}$fluoroalkyl, wherein at least one of $R^2$, $R^3$ and $R^4$ is $C_{1-6}$alkylene-O—$C_{1-4}$fluoroalkyl. In a further embodiment $R^2$, $R^3$ and $R^4$ are each independently selected from the group consisting of $C_{1-6}$alkyl, $C_{1-4}$alkylene-phenyl, $C_{1-4}$alkylene-O—$C_{1-4}$alkyl, $C_{1-4}$alkylene-O—$CH_2F$, $C_{1-4}$alkylene-O—$CHF_2$ and $C_{1-4}$alkylene-O—$CF_3$, wherein at least one of $R^2$, $R^3$ and $R^4$ is $C_{1-4}$alkylene-O—$CH_2F$, $C_{1-4}$alkylene-O—$CHF_2$ or $C_{1-4}$alkylene-O—$CF_3$. It is an embodiment that $R^2$, $R^3$ and $R^4$ are each independently selected from the group consisting of isobutyl, —$CH_2$-Ph, —$CH_2$—O—$CH_3$, —$CH_2$—O—$CH_2F$, —$CH_2$—O—$CHF_2$ and —$CH_2$—O—$CF_3$, wherein at least one of $R^2$, $R^3$ and $R^4$ is —$CH_2$—O—$CH_2F$, —$CH_2$—O—$CHF_2$ or —$CH_2$—O—$CF_3$. In another embodiment, $R^2$, $R^3$ and $R^4$ are each independently selected from the group consisting of isobutyl, —$CH_2$-Ph, —$CH_2$—O—$CH_3$ and —$CH_2$—O—$CHF_2$, wherein at least one of $R^2$, $R^3$ and $R^4$ is —$CH_2$—O—$CHF_2$.

In an embodiment, $R^2$ and $R^3$ are each independently selected from the group consisting of $C_{1-10}$alkyl, $C_{2-10}$alkenyl, $C_{2-10}$alkynyl, $C_{1-6}$alkylene-O—$C_{1-6}$alkyl, $C_{1-6}$alkylene-O—$C_{1-6}$haloalkyl, $C_{2-6}$alkenylene-O—$C_{1-6}$haloalkyl and $C_{2-6}$alkynylene-O—$C_{1-6}$haloalkyl, wherein at least one of $R^2$ and $R^3$ is $C_{1-6}$-alkylene-O—$C_{1-6}$haloalkyl. In another embodiment, $R^2$ and $R^3$ are each independently selected from the group consisting of $C_{1-6}$alkyl, $C_{1-6}$alkylene-O—$C_{1-4}$alkyl and $C_{1-6}$alkylene-O—$C_{1-4}$fluoroalkyl, wherein at least one of $R^2$ and $R^3$ is $C_{1-4}$alkylene-O—$C_{1-4}$fluoroalkyl.
In a further embodiment $R^2$ and $R^3$ are each independently selected from the group consisting of $C_{1-6}$alkyl, $C_{1-4}$alkylene-O—$C_{1-4}$alkyl, $C_{1-4}$ alkylene-O—$CH_2F$, $C_{1-4}$alkylene-O—$CHF_2$ and $C_{1-4}$alkylene-O—$CF_3$ wherein at least one of $R^2$ and $R^3$ is $C_{1-4}$alkylene-O—$CH_2F$, $C_{1-4}$alkylene-O—$CHF_2$ or $C_{1-4}$alkylene-O—$CF_3$. It is an embodiment that $R^2$ and $R^3$ are each independently selected from the group consisting of isobutyl, —$CH_2$—O—$CH_3$, $CH_2$—O—$CH_2F$, —CH$_2$—O—CHF$_2$ and —CH$_2$—O—CF$_3$, wherein at least one of R$^2$ and R$^3$ is —CH$_2$—O—CH$_2$F, —CH$_2$—O—CHF$_2$ or —CH$_2$—O—CF$_3$. In another embodiment, R$^2$ and R$^3$ are each independently selected from the group consisting of isobutyl, —CH$_2$—O—CH$_3$ and —CH$_2$—O—CHF$_2$, wherein at least one of R$^2$ and R$^3$ is —CH$_2$—O—CHF$_2$.

In an embodiment, R$^2$ and R$^3$ are each C$_{1-6}$alkylene-O—C$_{1-4}$ fluoroalkyl. In another embodiment, R$^2$ and R$^3$ are each C$_{1-4}$alkylene-O—CHF$_2$. In a further embodiment, R$^2$ and R$^3$ are each —CH$_2$—O—CHF$_2$.

In an embodiment, R$^4$ is selected from the group consisting of C$_{1-10}$alkyl, C$_{2-10}$alkenyl, C$_{2-10}$alkynyl, C$_{1-6}$alkyleneC$_{3-8}$cycloalkyl and C$_{1-6}$alkyleneC$_{6-14}$aryl. In another embodiment, R$^4$ is selected from the group consisting of C$_{1-6}$alkyl, C$_{1-6}$alkyleneC$_{3-8}$cycloalkyl, and C$_{1-6}$alkyleneC$_{6-10}$aryl. In a further embodiment, R$^4$ is selected from the group consisting of C$_{1-6}$alkyl and C$_{1-4}$alkylene-phenyl. It is an embodiment that R$^4$ is isobutyl or —CH$_2$-Ph. In an embodiment, R$^4$ is isobutyl. In another embodiment, R$^4$ is —CH$_2$-Ph.

In another embodiment, at least one of R$^2$ and R$^3$ or both is independently selected from the group consisting of C$_{1-6}$alkylene-O—CH$_2$F, C$_{1-6}$alkylene-O—CHF$_2$ and C$_{1-6}$alkylene-O—CF$_3$. In a further embodiment, at least one of R$^2$ and R$^3$ or both is —CH$_2$—O—CHF$_2$.

In another embodiment, R$^4$ is selected from C$_{1-6}$alkyl, C$_{1-6}$ alkyleneC$_{3-8}$cycloalkyl and C$_{1-6}$alkyleneC$_{6-14}$aryl, optionally substituted with one or more independently-selected groups R$^6$. In a further embodiment, R$^4$ is selected from —CH$_2$-phenyl-(CH$_2$)$_2$-phenyl, isobutyl, and tert-butyl. It is an embodiment that R$^4$ is —CH$_2$-phenyl or isobutyl.

In an embodiment, R$^5$ is selected from the group consisting of H, C$_{1-6}$alkyl, C$_{2-6}$alkenyl and C$_{2-6}$alkynyl. In another embodiment, R$^5$ is C$_{1-6}$alkyl. In a further embodiment, R$^5$ is C$_{1-4}$alkyl. It is an embodiment that R$^5$ is methyl.

In an embodiment, R$^6$ is selected from the group consisting of C$_{1-4}$alkyl, OH, C$_{1-4}$alkoxy, C$_{6-10}$aryloxy, —NH—C$_{1-4}$ alkyl, —N(C$_{1-4}$alkyl)$_2$, C$_{1-4}$alkylene-N(C$_{1-4}$alkyl)$_2$, C$_{1-4}$alkylene-NH—C$_{1-4}$alkyl, C$_{3-8}$cycloalkyl, heterocycloalkyl, C$_{6-10}$aryl and a 5- or 6-membered heteroaryl. In another embodiment, R$^6$ is selected from the group consisting of C$_{1-4}$alkyl, OH, C$_{1-4}$alkoxy, —NH—C$_{1-4}$alkyl and —N(C$_{1-4}$alkyl)$_2$.

In an embodiment, R$^7$ and R$^8$ are each independently selected from the group consisting of H, C$_{1-4}$alkyl, C$_{1-4}$haloalkyl, C$_{2-4}$alkenyl, C$_{2-4}$alkynyl, C$_{3-8}$cycloalkyl, C$_{1-4}$alkylene-C$_{3-8}$cycloalkyl, heterocycloalkyl, C$_{6-10}$aryl, C$_{1-4}$alkylene-C$_{6-10}$aryl, C$_{1-4}$alkylene-heterocycloalkyl, heteroaryl, and C$_{1-4}$alkylene-heteroaryl, wherein any cyclic moiety is optionally fused to a further 5- to 7-membered heterocycloalkyl.

In an embodiment, the compounds of Formula I have the following relative stereochemistry:

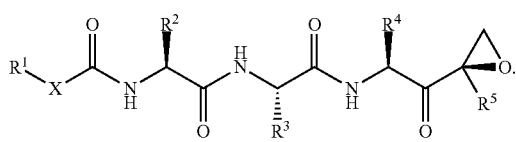

I

In an embodiment, the compound of the present application is selected from the compounds of Examples 1 to 33 as illustrated below or a pharmaceutically acceptable salt, solvate or prodrug thereof:

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

2-Methyl-thiazole-5-carboxylic acid-((S)-1-{(S)-1-[(S)-1-benzyl-2-((R)-2-methyloxiranyl)-2-oxo-ethylcarbamoyl]-2-methoxy-ethylcarbamoyl}-2-difluoromethoxyethyl)-amide;

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-methoxyethyl)-amide;

2-Methyl-oxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

3-Methyl-isoxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Thiazole-5-carboxylic acid ((S)-1-{(S)-1-[(S)-1-benzyl-2-((R)-2-methyloxiranyl)-2-oxoethylcarbamoyl]-2-difluoromethoxyethylcarbamoyl}-2-difluoromethoxyethyl) amide;

Oxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

5-Methyl-thiophene-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

5-Methyl-furan-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Thiophene-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N-[(1S)-2-[[(1S)-2-[[(1S)-1-benzyl-2-[(2R)-2-methyloxiran-2-yl]-2-oxo-ethyl]amino]-1-(difluoromethoxymethyl)-2-oxo-ethyl]amino]-1-(difluoromethoxymethyl)-2-oxo-ethyl]-1H-1,2,4-triazole-5-carboxamide;

N-[(1S)-1-(difluoromethoxymethyl)-2-[[(1S)-1-(difluoromethoxymethyl)-2-[[(1S)-3-methyl-1-[(2R)-2-methyloxirane-2-carbonyl]butyl]-amino]-2-oxo-ethyl]amino]-2-oxo-ethyl]-2-methyl-thiazole-5-carboxamide;

Pyridine-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N—((S)-1-{(S)-1-[(S)-1-Benzyl-2-((R)-2-methyl-oxiranyl)-2-oxo-ethylcarbamoyl]-2-difluoromethoxyethylcarbamoyl}-2-difluoromethoxyethyl)-nicotinamide;

Pyridine-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N-[(1S)-2-[[(1S)-2-[[(1S)-1-benzyl-2-[(2R)-2-methyloxiran-2-yl]-2-oxo-ethyl]amino]-1-(difluoromethoxymethyl)-2-oxo-ethyl]amino]-1-(difluoromethoxymethyl)-2-oxo-ethyl]-pyrimidine-2-carboxamide;

[1,2,4]Triazine-3-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Pyrimidine-4-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

2-Methyl-thiazole-5-carboxylic acid ((S)-1-{(S)-1-[(S)-1-benzyl-2-((R)-2-methyloxiranyl)-2-oxo-ethylcarbamoyl]-3-methylbutylcarbamoyl}-2-difluoromethoxyethyl)-amide;

2-Methyl-thiazole-5-carboxylic acid ((S)-2-difluoromethoxy-1-{(S)-3-methyl-1-[(S)-3-methyl-1-((R)-2-methyloxiranecarbonyl)-butylcarbamoyl]-butylcarbamoyl}-ethyl)-amide, 2-Methyl-thiazole-5-carboxylic acid ((S)-1-{(S)-2-difluoromethoxy-1-[(S)-3-methyl-1-((R)-2-methyloxiranecarbonyl)-butylcarbamoyl]-ethylcarbamoyl}-3-methylbutyl)-amide;

2-Methyl-thiazole-5-carboxylic acid ((S)-1-{(S)-1-[(5)-1-benzyl-2-((R)-2-methyloxiranyl)-2-oxo-ethylcarbamoyl]-2-difluoromethoxyethylcarbamoyl}-3-methylbutyl)-amide;

2-Methyl-thiazole-5-carboxylic acid ((S)-1-{(S)-2-difluoromethoxy-1-[(S)-3-methyl-1-((R)-2-methyloxiranecarbonyl)-butylcarbamoyl]-ethylcarbamoyl}-2-phenyl-ethyl)-amide;

2-Methyl-thiazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-phenylethyl)-amide;

2S)-2-[[(2S)-3-(difluoromethoxy)-2-[(2-morpholinoacetyl)amino]propanoyl]amino]-N-[(1S)-3-methyl-1-[(2R)-2-methyloxirane-2-carbonyl]butyl]-3-phenylpropanamide;

(S)—N—{(S)-1-[(S)-1-Benzyl-2-((R)-2-methyloxiranyl)-2-oxo-ethylcarbamoyl]-2-difluoromethoxyethyl}-3-difluoromethoxy-2-(2-morpholin-4-yl-acetylamino)-propionamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-4-methylpentanamide;

(2S)-2-[[(2S)-3-(difluoromethoxy)-2-[(2-morpholinoacetyl)amino]propanoyl]amino]-4-methyl-N-[(1S)-3-methyl-1-[(2R)-2-methyloxirane-2-carbonyl]butyl]pentanamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-3-(1-methylcyclohexa-1,3,5-trien-1-yl)propanamide;

(S)-4-Methyl-2-(2-morpholin-4-yl-acetylamino)-pentanoic acid {(S)-2-difluoromethoxy-1-[(S)-3-methyl-1-((R)-2-methyloxiranecarbonyl)-butylcarbamoyl]-ethyl}-amide;

(S)-4-Methyl-2-(2-morpholin-4-yl-acetylamino)-pentanoic acid {(S)-1-[(S)-1-benzyl-2-((R)-2-methyloxiranyl)-2-oxo-ethylcarbamoyl]-2-difluoromethoxyethyl}-amide;

(2S)—N-[(1S)-2-[[(1S)-1-benzyl-2-[(2R)-2-methyloxiran-2-yl]-2-oxo-ethyl]amino]-1-(difluoromethoxymethyl)-2-oxo-ethyl]-2-[(2-morpholinoacetyl)amino]-3-phenylpropanamide; and (2S)-3-(difluoromethoxy)-N-[(1S)-1-(difluoromethoxymethyl)-2-[[(1S)-3-methyl-1-[(2R)-2-methyloxirane-2-carbonyl]butyl]amino]-2-oxo-ethyl]-2-[(2-morpholinoacetyl)amino]-propanamide.

In another embodiment, the compound of the present application is selected from:

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

(2S)-2-[[(2S)-3-(difluoromethoxy)-2-[(2-morpholinoacetyl)amino]propanoyl]amino]-N-[(1S)-3-methyl-1-[(2R)-2-methyloxirane-2-carbonyl]butyl]-3-phenyl-propanamide;

(S)—N—{(S)-1-[(S)-1-benzyl-2-((R)-2-methyl-oxiranyl)-2-oxo-ethylcarbamoyl]-2-difluoromethoxyethyl}-3-difluoromethoxy-2-(2-morpholin-4-yl-acetylamino)-propionamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-4-methylpentanamide;

(2S)-2-[[(2S)-3-(difluoromethoxy)-2-[(2-morpholinoacetyl)amino]propanoyl]amino]-4-methyl-N-[(1S)-3-methyl-1-[(2R)-2-methyloxirane-2-carbonyl]butyl]pentanamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-3-(1-methylcyclohexa-1,3,5-trien-1-yl)propanamide; and (2S)-3-(difluoromethoxy)-N-[(1S)-1-(difluoromethoxymethyl)-2-[[(1S)-3-methyl-1-[(2R)-2-methyloxirane-2-carbonyl]butyl]amino]-2-oxo-ethyl]-2-[(2-morpholinoacetyl)amino]propanamide.

In another embodiment, the compound of the present application is 2-methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide.

In an embodiment, the present application also includes a compound of Formula (I):

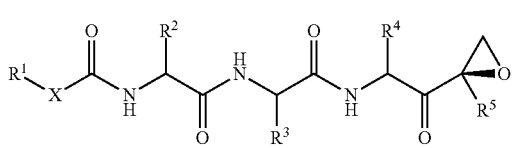

Formula (I)

wherein:

$R^1$ is selected from the group consisting of $C_{1-6}$-alkyl, $C_{1-6}$-alkyloxy, $C_{1-6}$-alkyloxyoalkyl, $C_{1-6}$-alkenyloxyhaloalkyl, $C_{1-6}$-alkynyloxyhaloalkyl, $C_{1-6}$-alkylhalo, $C_{2-6}$-alkenyl, $C_{2-6}$-alkynyl, $C_{3-8}$-cycloalkyl, $C_{1-6}$-alkyl-$C_{3-8}$-cycloalkyl, aryl, heteroaryl, $C_{1-6}$-alkylaryl, $C_{1-6}$-alkylheteroaryl, $C_{1-6}$-alkylheterocycloalkyl, C(O)H, (CO)$R^7$, O(CO)$R^7$, C(O)O$R^7$, $C_{1-6}$-alkylO$R^7$, $C_{1-6}$-alkyl(CO)$R^7$, $C_{0-6}$-alkylCO$_2$$R^7$, $C_{1-6}$-alkylcyano, $C_{1-6}$-alkylN$R^7$$R^8$, $C_{1-6}$-alkyl(CO)N$R^7$$R^8$, $C_{1-6}$-alkylN$R^6$(CO)$R^8$, $C_{1-6}$-alkylN$R^7$(CO)N$R^7$$R^8$, $C_{1-6}$-alkylS$R^7$, $C_{1-6}$-alkyl(SO)$R^7$, $C_{1-6}$-alkylSO$_2$$R^6$, $C_{1-6}$-alkyl(SO$_2$)N$R^7$$R^8$, $C_{1-6}$-alkylN$R^7$(SO$_2$)$R^8$, $C_{1-6}$-alkylN$R^7$(SO$_2$)N$R^7$$R^8$, (CO)N$R^7$$R^8$, $C_{1-6}$-alkylN$R^7$(CO)O$R^8$, and a 3- to 7-membered ring that may contain one or more heteroatoms independently selected from the group consisting of N, O and S, wherein any cyclic moiety is optionally fused to a 5- to 7-membered ring that may contain one or more heteroatoms independently selected from the group consisting of N, O and S;

X is selected from the group consisting of hydrogen, carbon, oxygen, nitrogen, sulfur, $C_{1-6}$-alkyl, $C_{1-6}$-alkyloxy, $C_{1-6}$-alkyloxyoalkyl, $C_{1-6}$-alkenyloxyaminoalkyl, $C_{1-6}$-alkynyloxyhaloalkyl, $C_{1-6}$-alkylhalo, $C_{2-6}$-alkenyl, $C_{2-6}$-alkynyl, $C_{3-8}$-cycloalkyl, $C_{1-6}$-alkyl-$C_{3-8}$-cycloalkyl, aryl, heteroaryl, $C_{1-6}$-alkylaryl, $C_{1-6}$-alkylheteroaryl, $C_{1-6}$-alkylheterocycloalkyl;

$R^2$, $R^3$ and $R^4$, are selected from the group consisting of $C_{1-6}$-alkyl, $C_{1-6}$-alkyloxy, $C_{1-6}$-alkyloxyoalkyl, $C_{1-6}$-alkenyloxyhaloalkyl, $C_{1-6}$-alkynyloxyhaloalkyl, $C_{1-6}$-alkylhalo, $C_{2-6}$-alkenyl, $C_{2-6}$-alkynyl, $C_{3-8}$-cycloalkyl, $C_{1-6}$-alkyl-$C_{3-8}$-cycloalkyl, aryl, heteroaryl, $C_{1-6}$-alkylaryl, $C_{1-6}$-alkyl-heteroaryl, $C_{1-6}$-alkylheterocycloalkyl, C(O)H, (CO)$R^7$, O(CO)$R^7$, C(O)O$R^7$, $C_{1-6}$-alkylO$R^7$, $C_{1-6}$-alkyl(CO)$R^7$, $C_{0-6}$-alkylCO$_2R^7$, $C_{1-6}$-alkylcyano, $C_{1-6}$-alkylN$R^7R^8$, $C_{1-6}$-alkyl(CO)N$R^7R^8$, $C_{1-6}$-alkylN$R^6$(CO)$R^8$, $C_{1-6}$-alkylN$^7$(CO)N$R^7R^8$, $C_{1-6}$-alkylS$R^7$, $C_{1-6}$-alkyl(SO)$R^7$, $C_{1-6}$-alkylSO$_2R^6$, $C_{1-6}$-alkyl(SO$_2$)N$R^7R^8$, $C_{1-6}$-alkyl N$R^7$(SO$_2$)$R^8$, $C_{1-6}$-alkylN$R^7$(SO$_2$)N$R_7R_8$, (CO)N$R^7R^8$, $C_{1-6}$-alkylN$R^7$(CO)O$R^8$, and a 3- to 7-membered ring that may contain one or more heteroatoms independently selected from the group consisting of N, O and S, wherein any cyclic moiety is optionally fused to a 5- to 7-membered ring that may contain one or more heteroatoms independently selected from the group consisting of N, O and S; with the proviso that at least $R^2$, $R^3$ or $R^4$ is $C_{1-6}$-alkyloxyhaloalkyl, optionally substituted with one or more independently-selected groups $R^6$; and cannot simultaneously be $C_{1-6}$-alkyloxyoalkyl;

$R^5$, is selected from the group consisting of H, $C_{1-6}$-alkyl, $C_{1-6}$ alkylhalo $C_{2-6}$-alkenyl, $C_{2-6}$-alkynyl, $C_{3-6}$-cycloalkyl, $C_{1-6}$-alkyl-$C_{3-8}$-cycloalkyl, aryl, heteroaryl, and a 3- to 7-membered ring that may contain one or more heteroatoms independently selected from the group consisting of N, O and S;

$R^6$ is selected from the group consisting of H, F, Cl, Br, I, OH, —O—(CH$_2$)$_{2,3}$—O—, OC$_{1-6}$ alkyl, OC$_{1-6}$-aryl, NH—C$_{1-6}$-alkyl, and N(C$_{1-6}$-alkyl)$_2$, $C_{1-6}$-alkyl-N(C$_{1-6}$-alkyl)$_2$, cycloalkyl, heterocycloalkyl, aryl and heteroaryl;

$R^7$ and $R^8$ are independently selected from the group consisting of H, $C_{1-6}$-alkyl, $C_{1-6}$-alkylhalo, $C_{2-6}$-alkenyl, $C_{2-6}$-alkynyl, $C_{3-8}$-cycloalkyl, $C_{1-6}$alkyl-$C_{3-8}$-cycloalkyl, cycloalkyl, aryl, $C_{1-6}$-alkylaryl, $C_{0-6}$-alkylheterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S.

In an embodiment, X is $C_{0-7}$ alkyl and $R^1$ is a 5- or -6 membered heteroaryl and acyclic and 3-7-membered amine.

In another embodiment, X is $C_{0-7}$ alkyl, $R^1$ is selected from morpholine, 1,4-oxazepane, thiomorpholine, 1,4-thiazepane, 1,4-thiazepane 1-oxide, 1,4-thiazepane 1,1-dioxide, 1,4-thiazinane 1-oxide, 1,4-thiazinane 1,1-dioxide, aziridine, azetidine, pyrrolidine, piperazine and 1,4-diazepane, oxadiazole isoxazole, isothiazole, furan, thiophene, oxazole, thiazole, pyrazole, and imidazole.

In another embodiment, at least one of $R^2$, $R^3$ or $R^4$ is selected from $C_{1-6}$ alkoxyhaloalkyl, in a further certain aspect, at least one of $R^2$, $R^3$ and $R^4$ or all is selected from mono-fluoromethyl, di-fluoromethyl and tri-fluoromethyl moiety groups.

In another embodiment, at least one of $R^2$ and $R^3$ is selected from $C_{1-6}$-alkoxyhaloalkyl, in a further certain aspect, at least one of $R^2$ and $R^3$ or both are selected from di-fluoromethyl, moiety.

In another embodiment, $R^4$ is selected from $C_{1-6}$ alkyl, $C_{1-6}$ alkyl, $C_{1-6}$ alkylcycloalkyl and $C_{1-6}$ alkylaryl. In certain such embodiment, $R^4$ is selected from phenylmethyl, phenyl-ethyl, 2-methyl-butanyl, 2,2-dimethyl-butanyl, preferably phenyl-methyl and 2-Methyl-butanyl.

III. Preparation of Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art.

In an embodiment, the compounds of Formula I are generally prepared according to the process illustrated in Scheme I. Variables in the following schemes are as defined above for Formula I unless otherwise specified.

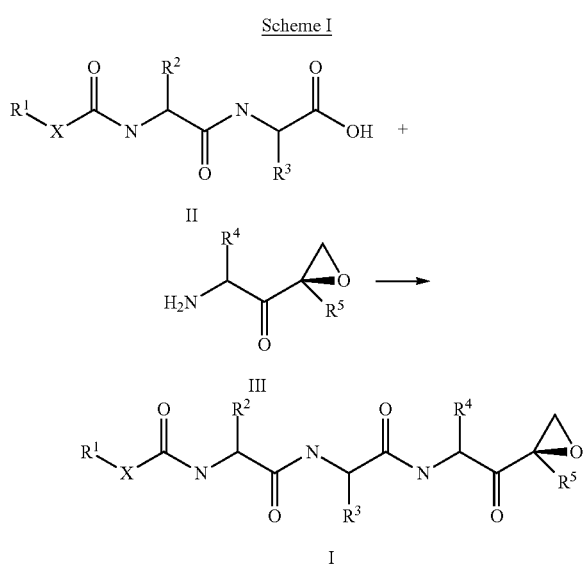

Scheme I

In an embodiment, as shown in Scheme 1, the compounds of the present application are prepared by coupling of a dipeptide of Formula II with an epoxyketone of Formula III via the formation of a peptide bond. Methods for coupling compounds through peptide (amide) bonds are well known in the art and described, for example, in *The Peptides*: Analysis, Synthesis, Biology, Vol. I., eds. Academic Press, 1979.

In an embodiment, the intermediate compound of Formula II is prepared according to standard procedures for peptide bond formation as illustrated in Scheme II, wherein the compounds of Formula IV and V are coupled via amide bond formation. For example, the compounds of Formula IV (wherein $R^1$ is optionally a protecting group, such as Boc or Cbz) and Formula V (wherein A is, for example an alkyl or benzyl group) are obtained from commercial sources or prepared by methods known in the art. Examples of the dipeptide of Formula II are provided in specific examples described below.

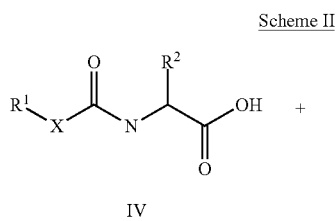

Scheme II

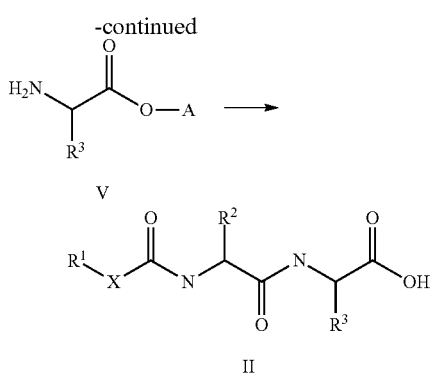

In an embodiment, epoxyketones of Formula III are prepared as illustrated in Scheme III using modified literature methods [see, for example, *Bioorg. Med. Chem. Lett.* 2007, 17, 6169-6171; *Bioorg. Med. Chem. Lett* 1999, 9, 2283-2288; *Eur. J. Org. Chem.* 2005, 4829-4834; and *J. Med. Chem.* 2009, 52, 3028-3038].

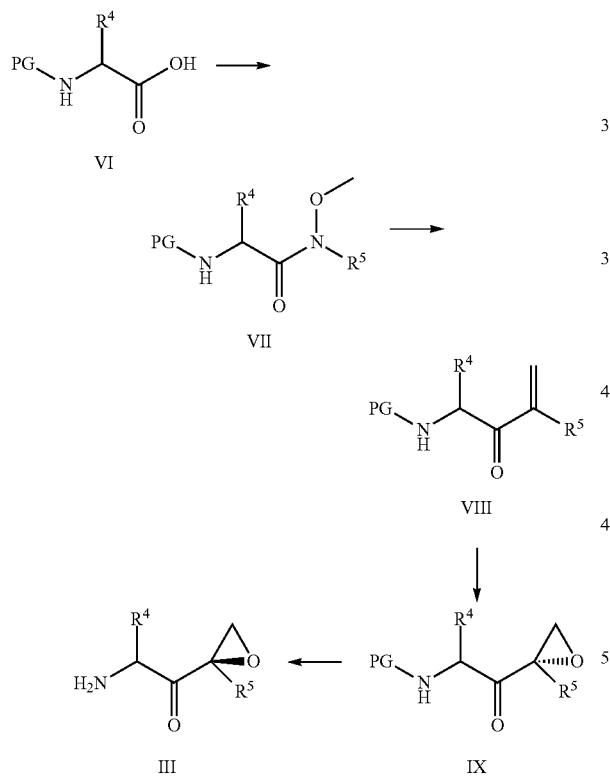

As shown in Scheme III, epoxyketone compounds of Formula III, in one embodiment, are prepared from a protected amino acid of Formula VI which is transformed to the corresponding Weinreb amide of Formula VII [see, for example, *Synthesis* 1983, 676; *Bioorg. Med. Chem. Lett.* 1999, 2283-2288], followed by an appropriate lithium, zinc or Grignard reagent condensation leading to the unsaturated ketone of Formula VIII. Subsequent epoxidation with alkaline hydrogen peroxide provides epoxide derivatives of Formula IX as a mixture of diastereomers, which are readily separated by column chromatography. Removal of the protecting group (PG) by a suitable method such as a hydrogenolysis reaction (for example, wherein PG is a Cbz group) or hydrolysis in acidic conditions (for example, wherein PG is a Boc protecting group), gives the epoxides of Formula III in salt form, such as a salt of TEA.

In an alternative embodiment, according to Scheme IV, epoxyketone intermediates of Formula III are prepared from an unsaturated ketone of Formula VIII, which is reduced to the corresponding allylic alcohol of Formula X. Subsequently, Sharpless asymmetric epoxidation leads to hydroxyl-ketone compounds of Formula XI which are oxidized to provide epoxyketone intermediates of Formula IX, which are subsequently hydrolyzed to provide intermediate compounds of Formula III [see, for example, *J. Med. Chem.* 2009, 52, 3028-3038; *Tetrahedron: Asymmetry* 2001, 12, 943-947].

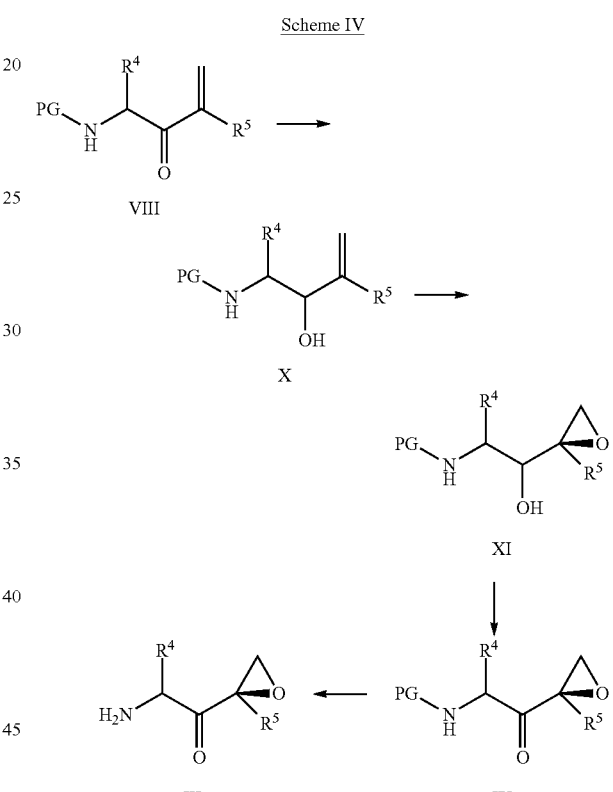

In an embodiment, as a representative example of the incorporation of a $C_{1-6}$alkylene-O—$C_{1-6}$haloalkyl group in $R^2$, $R^3$ and/or $R^4$ of the compounds of the application, a precursor compound to the compounds of Formula I, for example a compound of the Formula II, III, IV or V, or protected forms thereof, wherein $R^2$, $R^3$ and/or $R^4$ is $C_{1-6}$alkylene-OH is reacted with, for example, 2-fluorosulfonyldifluoroacetic acid in the presence of a metal catalyst, such as copper (I) iodide, under conditions to covert the $C_{1-6}$alkylene-OH to $C_{1-6}$alkylene-OCHF$_2$. A person skilled in the art would know other methods of functionalizing the $C_{1-6}$alkylene-OH group with alternative $C_{1-6}$haloalkyl group using methods and reagents available in the art.

Another aspect of the present application provides processes for preparing compounds of Formula I, or salts, solvates or prodrugs thereof. Processes for the preparation of the compounds in the present application are described herein.

Accordingly, the present application includes a method for preparing a compound of Formula I comprising reacting a compound of a Formula II with a compound of a Formula III:

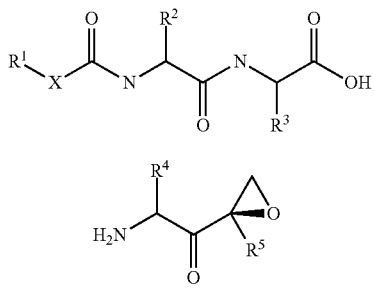

Wherein $R^1$, $R^2$, $R^3$, $R^4$ and $R^5$ are as defined above for the compounds of Formula I, or are protected forms thereof, under conditions for the formation of an amide bond; and removal of protecting groups if present.

In another embodiment, the compounds of Formula II are prepared by reacting a compound of the Formula VIII:

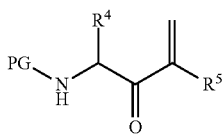

wherein PG is a protecting group and $R^4$ and $R^5$ are as defined above for the compounds of Formula I, or are protected forms thereof, under conditions for the epoxidation of the double bond followed by removal of protecting groups.

In an alternative embodiment, the compounds of Formula II are prepared by reacting a compound of the Formula VIII:

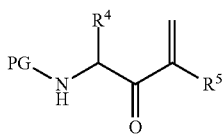

wherein PG is a protecting group and $R^4$ and $R^5$ are as defined above for the compounds of Formula I, or are protected forms thereof,
under conditions for the reduction of the ketone to the corresponding alcohol, followed by epoxidation of the double bond, followed by oxidation of the alcohol and then removal of protecting groups.

In addition, it is intended that the present application cover compounds made either using standard organic synthetic techniques, including combinatorial chemistry or by biological methods, such as bacterial digestion, metabolism, enzymatic conversion, and the like.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

IV. Compositions

The compounds of the present application are suitably formulated in a conventional manner into compositions using one or more carriers. Accordingly, the present application also includes a composition comprising one or more compounds of the application and a carrier. In another embodiment, the compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds of the application are administered to a subject in a variety of forms depending on the selected route of administration, as will be understood by those skilled in the art. A compound of the application is administered, for example, by oral, parenteral, buccal, sublingual, nasal, rectal, patch, pump or transdermal administration and the pharmaceutical compositions formulated accordingly. In an embodiment, administration is by means of a pump for periodic or continuous delivery.

Parenteral administration includes intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. In an embodiment, parenteral administration is by continuous infusion over a selected period of time. Conventional procedures and ingredients for the selection and preparation of suitable compositions are described, for example, in Remington's Pharmaceutical Sciences (2000-

20th edition) and in The United States Pharmacopeia: The National Formulary (USP 24 NF19) published in 1999.

In an embodiment, a compound of the application is orally administered, for example, with an inert diluent or with an assimilable edible carrier, or it is enclosed in hard or soft shell gelatin capsules, or it may be compressed into tablets, or it is incorporated directly with the food of the diet. In a further embodiment, for oral therapeutic administration, the compound is incorporated with excipient and used in the form of ingestible tablets, buccal tablets, troches, capsules, caplets, pellets, granules, lozenges, chewing gum, powders, syrups, elixirs, wafers, aqueous solutions or suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In an embodiment, the tablets are coated by methods well known in the art. In the case of tablets, capsules, caplets, pellets or granules for oral administration, pH sensitive enteric coatings, such as Eudragits™, designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for e.g. in liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of phospholipids, such as cholesterol, stearylamine or phosphatidylcholines. For oral administration in a capsule form, useful carriers or diluents include lactose and dried corn starch.

Liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and/or preservatives (e.g., methyl or propyl p-hydroxybenzoates or sorbic acid). Useful diluents include lactose and/or high molecular weight polyethylene glycols.

It is also possible to freeze-dry the compounds of the application and use the lyophilizates obtained, for example, for the preparation of products for injection.

In a further embodiment, a compound of the application is administered parenterally. For example, solutions of a compound of the application are prepared in water suitably mixed with a surfactant such as hydroxypropylcellulose. Dispersions are also prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are, for example, delivered by ocular delivery systems known to the art such as applicators or eye droppers. In an embodiment, such compositions include mucomimetics such as hyaluronic acid, chondroitin sulfate, hydroxypropyl methylcellulose and/or polyvinyl alcohol, preservatives such as sorbic acid, EDTA and/or benzyl chromium chloride, and the usual quantities of diluents or carriers. For pulmonary administration, diluents and/or carriers will be selected to be appropriate to allow the formation of an aerosol.

In a further embodiment, the compounds of the application are formulated for parenteral administration by injection, including using conventional catheterization techniques or infusion. Formulations for injection are, for example, presented in unit dosage form, e.g., in ampoules or in multidose containers, with an added preservative. In an embodiment, the compositions take such forms as sterile suspensions, solutions or emulsions in oily or aqueous vehicles, and, optionally contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In an embodiment, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In an embodiment, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. In an embodiment, the aerosol dosage forms also take the form of a pump-atomizer.

Compositions suitable for buccal or sublingual administration include tablets, lozenges, and pastilles, wherein the active ingredient is formulated with a carrier such as sugar, acacia, tragacanth, and/or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and/or fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

In an embodiment, compounds of the application are coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, compounds of the application are coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application including pharmaceutically acceptable salts, solvates and prodrugs thereof are suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

Compounds of the application are used alone or in combination with other known agents useful for treating diseases, disorders or conditions mediated by proteasome inhibition. When used in combination with other agents useful in treating diseases, disorders or conditions mediated by proteasome inhibition, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising a compound of Formula I, an additional therapeutic agent, and a pharmaceutically acceptable carrier.

The dosage of compounds of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In an embodiment, compounds of the application are administered initially in a suitable dosage that is optionally adjusted as required, depending on the clinical response. Dosages will generally be selected to maintain a serum level of compounds of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. In an embodiment of the application, compositions are formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In an embodiment, compounds of the application are administered in a single daily dose or the total daily dose is divided into two, three, four or more daily doses.

V. Methods and Uses of the Application

The compounds of the application have been shown to be capable of inhibiting proteasome activity.

Accordingly, the present application includes a method for inhibiting proteasome in a cell, either in a biological sample or in a patient, comprising administering an effective amount of one or more compounds of the application to the cell. The application also includes a use of one or more compounds of the application for inhibition of proteasome in a cell as well as a use of one or more compounds of the application for the preparation of a medicament for inhibition of proteasome in a cell. The application further includes one or more compounds of the application for use in inhibiting proteasome in a cell.

As the compounds of the application have been shown to be capable of inhibiting proteasome activity, the compounds of the application are useful for treating diseases, disorders or conditions mediated by proteasome inhibition. Therefore the compounds of the present application are useful as medicaments. Accordingly, the present application includes a compound of the application for use as a medicament.

The present application also includes a method of treating a disease, disorder or condition that is mediated by proteasome inhibition comprising administering a therapeutically effective amount of one or more compounds of the application to a subject in need thereof.

The present application also includes a use of one or more compounds of the application for treatment of a disease, disorder or condition mediated by proteasome inhibition as well as a use of one or more compounds of the application for the preparation of a medicament for treatment of a disease, disorder or condition mediated by proteasome inhibition. The application further includes one or more compounds of the application for use in treating a disease, disorder or condition mediated by proteasome inhibition.

In an embodiment, the disease, disorder or condition mediated by proteasome inhibition is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Compounds of the application have been demonstrated to be effective against the cell lines of a 60 human tumor cell line panel. Therefore in another embodiment of the present application, the disease, disorder or condition mediated by proteasome inhibition is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from a cancer of the skin, blood, prostate, colorectum, pancreas, kidney, ovary, breast, for example mammary, liver, tongue and lung. In another embodiment, the cancer is selected from leukaemia, lymphoma, non-Hodgkin's lymphoma and multiple myeloma. In a further embodiment of the present application, the cancer is selected from leukemia, melanoma, lung cancer, colon cancer, brain cancer, ovarian cancer, breast cancer, prostate cancer and kidney cancer.

In an embodiment, the disease, disorder or condition mediated by proteasome inhibition is a disease, disorder or condition associated with an uncontrolled and/or abnormal cellular activity affected directly or indirectly by proteasome inhibition. In another embodiment, the uncontrolled and/or abnormal cellular activity that is affected directly or indirectly by proteasome inhibition is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities affected directly or indirectly by proteasome inhibition in a cell, either in a biological sample or in a subject, comprising administering an effective amount of one or more compounds of the application to the cell. The application also includes a use of one or more compounds of the application for inhibition of uncontrolled and/or abnormal cellular activities affected directly or indirectly by proteasome inhibition in a cell as well as a use of one or more compounds of the application for the preparation of a medicament for inhibition of uncontrolled and/or abnormal cellular activities affected directly or indirectly by proteasome inhibition in a cell. The application further includes one or more compounds of the application for use in inhibiting uncontrolled and/or abnormal cellular activities affected directly or indirectly by proteasome inhibition in a cell.

The administration of the compound of Example 1 of the present application in combination with either bortezomib or dexamethasone has been demonstrated herein to be capable of being synergistic. Accordingly, the present application also includes a method of treating a disease, disorder or condition that is mediated by proteasome inhibition comprising administering a therapeutically effective amount of one or more compounds of the application in combination with another known agent useful for treatment of a disease, disorder or condition mediated by proteasome inhibition to a subject in need thereof. The present application also includes a use of one or more compounds of the application in combination with another known agent useful for treatment of a disease, disorder or condition mediated by proteasome inhibition for treatment of a disease, disorder or condition mediated by proteasome inhibition as well as a use of one or more compounds of the application in combination with another known agent useful for treatment of a disease, disorder or condition mediated by proteasome inhibition for the preparation of a medicament for treatment of a disease, disorder or condition mediated by proteasome inhibition. The application further includes one or more compounds of the application in combination with another known agent useful for treatment of a disease, disorder or condition mediated by proteasome inhibition for use in treating a disease, disorder or condition mediated by proteasome inhibition. In an embodiment, the disease, disorder or condition mediated by proteasome inhibition is cancer such as multiple myeloma. In another embodiment, the other known agent useful for treatment of a disease, disorder or condition mediated by proteasome inhibition is bortezomib or dexamethasone.

In a further embodiment, the disease, disorder or condition mediated by proteasome inhibition is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

The present application also includes a method of inhibiting the degradation of a protein by a proteasome capable of degrading the protein, comprising contacting the proteasome with an effective amount of one or more compounds of the application. The present application further includes a use of one or more compounds of the application for inhibition of the degradation of a protein by a proteasome capable of degrading the protein as well as a use of one or more compounds of the application for preparation of a medicament for inhibition of the degradation of a protein by a proteasome capable of degrading the protein. The present application also includes one or more compounds of the application for inhibiting the degradation of a protein by a proteasome capable of degrading the protein.

In an embodiment, the protein is marked with ubiquitin. In another embodiment, the protein is p53.

The present application also includes a method of treating accelerated and/or enhanced proteolysis, comprising administering a therapeutically effective amount of one or more compounds of the application to a subject in need thereof. The present application further includes a use of one or more compounds of the application for treatment of accelerated and/or enhanced proteolysis as well as a use of one or more compounds of the application for the preparation of a medicament for treatment of accelerated and/or enhanced proteolysis. The present application also includes one or more compounds of the application for treating accelerated and/or enhanced proteolysis. In an embodiment, the subject is a mammal having or predisposed to accelerated and/or enhanced proteolysis.

In another embodiment of the present application, the disease, disorder or condition mediated by proteasome inhibition is selected from a disease, disorder or condition associated with the cell cycle, Endoplasmic Reticulum Associated Protein Degradation, transcription factor regulation, gene expression, cell differentiation, the immune response, angiogenesis and the regulation or induction of apoptosis.

In another embodiment of the present application, the disease, disorder or condition mediated by proteasome inhibition is selected from viral infection, an inflammatory disease, an autoimmune disease, heart disease, an age-related eye disease and a neurodegenerative disease.

In another embodiment of the present application, the disease, disorder or condition mediated by proteasome inhibition is selected from HIV infection, type-1 diabetes, type-2 diabetes, allergic reactions, asthma, inflammatory arthritis, rheumatoid arthritis, osteoporosis, osteoarthritis, psoriasis, seronegative spondyloarthopathies, ankylosing spondylitis, systemic lupus erythematosus (SLE), autoimmune thyroid disease, congestive heart failure, pressure-overload cardiac hypertrophy, viral myocarditis, myocardial ischemic injury, heart disease, artherogenesis, atherosclerosis, cardiac events in diabetes, vascular disorders in diabetes, muscle wasting, obesity, Alzheimer's disease, Parkinson's disease, Huntington's disease, amyotrophic lateral sclerosis, autoimmune thyroid disease, cachexia, Crohn's disease, inflammatory bowel disease, sepsis, hepatitis B, transplantation rejection and related immunology, retina degeneration, cataracts and glaucoma.

In a further embodiment, the compounds of the application are used for treating a disease or disorder associated with inflammation in humans as well as other mammals. Exemplary inflammatory conditions include, but not limited to rheumatoid, arthritis, multiple sclerosis, degenerative joint disease, spondouloarthropathies, osteoporosis, diabetes, Alzheimer's disease, Parkinson's disease, shock, among others.

In a further embodiment, the compounds of the application are used for treating a disease or disorder selected from allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In a further embodiment, the compounds of the application are used for treating a disease or disorder selected from viral infections (HIV-1 and HIV-2), osteoporosis, osteoarthritis, psoriasis, restenosis heart disease, diabetes-associated cardiovascular disorders, inflammatory bowel disease, inflammatory and autoimmune diseases (arthritis, psoriasis), seronegative spondyloarthropathies (SpA), muscle wasting, obesity, allergy and asthma, neurodegenerative disorders, including Alzheimer's (AD) and Parkinson's (PD) diseases, and autoimmune diseases in a mammal having or predisposed to said disease or disorder.

The introduction of a halogen atom into a molecule also provides the opportunity for the use of the molecule in radiolabeling applications. For example, $^{18}$F is used as a radiolabel tracer in the sensitive technique of Positron Emission Tomography (PET). Accordingly the present application also includes methods of using the compounds of Formula I for diagnostic and imaging purposes, wherein the compounds of Formula I comprise at least one radiolabel, such as $^{18}$F.

Therefore the present application includes the use of one of more compounds of the application for radiolabel imaging, wherein the compounds of the application comprise at least one radiolabel, such as $^{18}$F.

The present application also includes a method of radiolabel imaging comprising contacting a subject to be imaged with one or more compounds of the application, and performing an imaging technique on the subject, wherein the compounds of the application comprise at least one radiolabel, such as $^{18}$F. In an embodiment the subject is a human or animal and the imaging technique is PET and the one or more compounds of the application or contacted with the subject by administration of a imaging effective amount of the compound(s) to the subject.

The following non-limiting examples are illustrative of the present application:

EXAMPLES

The introduction of the fluorine atom into molecules may bring about changes in the physical and/or chemical properties of the parent molecules, for example it may result in the enhancement of pharmacokinetic properties and/or biological activities. Replacement of hydrogen atoms may also result in improved thermal and metabolic stability. Improved metabolic stability is generally a desirable feature since the possibility exists that in vivo decomposition may produce toxic effects. The properties of the fluorine atom include its small size, low polarizability, high electronegativity and its ability to form strong bonds with carbon. Accordingly, bioactive compounds containing fluorinated groups such as —OCHF$_2$ are useful.

The geminal combination of an alkoxy or aryloxy group with a fluorine atom offers the possibility of bonding/nonbonding resonance, which can be formally expressed by the superposition of a covalent and ionic limiting structure. This phenomenon, which reveals itself as a lengthening and weakening of the carbon-halogen bond and a shortening and strengthening of the carbon-oxygen bond is known as the generalized anomeric effect [Schlosser et al. *Chem. Rev.* 2005, 105, 827-856].

A. General Methods

All starting materials used herein were commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as an internal reference, in deuterated chloroform as solvent unless otherwise indicated. All reported chemical shifts are in ppm on the delta-scale, and the fine splitting of the signals as appearing in the recordings is generally indicated, for example as s: singlet, br s: broad singlet, d: doublet, t: triplet, q: quartet, m: multiplet. Unless otherwise indicated, in the tables below, $^1$H NMR data was obtained at 400 MHz, using CDCl$_3$ as the solvent.

Purification of products was carried out using Chem Elut Extraction Columns (Varian, cat #1219-8002), Mega BE-SI (Bond Elut Silica) SPE Columns (Varian, cat #12256018; 12256026; 12256034) or by flash chromatography in silica-filled glass columns.

B: Synthesis and Characterization of Compounds

I. Preparation of Intermediate Compounds of Formula II

Scheme V outlines the synthesis of intermediate compounds of Formula IV(a) and Formula V(a) used in the preparation of the intermediate compound of Formula II(a) (i), used in the preparation of compounds of Formula I wherein R$_2$ and/or R$_3$ are a —CH$_2$—O—CHF$_2$ moiety.

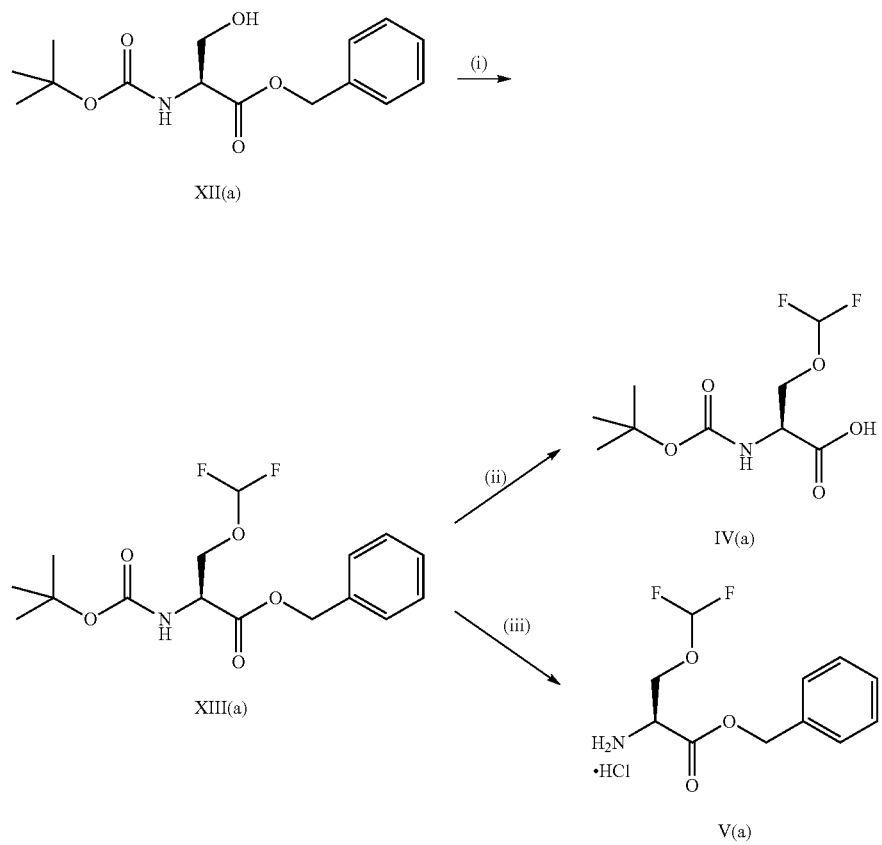

Reagents and conditions used in Scheme V: (i) 2-fluorosulfonyldifluoroacetic acid, Cu(I)I, Na$_2$SO$_4$, CH$_3$CN 0° C./30 min; (ii) H$_2$, Pd/C (10%), THF, RT/2 hrs; (iii) 2M HCl/Et$_2$O, 0° C. to RT/2 hrs.

(a) Preparation of (S)-2-tert-butoxycarbonylamino-3-difluoromethoxy-propionic acid benzyl ester (XIII(a))

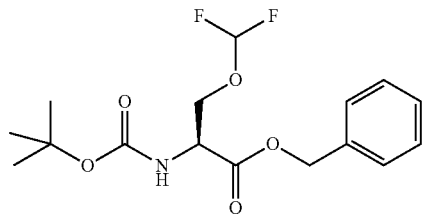 [SMILES: CC(C)(C)OC(=O)N[C@@H](COC(F)F)C(=O)OCc1ccccc1]

To a stirred solution of the compound of Formula XII(a), benzyl 2-(tert-butoxycarbonylamino)-3-hydroxypropanoate (1 g, 3.38 mmol) in acetonitrile (10 mL) was added copper(I) iodide (64.4 mg, 0.338 mmol) and sodium sulfate (48.1 mg, 0.338 mmol). The resulting mixture was stirred at 60° C. and treated with 2,2-difluoro-2-fluorosulfonylacetic acid (524 µL, 5.08 mmol), dropwise, as a solution in acetonitrile (2 mL) over a period of 1.5 h. Upon completion of the addition, the mixture was stirred for a further 30 min then cooled to room temperature. The mixture was diluted with diethyl ether and washed with brine (2×), water (3×) and brine (1×). The organic phase was dried, filtered and concentrated in vacuo then chromatographed in 0-30% ethyl acetate in hexanes, to provide the compound of Formula XIII(a), (S)-2-tert-butoxycarbonylamino-3-difluoromethoxy-propionic acid benzyl ester (458 mg, 40%) as a colorless sticky oil. $^1$H NMR (300 MHz, CDCl$_3$): δ (ppm) 7.32-7.38 (m, 5H), 6.18 (wt, 1H), 5.28 (dd, 1H), 5.19 (dd, 2H), 4.55 (dt, 1H) 4.22 (td, 1H), 4.15 (m, 2H), 1.38 (s, 9H).

Alternatively, the compound of Formula XIII(a), (S)-2-tert-butoxycarbonylamino-3-difluoromethoxy-propionic acid benzyl ester was prepared by difluoromethyl insertion of (S)-2-tert-butoxycarbonylamino-3-thioformyloxy-propionic acid benzyl ester in a 40-90% yield using 2,2-difluoro-1,3-dimethylimidazolidine, as a reagent for difluoromethyl insertion.

(b) Preparation of (S)-2-tert-butoxycarbonylamino-3-difluoromethoxy-propionic acid (IV(a))

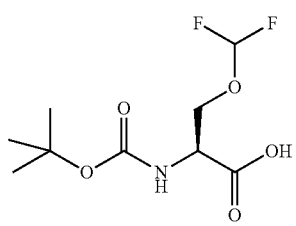 [SMILES: CC(C)(C)OC(=O)N[C@@H](COC(F)F)C(=O)O]

A solution of the compound of Formula XIII(a), (S)-2-tert-butoxycarbonylamino-3-difluoromethoxy-propionic acid benzyl ester (1.76 g, 5.09 mmol) in THF was stirred with 10% Pd/C (360 mg) under a hydrogen atmosphere for 2 hours. The reaction mixture was filtered and concentrated to give the compound of Formula IV(a), (S)-2-tert-butoxycarbonylamino-3-difluoromethoxy-propionic acid (1.3 g, 100%) as a sticky, colorless oil. $^1$H NMR (300 MHz, CDCl$_3$): δ (ppm) 6.21 (wt, 1H), 5.35 (d, 1H), 4.59 (m, 1H), 4.35 (m, 1H), 4.21 (m, 1H) and 1.42 (s, 9H).

(c) Preparation of (S)-2-amino-3-difluoromethoxy-propionic acid benzyl ester Hydrochloride salt (V(a))

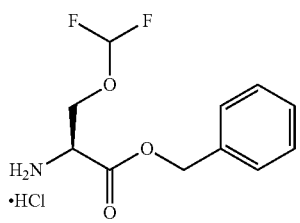 [SMILES: Cl ; N[C@@H](COC(F)F)C(=O)OCc1ccccc1]

A solution of the compound of Formula XIII(a), (S)-2-tert-butoxycarbonylamino-3-difluoromethoxy-propionic acid benzyl ester (2.11 g, 5.89 mmol) in ether (10 mL) was treated with 2M HCl/ether, and stirred at 0° C. for 2 hours. The reaction mixture was concentrated to dryness and triturated with hexane/ether to give the compound of Formula V(a) (S)-2-amino-3-difluoromethoxy-propionic acid benzyl ester hydrochloride salt (1.15 g, 69%) as a white powder. $^1$H NMR (300 MHz, CDCl$_3$): δ (ppm) 7.40-7.33 (m, 5H), 6.53 (broad s, 1H), 6.18 (wt, 1H), 5.25 (dd, 1H), 5.21 (dd, 2H), 4.53 (dt, 1H) 4.18 (td, 1H), 4.16-4.13 (m, 2H).

Scheme VI outlines the synthesis of intermediate compounds of Formula II(a)(i) used in the preparation of the compounds of Formula wherein R$_2$ and R$_3$ are a —CH$_2$—O—CHF$_2$ moiety.

Scheme VI

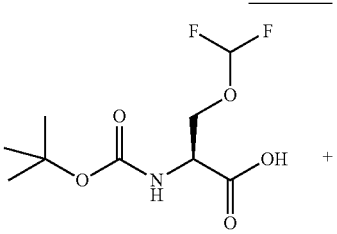

IV(a)

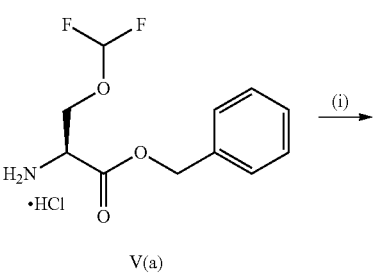

V(a)

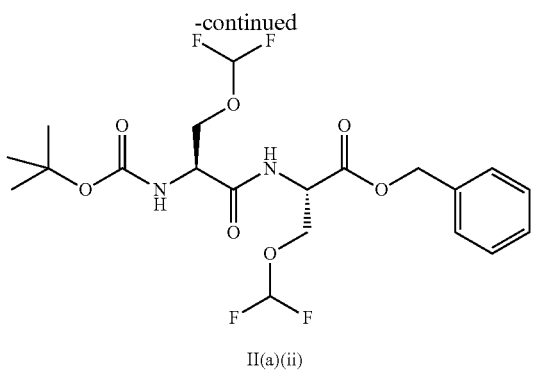

II(a)(ii)

(ii) ↓

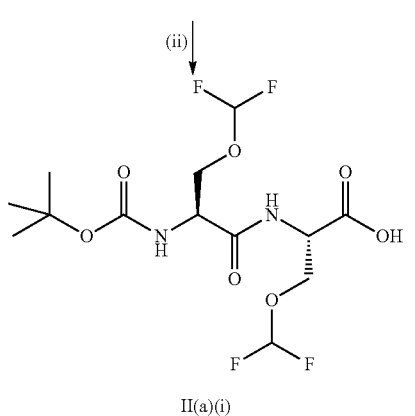

II(a)(i)

Reagents and conditions used in Scheme VI: (i) EDCl·HCl, HOBt, N-methylmorpholine, CH$_2$Cl$_2$, 0° C./ON; (ii) H$_2$, Pd/C (10%), THF, RT/1 hrs.

(d) Preparation of (S)-2-((S)-2-tert-butoxycarbonylamino-3-difluoromethoxy-propionylamino)-3-difluoromethoxy-propionic acid benzyl ester (II(a)(ii))

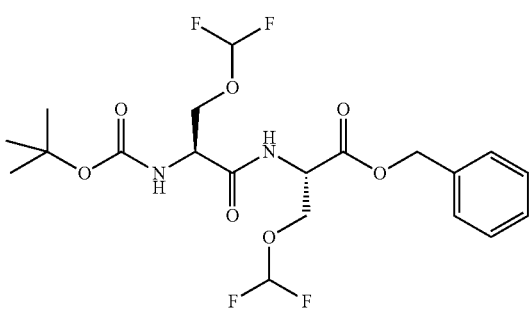 [SMILES: CC(C)(C)OC(=O)N[C@@H](COC(F)F)C(=O)N[C@@H](COC(F)F)C(=O)OCc1ccccc1]

To a solution of the compound of Formula IV(a), (S)-2-tert-butoxycarbonylamino-3-difluoromethoxypropionic acid (1.15 g, 4.49 mmol) and the compound of Formula V(a), (S)-2-amino-3-difluoromethoxypropionic acid benzyl ester hydrochloride salt (1.15 g, 4.08 mmol), HOBt (0.689 g, 5.10 mmol) and EDCl·HCl (0.867 g, 5.10 mmol) in dichloromethane (20 mL) was added N-methylmorpholine (0.45 mL, 8.16 mmol) dropwise at 0° C. The reaction mixture was allowed to warm up to room temperature and stirred overnight. The mixture was then diluted with ethyl acetate and washed successively with water, 1N HCl and brine. The organic layer was dried over MgSO$_4$ and concentrated. The crude product was purified by silica-gel column chromatography, eluting with 10% to 12.5% ethyl acetate in hexanes, to give the compound of Formula II(a)(ii), (S)-2-((S)-2-tert-butoxycarbonylamino-3-difluoromethoxy-propionylamino)-3-di-fluoromethoxy-propionic acid benzyl ester (1.29 g, 65%) as an off-white solid. $^1$H NMR (300 MHz, CDCl$_3$): δ (ppm) 7.35-7.41 (m, 5H), 7.18 (td, 1H), 6.18 (wt, 1H), 6.22 (wt, 1H), 5.25-5.20 (m, 1H), 5.19 (s, 2H), 4.82 (td, 1H), 4.42 (br s, 1H), 4.31 (td, 1H), 4.20-4.15 (m, 2H), 4.01 (dd, 1H), 1.41 (s, 9H).

In a similar manner, using the above general procedure, the intermediate compounds shown in Table 1 were synthesized.

(e) Preparation of (S)-2-((S)-2-tert-butoxycarbonylamino-3-difluoromethoxy-propionylamino)-3-difluoromethoxy-propionic acid (II(a)(i))

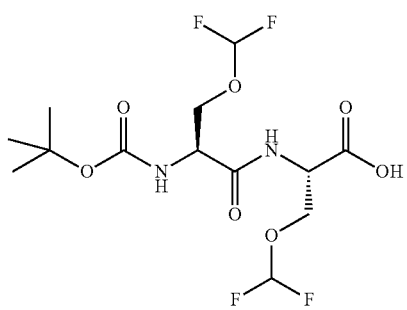 [SMILES: CC(C)(C)OC(=O)N[C@@H](COC(F)F)C(=O)N[C@@H](COC(F)F)C(=O)O]

A solution of the compound of Formula II(a)(ii), (S)-2-((S)-2-tert-butoxycarbonylamino-3-difluoromethoxy-propionylamino)-3-difluoromethoxypropionic acid benzyl ester (1.27 g, 2.63 mmol) in THF was stirred with 10% Pd/C (400 mg) under a hydrogen atmosphere for 1 hour. The reaction mixture was filtered and concentrated to give the compound of Formula II(a)(i), (S)-2-((S)-2-tert-butoxycarbonylamino-3-difluoromethoxy-propionylamino)-3-difluoromethoxy-propionic acid (1.03 g, ~100%) as a sticky, off-white foam. NMR (d$_6$-DMSO, 400 MHz) δ (ppm) 8.34 (d, J=8 Hz, 1H), 7.12 (d, J=8 Hz, 1H), 6.66 (t, J=76 Hz, 1H), 6.62 (t, J=76 Hz, 1H), 4.57-4.51 (m, 1H), 4.37-4.29 (m, 1H), 4.15-4.09 (m, 1H), 4.04-3.97 (m, 2H), 3.92-3.83 (m, 1H), 1.37 (s, 9H).

Scheme VII outlines the synthesis of compound intermediates of Formula IV(b) and Formula V(b) which are used in the preparation of the compounds of Formula (I) wherein R$_2$ and/or R$_3$ is a —CH$_2$—O—CH$_3$ moiety.

Scheme VII

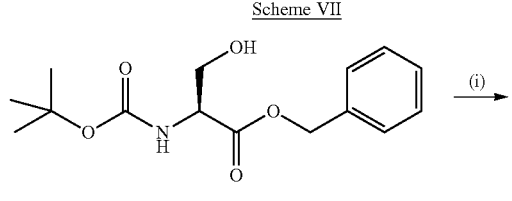

XII(a)

-continued

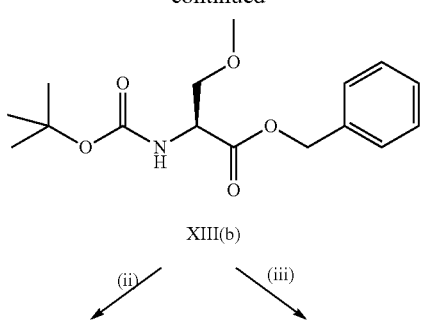

XIII(b)

(ii) ↙   ↘ (iii)

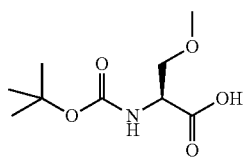   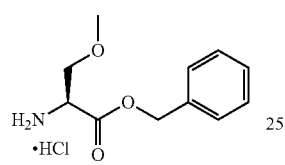

IV(b)         V(b)

Reagents and conditions used in Scheme VII: (i) BF₄(OMe)₃, proton sponge, CH₂Cl₂, 0° C. to TR/ON; (ii) TFA, CH₂Cl₂, 0° C./30 min; (iii) HCl/Et₂O.

(a) Preparation of (S)-2-tert-butoxycarbonylamino-3-methoxy-propionic acid benzyl ester (XIII(b))

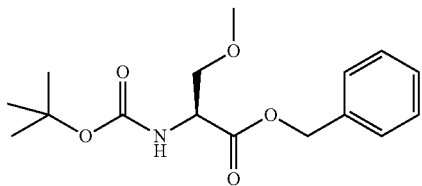 [SMILES: COC[C@H](NC(=O)OC(C)(C)C)C(=O)OCc1ccccc1]

To a solution of the compound of Formula XII(a), (S)-2-tert-butoxycarbonylamino-3-hydroxy-propionic acid benzyl ester (1.7 g, 5.76 mmol) in dichloromethane (50 mL) was added trimethyloxonium tetrafluoroborate (1.11 g, 7.50 mmol), followed by the portion-wise addition of proton sponge (1.61 g, 7.50 mmol). After stirring for 24 hrs at RT, the solution was concentrated, and the residue was dissolved in ethyl acetate, and the solution filtered through a pad of celite. The filtrate was washed with 1 M HCl and brine. The organic layers were dried over MgSO₄, filtered, and concentrated in vacuo. Silica-gel flash chromatography with 5% to 15% ethyl acetate in hexanes afforded the compound of Formula XIII(b), (S)-2-tert-butoxycarbonylamino-3-methoxy-propionic acid benzyl ester (1.24 g, 69.6%) as a colorless oil. ¹H NMR (300 MHz, CDCl₃): δ (ppm) 7.35-7.29 (m, 5H), 4.90-4.87 (m, 1H), 4.51 (s, 2H), 3.92-3.87 (m, 1H), 3.80-3.78 (m, 1H), 3.56 (dd, 2H), 3.42 (dd, 1H), 3.33 (s, 3H), 1.42 (s, 9H).

(b) Preparation of (S)-2-tert-butoxycarbonylamino-3-methoxy-propionic acid (IV(b))

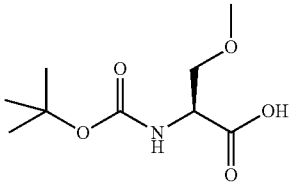

The compound of Formula IV(b) was prepared in a similar manner as the compound of Formula IV(a), described above, from the compound of Formula XIII(b) (S)-2-tert-butoxycarbonylamino-3-methoxy-propionic acid benzyl ester (0.76 g, 2.46 mmol), to provide the compound of Formula IV(b), (S)-2-tert-butoxycarbonylamino-3-methoxy-propionic acid (0.540 mg, 100%) as a sticky, colorless oil.

(c) Preparation of (S)-2-amino-3-methoxy-propionic acid benzyl ester, hydrochloride salt (V(b)

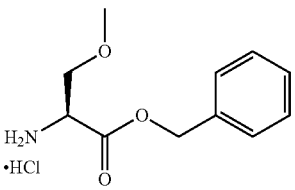

The compound of Formula V(b) was prepared, as a hydrochloride salt, in a similar manner as the compound of Formula V(a), described above, from the compound of Formula XIII(b), (S)-2-tert-butoxycarbonylamino-3-methoxy-propionic acid benzyl ester (0.80 g, 2.59 mmol), to provide the compound of Formula V(b), (S)-2-amino-3-methoxy-propionic acid benzyl ester, hydrochloride salt (100%) as a white powder.

Scheme VIII outlines the synthesis of the intermediate compound of Formula II(b)(i) which is used in the preparation of the compounds of Formula (I) wherein R₂ is a —CH₂—O—CHF₂ moiety and R₃ is a —CH₂—O—CH₃ group.

Scheme VIII

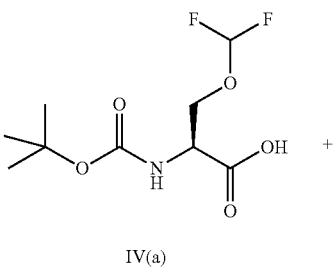

IV(a)

-continued

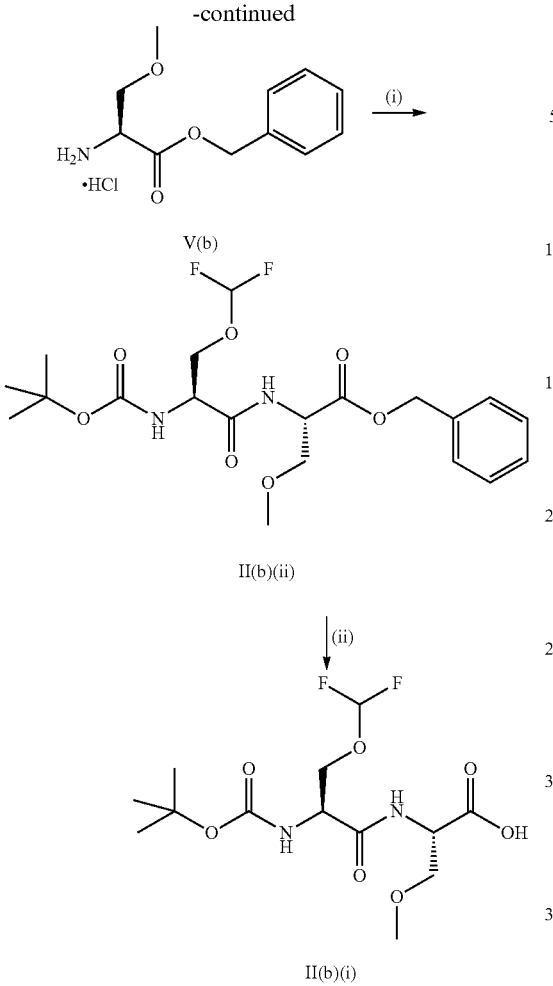

Reagents and conditions used in Scheme VIII: (i) EDCl-.HCl, HOBt, DIPEA, CH$_2$Cl$_2$, 0° C./ON; (ii) H$_2$, Pd/C (10%), THF, RT/2 hrs.

(d) Preparation of (S)-2-((S)-2-tert-butoxycarbonylamino-3-difluoromethoxy-propionylamino)-3-methoxy-propionic acid benzyl ester (II(b)(ii))

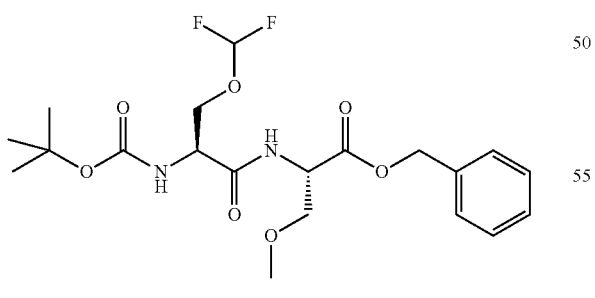

The compound of Formula II(b)(ii) was prepared as an off-white foam in a similar manner as the compound of Formula II(a)(ii), described above, from the compound of Formula IV(a), (S)-2-tert-butoxycarbonylamino-3-difluoromethoxy-propionic acid and the compound of Formula V(b), (S)-2-amino-3-methoxy-propionic acid benzyl ester, hydrochloride salt.

(e) Preparation of (S)-2-((S)-2-tert-butoxycarbonylamino-3-difluoromethoxy-propionylamino)-3-methoxy-propionic acid (II(b)(i))

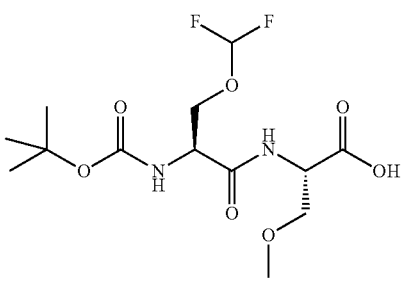 [SMILES: COC[C@H](NC(=O)[C@H](COC(F)F)NC(=O)OC(C)(C)C)C(=O)O]

The compound of Formula II(b)(i) was prepared, as an off-white sticky foam, in a similar manner as the compound of Formula II(a)(i), described above from the compound of Formula II(b)(ii), (S)-2-((S)-2-tert-butoxycarbonylamino-3-difluoromethoxy-propionylamino)-3-methoxy-propionic acid benzyl ester.

Scheme IX outlines the synthesis of the intermediate of Formula II(c)(i), used in the preparation of the compounds of Formula (I) when R$_2$ is a —CH$_2$—O—CH$_3$ group and R$_3$ is a —CH$_2$—O—CHF$_2$ moiety.

Scheme IX

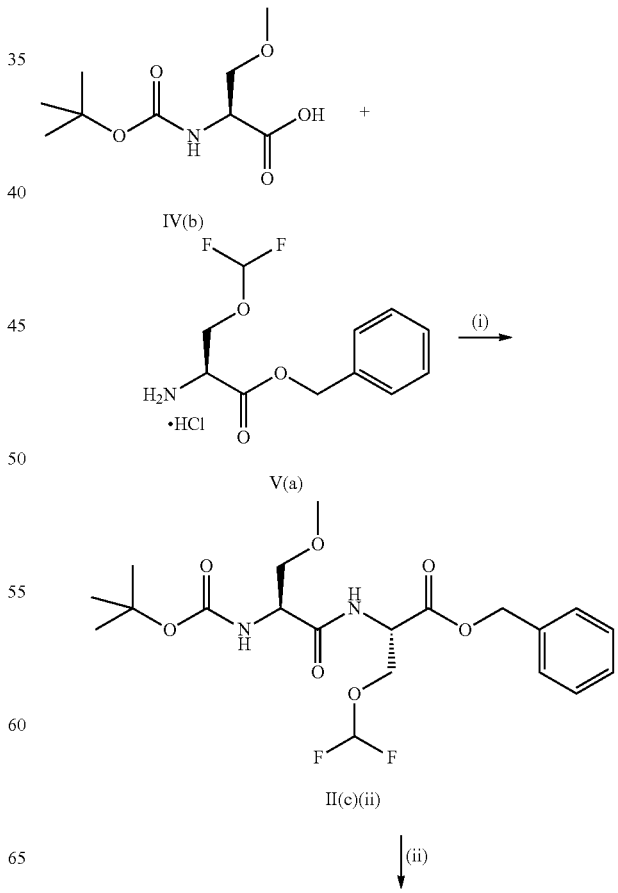

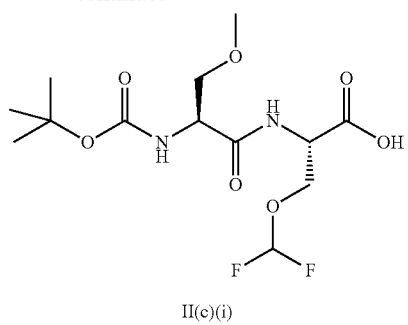

II(c)(i)

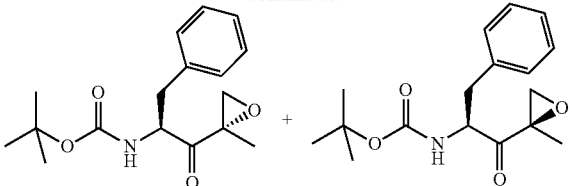

S,S-IX(a)     S,R-IX(a)

(iv) ↓     (iv) ↓

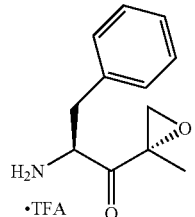     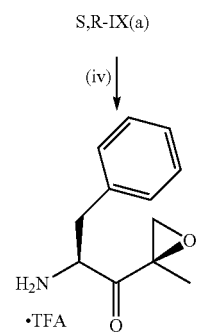

S,S-III(a)(i)     S,R-III(a)

Reagents and conditions used in Scheme IX: (i) EDCl-.HCl, HOBt, DIPEA, CH₂Cl₂, 0° C./ON; (ii) H₂, Pd/C (10%), THF, RT/2 hrs.

In a similar manner to the above general procedure, the other compounds shown in Table 2 were synthesized.

II. Preparation of Intermediate Compounds of Formula III

Scheme X outlines the synthesis of intermediate epoxyketones of Formula III used for the preparation of compounds of Formula I wherein R⁴ is —CH₂C₆H₅ and R⁵ is methyl.

Scheme X

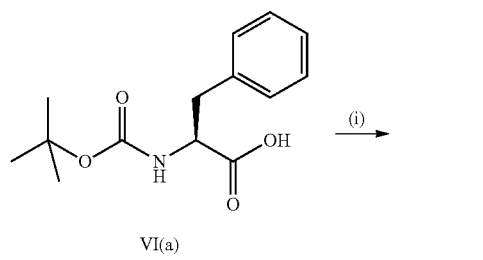

VI(a)

(i) ↓

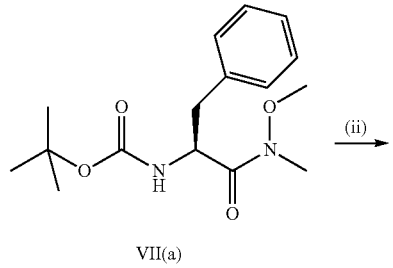

VII(a)

(ii) ↓

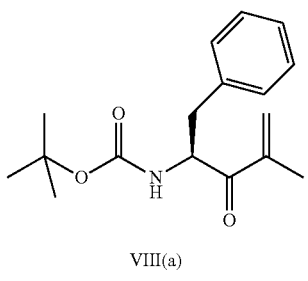

VIII(a)

(iii) ↓

Reagents and conditions used in Scheme X: (i) iBuO-COCl, N-methylmorpholine, HNMe(OMe).HCl, TEA, CH₂Cl₂, 0° C./45 min; (ii) isopropenylmagnesium bromide, THF, 0° C./2 hrs or 2-bromopropene, t-BuLi, Et₂O, −78° C./2 hrs; (iii) (a) H₂O₂ (35%), benzonitrile, iPr₂EtN, MeOH, 0° C. to RT/ON; (b) Silica-gel column chromatography; (iv) TFA, CH₂Cl₂, 0° C./30 min.

In a similar manner as Scheme X, the synthesis of the intermediate epoxyketones of Formula III(b) for compounds of Formula I wherein R₄ is CH₂CH(CH₃)₂ and R₅ is methyl was prepared.

(a) Preparation of [(S)-1-(methoxy-methyl-carbamoyl)-2-phenyl-ethyl]-carbamic acid tert-butyl ester (VII(a))

To a solution of (S)-2-tert-butoxycarbonylamino-3-phenyl-propionic acid (24.85 g, 93.66 mmol) in dichloromethane (150 mL) was added N-methylmorpholine (10.3 mL, 93.66 mmol), followed by addition of isobutyl chloroformate (12.25 mL, 93.66 mmol) at 0° C. The reaction mixture was stirred for 20 min. then N,O-dimethylhydroxylamine hydrochloride (9.14 g, 93.66 mmol) in one portion was added. Subsequently, triethylamine (13 mL, 93.66 mmol) was added dropwise over 15 min. The reaction mixture was stirred for another hour, then it was quenched with 1N HCl (100 mL) and the organic phase was washed with saturated NaHCO₃ and brine (500 mL). The organic layers were dried over (MgSO₄), filtered, and concentrated in vacua to give the Weinreb amide of Formula VII(a), [(S)-1-(methoxymethyl-carbamoyl)-2-phenyl-ethyl]-carbamic acid tert-butyl ester as a clear sticky oil (29.3 g, 100%). $^1$H NMR (400 MHz, d$_6$-DMSO): δ (ppm) 7.33-7.09 (m, 6H), 4.61-4.47 (m, 1H), 3.70 (s, 3H), 3.08 (s, 3H), 2.89-2.78 (m, 1H), 2.75-2.63 (m, 1H), 1.29 (s, 9H).

(b) Preparation of ((S)-1-benzyl-3-methyl-2-oxo-but-3-enyl)-carbamic acid tert-butyl ester (VIII(a))

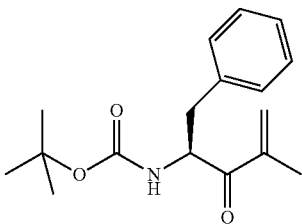 [SMILES: C=C(C)C(=O)[C@H](Cc1ccccc1)NC(=O)OC(C)(C)C]

To a 0° C. solution of the above Weinreb amide of Formula VII(a), (28.88 g, 93.66 mmol) in THF (150 mL) was added a 0.5 M solution in THE of isopropenyl magnesium bromide (386 mL, 192.9 mmol) at 0° C. over 40 min. The reaction mixture was then stirred at room temperature for 2 hours. The reaction mixture was then quenched at 0° C. with 1N HCl (350 mL). The aqueous layer was extracted with EtOAc (2×200 mL). The organic layer was washed successively with water and brine, dried over MgSO$_4$, filtered, and concentrated in vacua to give, after silica-gel flash chromatography with 5% to 10% ethylacetate/hexanes, the compound of Formula VIII(a), (S)-1-benzyl-3-methyl-2-oxo-but-3-enyl)-carbamic acid tert-butyl ester (14.5 g, 53.5%) as a white powder. $^1$H NMR (400 MHz, d$_5$-DMSO): δ (ppm) 7.33-7.09 (m, 6H), 4.61-4.47 (m, 1H), 3.70 (s, 3H), 3.08 (s, 3H), 2.89-2.78 (m, 1H), 2.75-2.63 (m, 1H), 1.29 (s, 9H).

(c) Preparation of [(S)-1-benzyl-2-((S)-2-methyl-oxiranyl)-2-oxo-ethyl]-carbamic acid tert-butyl ester and [(S)-1-benzyl-2-((R)-2-methyl-oxiranyl)-2-oxo-ethyl]-carbamic acid tert-butyl ester (IX(a))

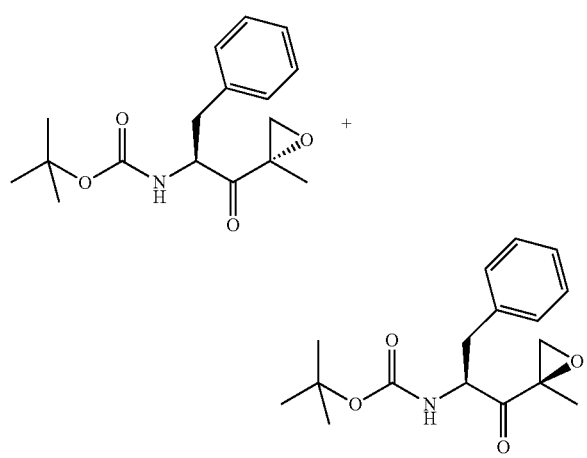

To a solution of the above compound of Formula VIII(a), ((S)-1-benzyl-3-methyl-2-oxo-but-3-enyl)-carbamic acid tert-butyl ester (5.78 g, 20 mmol) in MeOH (250 mL) at 0° C. was added benzonitrile (15.46 mL, 150 mmol), H$_2$O$_2$ 35% solution in water (34.4 mL, 400 mmol), and diisopropylethylamine (26 mL, 150 mmol). The reaction mixture was stirred at 0° C. to room temperature overnight. The resulting mixture was concentrated under reduced pressure to dryness. The obtained residue was quenched with ice-water (100 mL) to provide a white precipitate. After filtration, the aqueous layer was extracted with 20% ethyl acetate in hexanes (2×200 mL). The organic layer was washed successively with water and brine, dried over MgSO$_4$, filtered, and concentrated in vacua to give, after silica-gel flash chromatography with 3% to 3.5% ethyl acetate/hexanes the compound of Formula S, R-IX(a), [(S)-1-benzyl-2-((R)-2-methyl-oxiranyl)-2-oxo-ethyl]-carbamic acid tert-butyl ester (3.33 g, 54%) as a white solid ($^1$H NMR (300 MHz, CDCl$_3$): δ (ppm) 7.21-7.29 (m, 3H), 7.17-7.21 (m, 2H), 4.92 (dd, 1H), 4.58 (td, 1H), 3.25 (d, 1H), 3.18 (dd, 1H), 2.94 (d, 1H), 2.75 (dd, 1H), 1.45 (s, 3H), 1.39 (s, 9H)), and the compound of Formula S, S-IX(a), [(S)-1-benzyl-2-((S)-2-methyl-oxiranyl)-2-oxo-ethyl]-carbamic acid tert-butyl ester (1.66 g, 27%) as a sticky oil ($^1$H NMR (300 MHz, CDCl$_3$): δ (ppm) 7.30-7.22 (m, 3H), 7.20-7.15 (m, 2H), 4.95 (dd, 1H), 4.62 (td, 2H), 3.25 (d, 1H), 3.00 (dd, 1H), 2.82 (dd, 1H), 2.61 (dd, 2H), 1.45 (s, 3H), 1.40 (s, 9H)).

Preparation of (S)-2-amino-1-((R)-2-methyl-oxiranyl)-3-phenyl-propan-1-one, TFA salt (S, R-III(a))

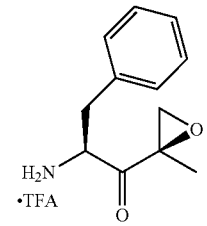

To a solution of (2.20 g, 7.20 mmol) of the compound of Formula S, R-IX(a), [(S)-1-benzyl-2-((R)-2-methyl-oxiranyl)-2-oxo-ethyl]-carbamic acid tert-butyl ester in dichloromethane (10 mL), TFA (3.3 mL) was added at 0° C. The reaction mixture was stirred for 30 min. Excess of TFA was evaporated to dryness, and the residue obtained was triturated with 20% ether in hexanes (20 mL), followed by 100% hexanes. After evaporation of solvents, drying under high vacuum provided the compound of Formula S, R-III(a) (S)-2-amino-1-((R)-2-methyl-oxiranyl)-3-phenyl-propan-1-one, TFA salt (2.3 g, 100%), as an off-white powder. $^1$H NMR (300 MHz, methanol-d): δ(ppm) 7.22-7.44 (m, 5H), 4.32 (dd, 1H), 4.39 (dd, 1H), 3.17 (dd, 1H), 2.95 (dd, 1H), 2.88 (dd, 1H), 1.57 (s, 3H).

Alternatively, epoxyketones of the Formulae S, S-III(a) and S, R-III(a) can be prepared as outlined in Schemes XI and XII.

Scheme XI
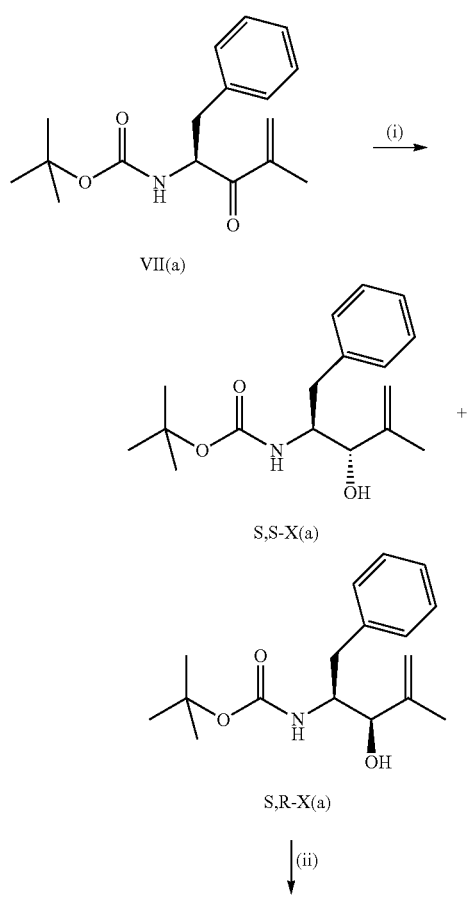
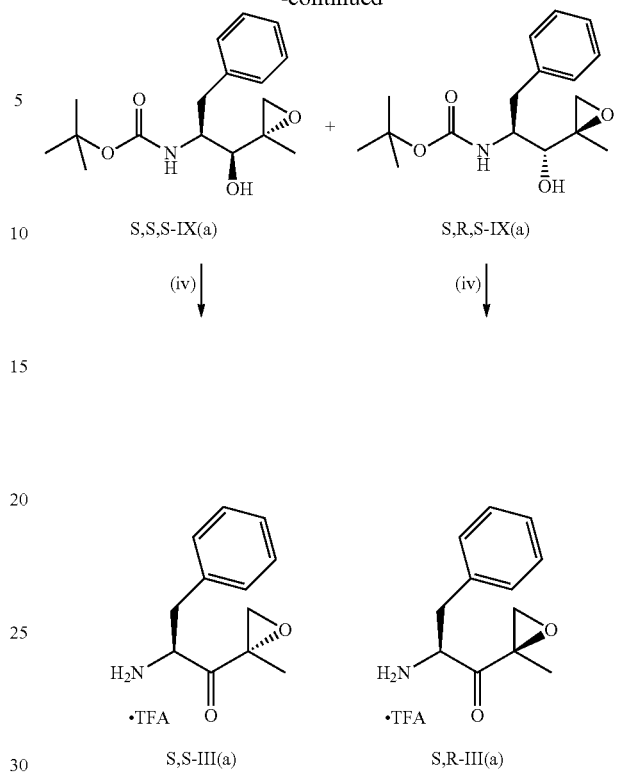
Reagents and conditions used in Scheme XI: (i) NaBH$_4$, CeCl$_3$.7H$_2$O, MeOH, THF, 0° C./30 min; (ii) (a) VO(acac)$_2$, t-BuO$_2$H, CH$_2$Cl$_2$, 0° C. to RT/1 hr; (b) silica-gel column chromatography; (iii) (a) Dess-Martin periodinane, CH$_2$Cl$_2$, 0° C. to RT/2 hrs; (b) TFA, CH$_2$Cl$_2$, 0° C./30 min.
Scheme XII
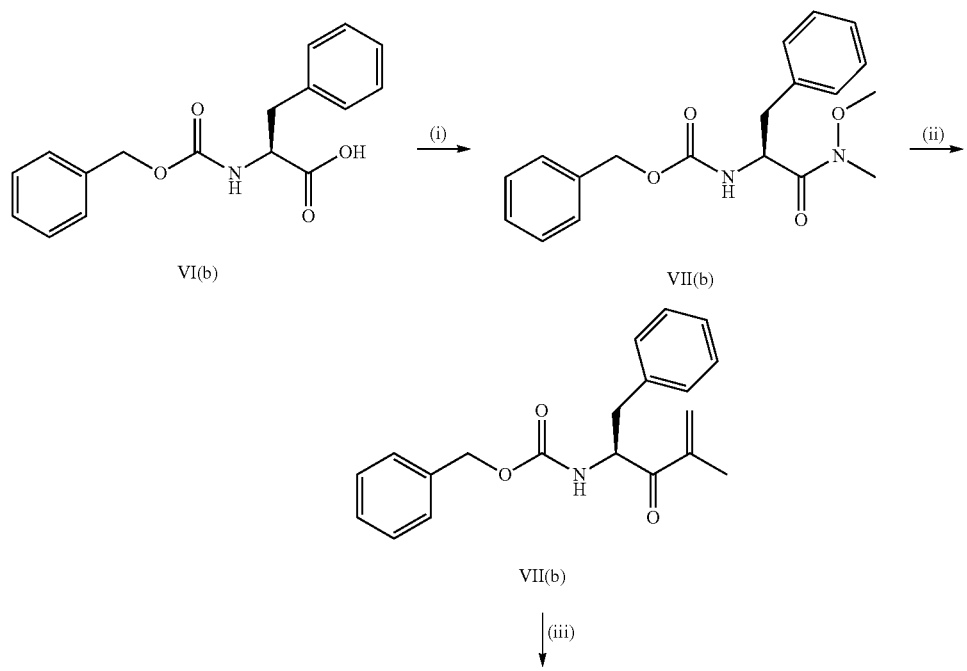

-continued

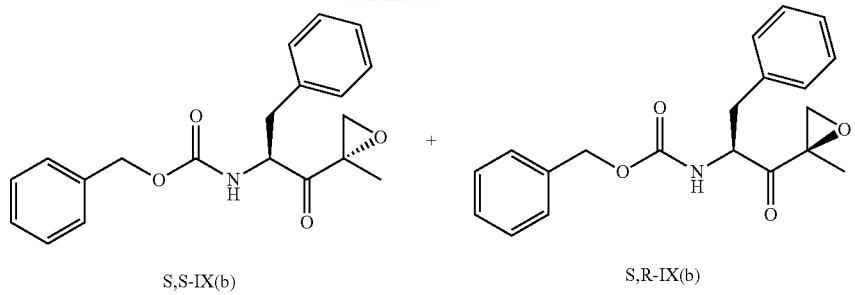

S,S-IX(b)  S,R-IX(b)

(iv)↓  (iv)↓

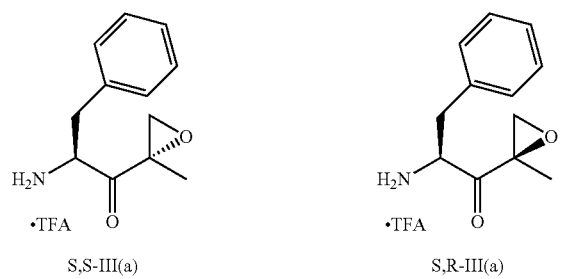

S,S-III(a)  S,R-III(a)

Reagents and conditions used in Scheme XII: (i) iBuO-COCl, N-methylmorpholine, HNMe(OMe).HCl, TEA, CH₂Cl₂, 0° C./1 hr.; (ii) isopropenylmagnesium bromide, THF, 0° C./2 hrs or 2-bromopropene, t-BuLi, Et₂0, −78° C./2 hrs.; (iii) (a) H₂O₂ (35%), benzonitrile, i-Pr₂EtN, MeOH, 0° C. to RT/ON; (b) silica-gel column chromatography; (iv) H₂, Pd/C (10%), TFA, RT/6 hrs.

II. Preparation of Compounds of Formula I

Example 1

The preparation of the compound of Formula I of Example 1, 2-methyl-thiazole-5-carboxylic acid ((S)-1-{(S)-1-[(S)-1-benzyl-2-((R)-2-methyloxiranyl)-2-oxo-ethyl-carbamoyl]-2-difluoromethoxyethylcarbamoyl}-2-difluoromethoxyethyl)-amide is outlined in Scheme XIII.

Scheme XIII

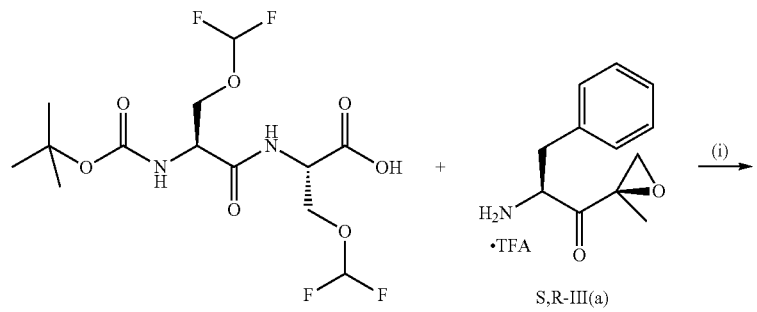

II(b)(i)  S,R-III(a)

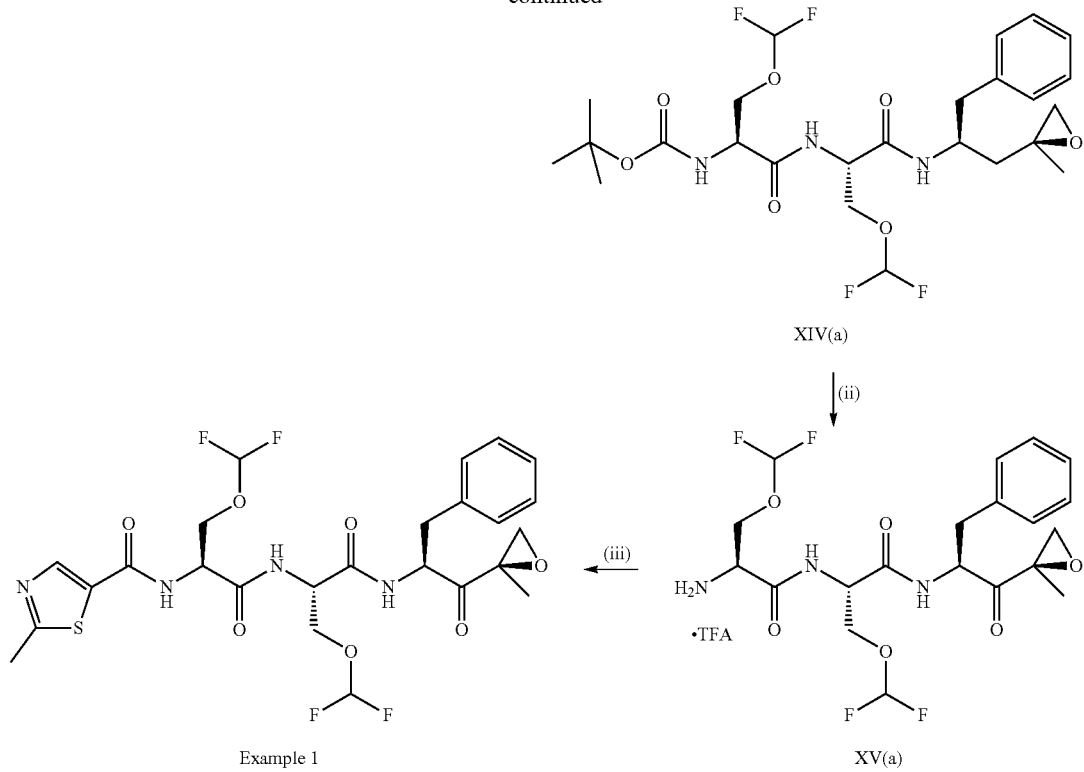

XIV(a)

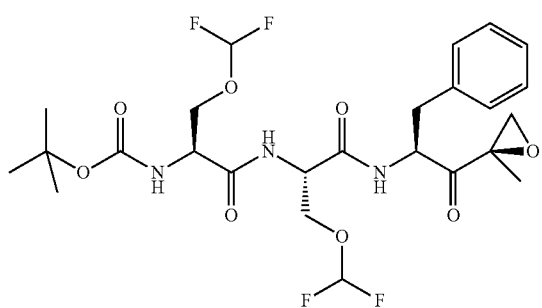 [SMILES: CC(C)(C)OC(=O)N[C@@H](COC(F)F)C(=O)N[C@@H](COC(F)F)C(=O)N[C@@H](Cc1ccccc1)C(=O)[C@@]1(C)CO1]

Example 1

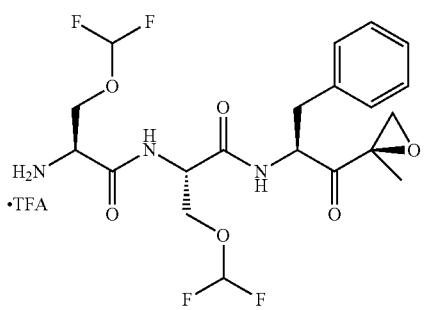 [SMILES: C[C@]1(C(=O)[C@H](Cc2ccccc2)NC(=O)[C@H](COC(F)F)NC(=O)[C@@H](N)COC(F)F)CO1]

XV(a)

Reagents and conditions used in Scheme XIII: (i) HBTU, HOBt, DIPEA, THF, 0° C. to RT/ON; (ii) $H_2$, Pd/C (10%), THF, RT/2 hrs.; (iii) HBTU, HOBt, DIPEA, THF, 2-methyl-thiazole-5-carboxylic acid, 0° C. to RT/ON.

(a) Preparation of ((S)-1-{(S)-1-[(S)-1-benzyl-2-((R)-2-methyl-oxiranyl)-2-oxo-ethylcarbamoyl]-2-difluoromethoxy-ethylcarbamoyl}-2-difluoromethoxy-ethyl)-carbamic acid tert-butyl ester (XIV(a))

To a solution of the compound of Formula II(b)(i), (S)-2-((S)-2-tert-butoxycarbonylamino-3-difluoromethoxy-propionylamino)-3-methoxy-propionic acid (2.75 g, 7.028 mmol) and the compound of Formula S, R-III(a), (S)-2-amino-1-((R)-2-methyl-oxiranyl)-3-phenyl-propan-1-one, TFA salt (12.04 g, 6.389 mmol), HOBt (1.04 g, 7.67 mmol), HBTU (2.91 g 7.67, mmol) in THF (75 mL) was added DIPEA (2.22 mL, 12.75 mmol) dropwise at 0° C. The reaction mixture was allowed to warm up to room temperature and was stirred overnight. The mixture was then quenched with ice water, washed with $NaHCO_3$ and brine and extracted with 2×100 mL of ethyl acetate. The organic layer was dried over $MgSO_4$ and concentrated. The crude product was purified by column chromatography, eluting with 20% to 30% ethyl acetate in hexanes, to give the title compound (2.7 g, 73%) as an off-white solid. $^1$H NMR (300 MHz, $CDCl_3$): δ (ppm) 7.21-7.32 (m, 3H), 7.14 (dd, 2H), 6.85 (wd, 1H), 6.72 (wd, 1H), 6.18 (wt, 1H), 6.14 (wt, 1H), 5.26 (br s, 1H), 4.86 (td, 1H), 4.58 (td, 1H), 4.36 (m, 1H), 4.32-4.08 (m, 2H), 4.01 (dd, 1H), 3.90 (dd, 1H), 3.24 (d, 1H), 3.12 (dd, 1H), 2.90 (d, 1H), 2.85 (dd, 1H), 1.48 (s, 3H), 1.44 (s, 9H).

In a similar manner to the above general procedure, the compounds shown in Table 3 were synthesized.

(b) Preparation of (S)-2-amino-N—{(S)-1-[(S)-1-benzyl-2-((R)-2-methyl-oxiranyl)-2-oxo-ethylcarbamoyl]-2-difluoromethoxy-ethyl}-3-difluoromethoxy-propionamide TFA salt (XV(a))

To a solution of the compound of Formula XIV(a), ((S)-1-{(S)-1-[(S)-1-benzyl-2-((R)-2-methyl-oxiranyl)-2-oxo-ethylcarbamoyl]-2-difluoromethoxy-ethylcarbamoyl}-2-difluoromethoxy-ethyl)-carbamic acid tert-butyl ester (2.68 g, 4.62 mmol) in dichloromethane (10 mL) at 0° C. was added TFA (10 mL), and the resulting mixture was stirred for 1 hr. Excess TFA was evaporated to dryness, and the residue obtained was triturated with ether in hexanes (2×20 mL) to provide the compound of Formula XV(a), (S)-2-amino-N—{(S)-1-[(S)-1-benzyl-2-((R)-2-methyl-oxiranyl)-2-oxo-ethylcarbamoyl]-2-difluoromethoxy-ethyl}-3-difluoromethoxy-propionamide TFA salt (2.34 g, 85%), as a pale-yellow solid. $^1$H NMR (300 MHz, d$_6$-DMSO): δ (ppm) 7.42-7.32 (m, 3H), 7.23 (dd, 2H), 6.85 (wd, 1H), 6.71 (br s, 1H), 6.68 (wd, 1H), 6.10 (w t, 1H), 5.98 (wt, 1H), 5.12 (br s, 1H), 4.78 (td, 1H), 4.51 (td, 1H), 4.29 (m, 1H), 4.30-3.99 (m, 2H), 3.97 (dd, 1H), 3.85 (dd, 1H), 3.21 (d, 1H), 3.10 (dd, 1H), 2.86 (d, 1H), 2.81 (dd, 1H), 1.45 (s, 3H).

In a similar manner to the above general procedure, the compounds shown in Table 4 were synthesized.

(c) Preparation of 2-methyl-thiazole-5-carboxylic acid((S)-1-{(S)-1-[(s)-1-benzyl-2-((R)-2-methyl-oxiranyl)-2-oxo-ethylcarbamoyl]-2-difluoromethoxy-ethylcarbamoyl}-2-difluoromethoxy-ethyl)-amide Example 1

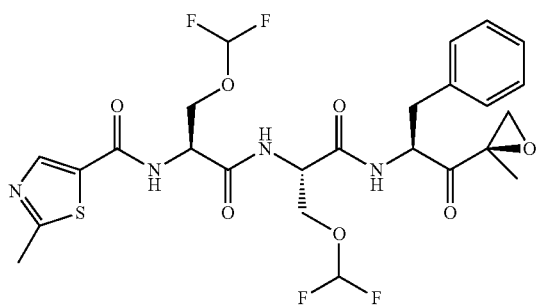 [SMILES: Cc1ncc(C(=O)N[C@@H](COC(F)F)C(=O)N[C@@H](COC(F)F)C(=O)N[C@@H](Cc2ccccc2)C(=O)[C@@]2(C)CO2)s1]

To a solution of the compound of Formula XV(a), (S)-2-amino-N—{(S)-1-[(S)-1-benzyl-2-((R)-2-methyl-oxiranyl)-2-oxo-ethylcarbamoyl]-2-difluoromethoxy-ethyl}-3-difluoromethoxy-propionamide TFA salt (2.2 g, 3.70 mmol), 2-methyl-thiazole-5-carboxylic acid (0.635 g, 4.44 mmol), HOBt (0.649 g, 4.81 mmol) and HBTU (1.82 g, 4.81 mmol) in THF (70 mL) was added DIPEA (1.29 mL, 7.4 mmol) dropwise at 0° C. The reaction mixture was allowed to warm up to room temperature and was stirred overnight. The mixture was then quenched with ice water, washed with NaHCO$_3$ and brine and extracted with 2×100 mL of ethyl acetate. The organic layer was dried over magnesium sulphate and concentrated. The crude product was purified by column chromatography, eluting with 70% to 80% ethyl acetate in hexanes, to give the compound of Formula I of Example 1. (2.11 g, 94.6%) as a pale-yellowish solid. $^1$H NMR (300 MHz, CDCl$_3$): δ (ppm) 8.10 (s, 1H), 7.28-7.25 (m, 3H), 7.20 (dd, 2H), 6.82 (d, 1H), 6.79 (d, 1H), 6.65 (d, 1H), 6.18 (wt, 1H), 6.14 (wt, 1H), 4.90-4.65 (m, 2H), 4.60 (td, 1H), 4.35 (dd, 1H), 4.25 (dd, 1H), 4.05 (td, 1H), 3.95 (dd, 1H), 3.30 (d, 1H), 3.28 (dd, 1H), 3.16 (d, 1H), 2.90 (dd, 1H), 2.85 (dd, 1H), 2.75 (s, 3H), 1.41 (s, 3H).

In a similar manner to the above general procedure, the compounds of Formula I of Examples 2-24 shown in Table 5 were synthesized.

Example 25

The compound of Formula I of Example 25, (2S)-2-[[(2S)-3-(difluoromethoxy)-2-[(2-morpholinoacetyl)amino] propanoyl]amino]-N-[(1S)-3-methyl-1-[(2R)-2-methyloxirane-2-carbonyl]butyl]-3-phenyl-propanamide was prepared according to the following synthetic procedure:

(a) Preparation of tert-butyl 2-morpholinoacetate

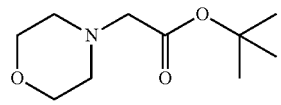

To a stirred solution of tert-butyl bromoacetate (8.47 mL, 57.4 mmol) in THF (50 mL) was added a 1:1 mixture of triethylamine (8 mL, 57.4 mmol) and morpholine (5.02 mL, 57.4 mmol), dropwise (a mild exotherm was observed) and the resulting white suspension was stirred at 60° C. for 2 h. The mixture was diluted with water (100 mL) and saturated sodium carbonate (50 mL) and extracted with ethyl acetate (2×50 mL). The combined organics were washed with saturated sodium carbonate (100 mL), water (3×50 mL), and brine (50 mL). The organic phase was dried over anhydrous sodium sulfate, filtered and concentrated then chromatographed in 0%-100% ethyl acetate in hexanes. Product-containing fractions were concentrated in vacuo giving the title product (11.5 g, quantitative) as a pale yellow liquid. $^1$H NMR (CDCl$_3$, 400 MHz): δ (ppm) 3.78-3.71 (m, 4H), 3.10 (s, 2H), 2.59-2.54 (m, 4H), 1.46 (m, 9H).

(b) Preparation of 2-morpholinoacetic acid hydrochloride salt

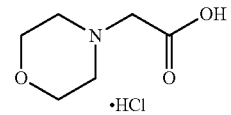

Tert-butyl 2-morpholinoacetate (11 g, 54.7 mmol) was stirred with HCl, 4M in dioxane (54 mL), giving a white precipitate (a mild exotherm was observed) which slowly dissolved with stirring at room temperature. Ten minutes after complete dissolution, the mixture solidified. Then the mixture was warmed to 60° C. and the thick suspension was stirred vigorously overnight. The mixture was then cooled to room temperature, diluted with diethyl ether (60 mL) and filtered to collect the title compound (8 g, 80%) as a white solid. $^1$H NMR (CD$_3$OD, 400 MHz): δ (ppm) 4.13 (s, 2H), 3.94 (brm, 4H), 3.41 (brm, 4H).

(c) Preparation of benzyl (2S)-2-(tert-butoxycarbonylamino)-3-phenyl-propanoate

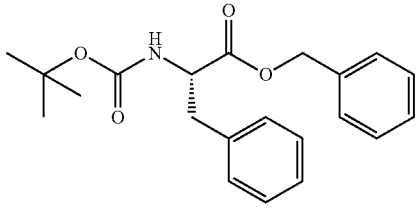 [SMILES: CC(C)(C)OC(=O)N[C@@H](Cc1ccccc1)C(=O)OCc1ccccc1]

To a stirred solution of Boc-Phe-OH (10 g, 37.7 mmol) in DMF (50 mL) was added potassium carbonate (7.81 g, 56.5 mmol) followed by benzyl chloride (4.55 mL, 39.6 mmol) and the resulting suspension was stirred at 60° C. for 3 d. The mixture was diluted with water (400 mL) and extracted with ethyl acetate (75 mL, 2×25 mL). The combined organics were washed with brine (200 mL), water (3×100 mL) and brine (50 mL). The organic phase was dried over anhydrous sodium sulfate, filtered and concentrated then chromatographed on silica gel eluting with 0%-20% ethyl acetate in hexanes. The product-containing fractions were concentrated in vacuo giving the title compound (12.84 g, 95%) as a white solid.

In a similar manner to the above general procedure, benzyl (2S)-2-(tert-butoxycarbonylamino)-4-methyl-pentanoate was synthesized.

(d) Preparation of benzyl (2S)-2-amino-3-phenyl-propanoate hydrochloride

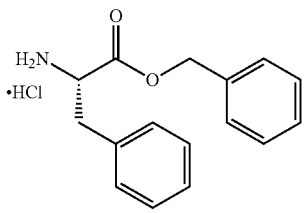 [SMILES: Cl ; N[C@@H](Cc1ccccc1)C(=O)OCc1ccccc1]

Benzyl (2S)-2-(tert-butoxycarbonylamino)-3-phenyl-propanoate (12.8 g, 36 mmol) was stirred in HCl, 2 M in diethyl ether (90 mL) and HCl, 4 M in dioxane (18 mL) and the resulting mixture was stirred overnight at room temperature. The mixture was then diluted with hexanes (100 mL) and filtered to collect the title compound (7.98 g, 76%) as a fine white powder. $^1$H NMR (CD$_3$OD, 400 MHz): δ (ppm) 7.40-7.15 (m, 10H), 5.23 (s, 2H), 4.36-4.31 (m, 1H), 3.26-3.12 (m, 2H).

(e) Preparation of benzyl (2S)-2-[[2S)-2-(tert-butoxycarbonylamino)-3-(difluoromethoxy)propanoyl]amino]-3-phenyl-propanoate (II(g)(ii))

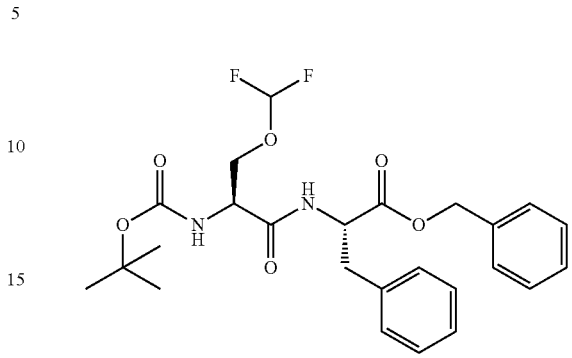

(2S)-2-(tert-butoxycarbonylamino)-3-(difluoromethoxy) propanoic acid (1.0 g, 3.92 mmol), benzyl (2S)-2-lamino-3-phenyl-propanoate (1.2 g, 4.11 mmol) and HOBt hydrate (0.66 g, 4.31 mmol) were stirred in DCM (20 mL). The resulting mixture was treated with EDC hydrochloride (0.83 g, 4.31 mmol), cooled to 0° C. and treated with DIPEA (0.715 mL, 4.11 mmol). The mixture was warmed to room temperature and stirred overnight. The mixture was diluted with DCM (30 mL) and washed with saturated sodium bicarbonate (2×50 mL). The organic phase was dried over anhydrous sodium sulfate, filtered and concentrated in vacuo then chromatographed in 0%-40% ethyl acetate in hexanes. The product-containing fractions were concentrated in vacuo giving the compound of Formula II(g)(ii) (1.9 g, 98%) as a waxy solid. $^1$H NMR (CDCl$_3$, 400 MHz): δ (ppm) 7.40-6.95 (m, 10H), 6.71 (m, 1H), 6.14 (t, J=74 Hz, 1H), 5.19-5.09 (m, 2H), 4.95-4.85 (m, 1H), 4.40-4.20 (m, 2H), 3.98-3.90 (m, 1H), 3.19-3.10 (m, 2H), 1.44 (s, 9H).

(f) Preparation of benzyl (2S)-2-[[(2S)-2-amino-3-(difluoromethoxy)propanoyl]amino]-3-phenyl-propanoate hydrochloride (XVI(a))

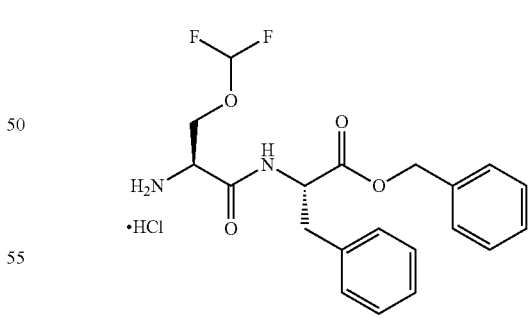

Benzyl(2S)-2-[[(2S)-2-(tert-butoxycarbonylamino)-3 (difluoromethoxy)propanoyl]amino]-3-phenyl-propanoate (1.9 g, 3.86 mmol) was stirred in HCl, 2M in diethyl ether (12 mL), at room temperature overnight. The resulting suspension was diluted with hexanes and the filtered to collect the compound of Formula XVI(a) (1.65 g, quantitative yield) as a white solid. The product was used directly in the subsequent reaction.

(g) Preparation of benzyl (2S)-2-[[(2S)-3-(difluoromethoxy)-2-[(2-morpholinoacetyl)amino]propanoyl]amino]-3-phenyl-propanoate (XVII(a))

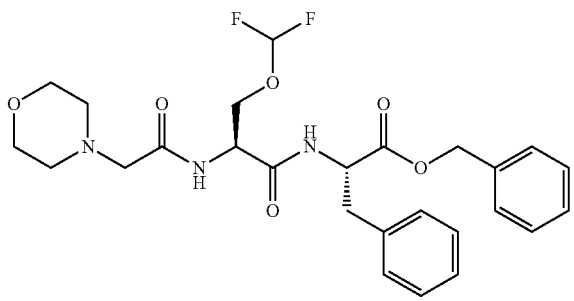 [SMILES: O=C(CN1CCOCC1)N[C@@H](COC(F)F)C(=O)N[C@@H](Cc1ccccc1)C(=O)OCc1ccccc1]

To a stirred solution of benzyl (2S)-2-[[(2S)-2-amino-3-(difluoromethoxy)propanoyl]amino]-3-phenyl-propanoate hydrochloride (1.65 g, 3.84 mmol), 2-morpholinoacetic acid hydrochloride (768 mg, 4.23 mmol) and HOBt hydrate (648 mg, 4.23 mmol) in DCM (20 mL) was added EDC hydrochloride (811 mg, 4.23 mmol). The resulting mixture was cooled to 0° C. and treated with DIPEA (0.736 mL, 4.23 mmoL), dropwise, warmed to room temperature and stirred overnight. The mixture was diluted with DCM (30 mL) and washed with saturated sodium bicarbonate (2×50 mL). The organic phase was dried over anhydrous sodium sulfate, filtered and concentrated in vacuo then chromatographed on silica gel eluting with 0%-100% ethyl acetate in hexanes. The product-containing fractions were concentrated in vacuo giving the compound of Formula XVII(a) (1.54 g, 77%) as a white solid. $^1$H NMR (CDCl$_3$, 400 MHz): δ (ppm) 7.72 (m, 1H), 7.35-6.90 (m, 10H), 6.12 (t, J=74 Hz, 1H), 5.14-5.04 (m, 2H), 4.81-4.75 (m, 1H), 4.65-4.55 (m, 1H), 4.26-4.20 (m, 1H), 3.93-3.87 (m, 1H), 3.65-3.50 (m, 4H), 3.15-2.90 (m, 4H), 2.45-2.35 (m, 4H).

In a similar manner to the above general procedure, the compounds shown in Table 6 were synthesized.

(h) Preparation of (2S)-2-[[(2S)-3-(difluoromethoxy)-2-[(2-morpholinoacetyl)amino]propanoyl]amino]-3-phenyl-propanoic acid (XVIII(a))

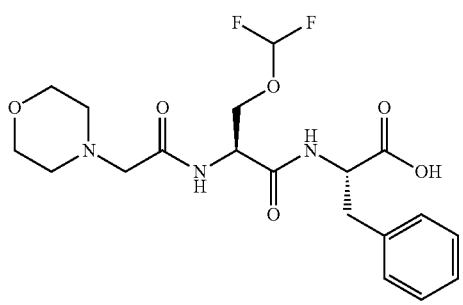 [SMILES: O=C(CN1CCOCC1)N[C@@H](COC(F)F)C(=O)N[C@@H](Cc1ccccc1)C(=O)O]

A stirred solution of benzyl (2S)-2-[[(2S)-3-(difluoromethoxy)-2-[(2-morpholinoacetyl)amino]propanoyl] amino]-3-phenyl-propanoate (1.54 g, 2.96 mmol) in THF (10 mL) was treated with palladium (10 wt. % on activated carbon) (157 mg, 0.148 mmol) and stirred under an atmosphere of hydrogen, balloon pressure, for 1 h. The mixture was then filtered through a pad of Celite™ and concentrated in vacuo giving the compound of Formula XVIII(a) (1.27 g, quantitative yield) as colourless foam. $^1$H NMR (CDCl$_3$, 400 MHz): δ (ppm) 8.09 (m, 1H), 7.24-7.05 (m, 5H), 6.10 (t, J=74 Hz, 1H), 5.6 (brs, 1H), 4.70-4.60 (m, 2H), 4.15-4.01 (m, 1H), 3.95-3.85 (m, 1H), 3.70-3.55 (m, 4H), 3.25-2.90 (m, 4H), 2.65-2.50 (m, 4H).

In a similar manner to the above general procedure, the compounds shown in Table 7 were synthesized.

(i) Preparation of (2S)-2-[[(2S)-3-(difluoromethoxy)-2-[(2 morpholinoacetyl)amino]propanoyl]amino]-N-[(1S)-3-methyl-1-[(2R)-2-methyloxirane-2-carbonyl]butyl]-3-phenyl-propanamide Example-25

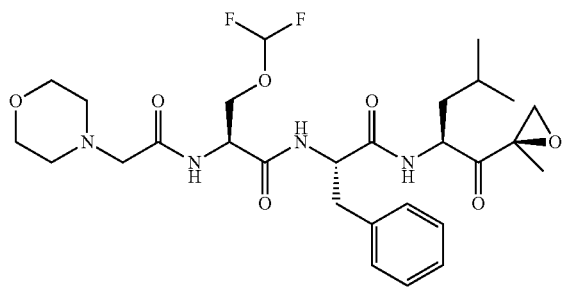 [SMILES: CC(C)C[C@H](NC(=O)[C@H](Cc1ccccc1)NC(=O)[C@H](COC(F)F)NC(=O)CN1CCOCC1)C(=O)[C@@]1(C)CO1]

To a stirred solution of (2S)-2-[[(2S)-3-(difluoromethoxy)-2-[(2-morpholinoacetyl)-amino]propanoyl] amino]-3-phenyl-propanoic acid (200 mg, 0.46 mmol), (2S)-2-amino-4-methyl-1-(2-methyloxiran-2-yl)pentan-1-one trifluoroacetate (133 mg, 0.46 mmol) and HOBt hydrate (71 mg, 0.46 mmol) in THF (10 mL) cooled to 0° C. was added HBTU (176 mg, 0.46 mmol) followed by DIPEA (162 μL, 0.93 mmol). The mixture was warmed to room temperature and stirred for 4 h. The mixture was diluted with DCM (40 mL) and washed with saturated sodium bicarbonate (2×50 mL). The organic phase was dried over anhydrous sodium sulfate, filtered and concentrated then chromatographed on silica gel eluting with 50%-100% ethyl acetate in hexanes. The product-containing fractions were concentrated in vacuo and triturated with a 1:1 mixture of hexanes:diethyl ether giving the compound of Formula I of Example 25 (108 mg, 40%) as a pale solid. $^1$H NMR (CDCl$_3$, 400 MHz): δ (ppm) 7.78 (m, 1H), 7.31-7.15 (m, 5H), 6.71 (m, 1H), 6.22 (t, J=74 Hz, 1H), 6.10 (m, 1H), 4.65-4.49 (m, 3H), 4.30-4.20 (m, 1H), 4.09-4.00 (m, 1H), 3.75-3.63 (m, 4H), 3.25-2.80 (m, 5H), 2.55-2.45 (m, 4H), 2.17 (s, 3H), 1.55-1.18 (m, 3H), 0.95-0.85 (m, 6H).

In a similar manner to the above general procedure, the compounds of Formula I of Examples 26-33 shown in Table 8 were synthesized.

C. Biological Assays

Cells and Cell Culture

Human multiple myeloma cell lines 8226, H929, JJN3, KMH11, KMS11, KMS18, LP1, MM1S, OPM2 and U266 were grown in Iscove modified Dulbecco's medium (IMDM). Human leukemia cell lines K562, OCI-AML2 and U937 were cultured in RPMI-1640 medium. Primary peripheral blood mononuclear cells were isolated from multiple myeloma patients by Ficoll density gradient centrifugation and bone marrow aspirates were obtained from multiple myeloma patients at the Princess Margaret Cancer Centre of the University Health Network (UHN; Toronto, ON, Canada). Primary cells were cultured in IMDM. The collection and use of human tissue for this study were approved by the UHN institutional ethics review board. All cell culture media were obtained from the Ontario Cancer Institute Tissue Culture Media Facility (Toronto, ON, Canada) and were supplemented with 10% fetal calf serum, 100 μg/mL penicillin, and 100 U/mL streptomycin (Hyclone, Logan, Utah). All cells were grown in a humidified incubator at 37° C. with 5% $CO_2$.

Proteasome Enzymatic Activity (Tumor Cell Lysates)

Cells were harvested by centrifugation at 1,200 rpm at room temperature. Cell pellets were washed with PBS and lysed with assay lysis buffer (50 mM HEPES (N-2-hydroxyethylpiperazine-N'-2-ethanesulfonic acid), pH 7.5; 150 mM NaCl; 1% Triton X-100; 2 mM ATP). Cell lysates were incubated on ice for 30 minutes, mixed by vortex every 5 minutes, and then centrifuged at 12,000 g for 10 minutes. The supernatant was transferred to a 96-well plate. For each assay, 10 μg of total protein were incubated for 1 hour at 37° C. with increasing concentrations (1 nM to 10 μM) of test compound diluted in assay buffer (50 mM Tris-HCl (tris (hydroxymethyl)aminomethane-HCl), pH 7.5; 150 mM NaCl). DMSO alone was used as a control in every assay plate. After incubation, a specific fluorogenic proteasome substrate was added to each assay reaction at a final concentration of 40 μM in a total volume of 100 μL. N-Succinyl-Leu-Leu-Val-Tyr-7-amino-4-methylcoumarin (Suc-Leu-Leu-Val-Tyr-AMC) was used for measuring chymotrypsin-like (CT-L) activity, t-butoxycarbonyl-Leu-Arg-Arg-7-amino-4-methylcoumarin (Boc-Leu-Arg-Arg-AMC) for trypsin-like (T-L) activity, and benzyloxycarbonyl-L-leucyl-L-leucyl-L-glutamyl-7-amino-4-methylcoumarin (Z-Leu-Leu-Glu-AMC) for caspase-like (C-L) activity. The excitation wavelength was set at 360 nm and the fluorescence emission wavelength of AMC was detected at 460 nm. The fluorescence of free AMC released during the enzymatic reaction was measured with a SpectraMax M5 fluorescent spectrophotometric plate reader (Molecular Devices, Sunnyvale, Calif.). AMC release rate was measured at 37° C. in a kinetic mode, recording every 5 minutes for 30 minutes. Experiments were performed in triplicate and repeated at least twice.

Cell Viability Assays

Cellular viability was primarily assessed by 3-(4,5-dimethylthiazol-2-yl)-5-(3-carboxymethoxyphenyl)-2-(4-sulfophenyl)-2H-tetrazolium (MTS) assay according to the manufacturer's instructions (Promega; Madison, Wis.). Cells were first seeded at a density of 10,000 cells per well in tissue culture-treated 96-well plates. Two hours after seeding, cells were treated with compounds for 72 hours at concentrations as indicated. As a control, cells were treated with DMSO alone in every assay plate. Following treatment and the MTS assay, cell viability was independently confirmed by reading the optical density (O.D.) at 490 nm and by exclusion of trypan blue stain (Invitrogen; Burlington, ON, Canada). The viability of primary mononuclear cells was determined by staining with Annexin V.

Table 9 summarizes data obtained for representative compounds of Formula I for cell viability and CT-L proteasome activity using OCI-AML-2 and KMS-11 cell lines.

Proteases Purified from *Thermoplasma Acidophilum*

Increasing concentrations (0, 0.26, 0.519, 1.0375, 2.075, 4.15 and 8.3 pM) of compounds of Formula (I) and bortezomib were incubated with 1pM purified beta subunits of proteasomes isolated from *Thermoplasma acidophilum* in assay buffer supplemented with 2 mM ATP. DMSO alone was used as a control. After 1 hour of incubation at 37° C., the Suc-Leu-Leu-Val-Tyr-AMC substrate was added at a final concentration of 40 μM and CT-L proteasome activity was measured as described above for tumor cell lysates.

FIG. 1 shows the effect of a representative of compounds of Formula I (the compound of Example 1) on the enzymatic activity of purified proteasomes, compared to bortezomib and shows that the compound of Formula 1 of Example 1 disrupts the ubiquitin-proteasome system. Purified beta proteasome subunits from the archaebacteria *Thermoplasma acidophilum* (A) and whole cell lysates from the human myeloma cell line LP1 (B) were used in the study.

Immunoblotting Assay:

Whole cell lysates were prepared from LP1 cells in RIPA lysis buffer. Anti-ubiquitin antibody was purchased from Cell Signaling Technology Inc, (Danvers, Mass.) and anti-tubulin antibody was purchased from Sigma-Aldrich (St. Louis, Mo.). Secondary horseradish peroxidase-conjugated goat anti-mouse or anti-rabbit IgG was purchased from Amersham Bioscience (Piscataway, N.J.). Detection was performed using an enhanced chemiluminescence kit from Pierce, (Rockford, Ill.).

LP1 cells exposed to compounds of Formula I demonstrated a time-dependent and dose-dependent increase in the abundance of high molecular weight ubiquitylated proteins detected by immunoblot, using tubulin as a loading control bortezomib; IB, immunoblot. Specifically, the compound of Examples 1 & 25 were tested and showed an $IC_{50}$<50 nM.

Combination Assays: Viability of Myeloma LP1 Cells in Culture

To examine whether compounds of Formula I can be combined with other conventional and newer anti-multiple myeloma agents, such as dexamethasone and bortezomib, respectively, LP1 myeloma cells were treated for 72 hours with increasing concentrations of compounds of Formula I in combination with dexamethasone or bortezomib. After incubation, cell growth and viability was measured by the MTS assay. The combination index (CI) analysis, where a CI<1 indicates synergy between two drugs, a CI=1 indicates additivity, and a CI>1 indicates antagonism, was used to determine whether the cytotoxicity produced by the combinations with compounds of Formula I were synergistic, additive, or antagonistic.

The effects of combining these agents with a representative of compounds of Formula I i.e. the compound of Example 1 on the viability of myeloma LP1 cells in culture were assessed. LP1 cells were treated for 72 hours with increasing concentrations of the compound of Example 1 in combination with dexamethasone or bortezomib. After incubation, cell growth and viability was measured by the MTS assay.

Figure 2:
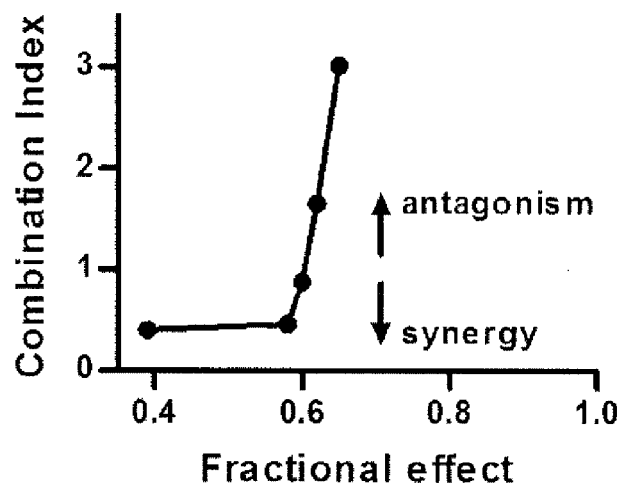
FIG. 2 shows the compound of Example 1 synergized with standard antimyeloma therapeutics when combined in a fixed ratio for 72 hours at low fractional effect levels. Synergy was assessed using the MTS assay and combination index (CI) analysis, where a CI<1 indicates synergy between two drugs, a CI=1 indicates additivity, and a CI>1 indicates antagonism.
Figure 2:
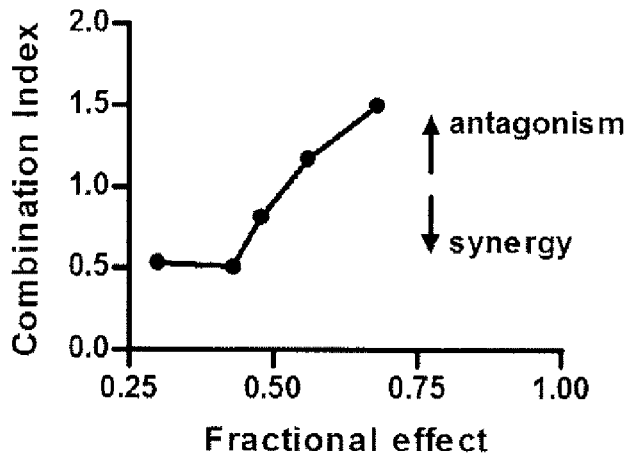

The combination of the compound of Example 1 and bortezomib was synergistic with Combination Index values of 0.41, 0.46, and 0.88 at Fraction affected (Fa) levels of 0.39, 0.58, and 0.6, respectively (FIG. 2A).

Thus using low doses of bortezomib may limit its off-target activity and associated adverse effects while allowing for a more efficient, synergistic, and specific blockade of CT-L proteasome activity in combination with a compound of Formula 1 such as the compound of Example 1.

The combination of the compound of Example 1 and dexamethasone was synergistic with Combination Index values of 0.41, 0.44, and 0.5 at Fraction affected levels of 0.43, 0.5, and 0.64, respectively (FIG. 2B).

The data provides the rationale for combining the compound of Example 1 with another agent such as bortezomib to achieve useful proteasome inhibition and antitumor activity, which may allow for use of lower doses of agents such as bortezomib and potentially reduced side effects.

Cell Death in Primary Myeloma Cells Preferential Over Normal Hematopoietic Cells:

The viability of leukemia and myeloma cells treated with compounds of Formula I or bortezomib was assessed with the use of a CellTiter 96™ AQueous One Solution Cell Proliferation Assay (Promega, Madison, Wis.), which is a form of the 3-(4,5-dimethylthiazol-2-yl)-5-(3-carboxymethoxyphenyl)-2-(4-sulfophenyl)-2H-tetrazolium inner salt (MTS) assay, or with fluorescence-based Alamar Blue cell viability reagent (Invitrogen, Carlsbad, Calif.) according to manufacturer's instructions and as described previously [*J. Natl. Cancer Inst.* 2007, 99(10), 811-822; *Hum. Reprod.* 2007, 22(5), 1304-1309] or by trypan blue staining.

Apoptosis was measured by staining cells treated with compounds of Formula I with annexin V-fluorescein isothiocyanate and propidium iodide (both from Biovision Research Products, Mountain View, Calif.) and flow cytometry according to manufacturer's instructions and as previously described [*Blood.* 2005, 105(10), 4043-4050]. Experiments were performed at least in duplicate and repeated at least twice (n=4-20 data points). Viable primary myeloma cells were identified by staining with phycoerythrin-conjugated mouse monoclonal anti-CD138 antibody (20 µL/106 cells; Beckman Coulter, Brea, Calif.). The percentage of myeloma cells that were CD138 positive and annexin V negative after compounds of Formula (I) treatment compared with untreated samples was quantified as a marker of cell viability as previously described [*Blood.* 2007, 109(12), 5430-5438].

Effects of a representative of compounds of Formula I (the compound of Example 1) on the viability of primary malignant and normal hematopoietic cells isolated from patient samples was also studied. The mononuclear cells from a bone and marrow of a patient with myeloma were incubated for 24 hours with increasing concentrations of the compound of Example 1 (Patient 1); the peripheral blood mononuclear cells from a patient with plasma cell leukemia were incubated for 24 hours with increasing concentrations of the compound of Example 1 (Patient 2); and a primary myeloma patient's samples were treated with increasing concentrations of the compound of Example 1 (Patient 3). Viability of normal hematopoietic cells (CD138−) and myeloma cells (CD138+) were measured by flow cytometry with PE-labeled anti-CD138 and FITC-labeled Annexin V co-staining.

Figure 3:
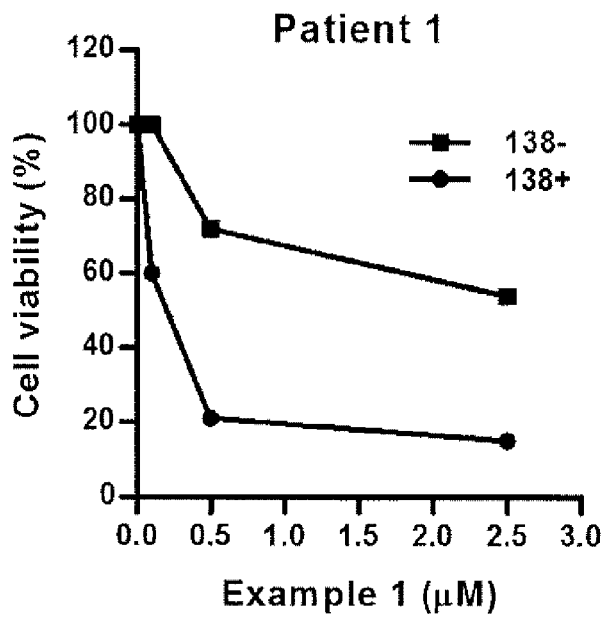
FIG. 3 shows the effects of the compound of Example 1 on the cell viability of samples from patients with multiple myeloma (A,C) or from the peripheral blood of a patient with plasma cell leukemia (B).
Figure 3:
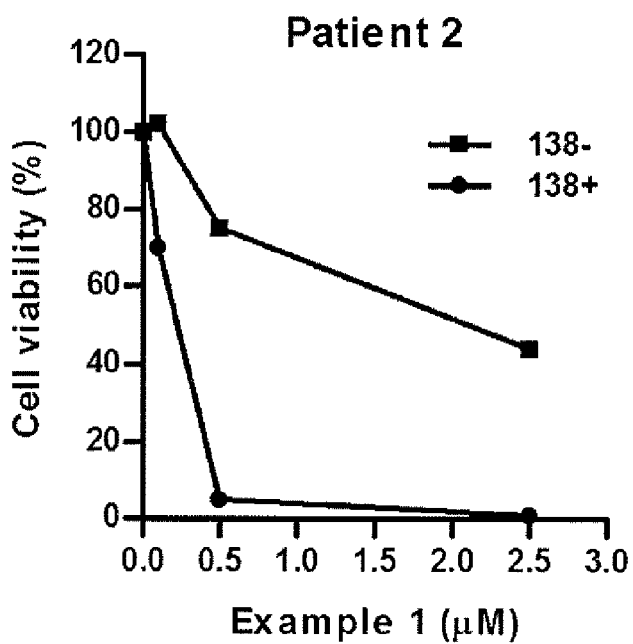
Figure 3:
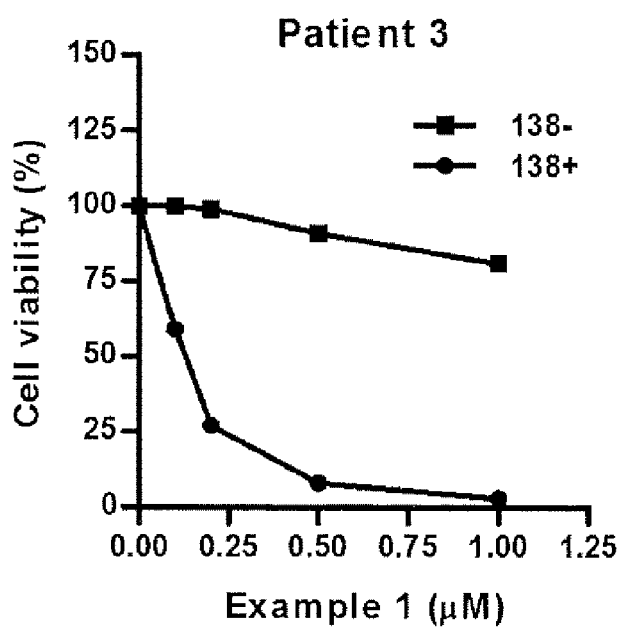

Data represent the percentage of viable cells from each patient sample (FIG. 3). FIG. 3 shows the effects of the compound of Example 1 on the cell viability of primary samples from myeloma patients detected by Annexin V staining and flow cytometry following 24 hours of treatment, relative to vehicle control. The compound of Example 1 selectively reduced the viability of primary CD138+ myeloma cells over CD138-normal hematopoietic cells isolated from the bone marrow of patients with multiple myeloma (FIGS. 3A and 3C) or from the peripheral blood of a patient with plasma cell leukemia (FIG. 3B). The compound of Example 1 induced cell death in the plasma cells of the myeloma patients at nanomolar concentrations. The compound of Example 1 was less cytotoxic to the normal mononuclear hematopoietic cells with an $LD_{50}$>2.5 µM. By contrast, carfilzomib demonstrates a much narrower therapeutic index between CD138+ and CD-138− in patient samples [Trudel et al. ASH 2009, Poster Board 1-867].

Murine Red Blood Cells and Organ Homogenates

All mouse experiments were performed in accordance with approval from the Ontario Cancer Institute institutional animal review board. Five- to six-week-old male non-obese diabetic/severe combined immunodeficient (NOD/SCID) mice were grouped randomly (n=3 mice per group). Mice were administered vehicle (5% DMSO, 20% Cremophor) or compounds of Formula I at different doses either intravenously or by oral gavage, and venous blood samples (20-50 µL) were collected from each mouse over 24 hours. Blood samples were mixed with heparin (APP Pharmaceuticals; Schaumburg, Ill.) in 0.5 mL tubes in accordance with the manufacturer's instructions. After centrifugal separation at 3,000 g for 10 minutes, red blood cells (RBCs) in the bottom layer were transferred into a new tube and stored at −70° C. until use. RBCs were lysed with assay lysis buffer and incubated on ice for 30 minutes, mixing by vortex every 5 minutes, and then centrifuged at 12,000 g for 10 minutes. The supernatant was transferred to a 96-well plate and proteasome activity was measured as described in above for tumor cell lysates.

To evaluate proteasome activity of compounds of Formula I in the organs of treated mice, five- to six-week-old male NOD/SCID mice were sacrificed by $CO_2$ inhalation 4 hours after oral gavage with control vehicle and administered representative of compounds of Formula I at doses of 30 mg to 100 mg. The brain, liver, heart, lung, kidney, femurs and bone marrow were removed, washed with PBS, and stored at −70° C. until use. Prior to analysis, mouse organs were thawed and homogenized on ice in assay lysis buffer. Femurs were cut at both ends and bone marrow was flushed out with assay lysis buffer. Organ homogenates were centrifuged at 13,000 g for 30 minutes at 4° C. and the supernatant was used for measuring proteasome activity as described above for tumor cell lysates.

Proteasome subunit activity (Chymotrypsin-like, Trypsin-like, Caspase-like, CT-L, T-L, C-L, respectively) were monitored over the course of 24 hrs following oral administration of representative compounds of Formula I. NOD/SCID mice were treated with the compound from Example 1 (50 mg/kg by oral gavage) and the compound from Example 26 (60 mg/kg by oral gavage) or vehicle control for up to 24 hours, as described above.

Table 10 summarizes the data for the representative compounds of Formula (I); the compounds of Examples 1 and 26. As can be seen from the data in Table 10, the compounds of Examples 1 and 26 display pharmacodynamic activity following oral administration to mice.

National Cancer Institute (NCI) Screening Panel:

Representative compounds of Formula I were screened using the National Cancer Institute (NCI) screening panel, which consists of a panel of 60 different human tumor cell lines, representing leukemia [CCRF-CEM, HL-60 (TB), K-562, MOLT-4, SR], melanoma [LOX IMVI, MALME-3M, M14, SMDA-MB-435, SK-MEL-2, SK-MEL-28, SK-MEL-5, UACC-257 and UACC-62] and cancers of the lung [A549/ATCC, EKVX, HOP-62, HOP-93, NCI-H226, NCI-H23, NCI-H322M, NCI-H460], colon [COLO 205, HCT-116, HCT-15, HT29, KM12, SW-620], brain [SF-268, SF-295, SF-539, SNB-19, SNB-75, U251], ovary [IGROV1, OVCAR-3, OVCAR-4, OVCAR-5, OVCAR-8, NCI/ADR-RES, SK-OV-3], breast [MCF7, MDA-MB-231, BT-549, T-47D, MDA-MB-468], prostate [PC-3, DU-145], and renal [786-0, A498, ACHN, CAKI-1, RXF-393, SN12C, TK-10, UO-31] cancers.

After 24 h, two plates of each cell line are fixed in situ with TCA, to represent a measurement of the cell population for each cell line at the time of drug addition ($T_z$). Experimental drugs are solubilised in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA (trichloroacetic acid). Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilised with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, ($T_z$), control growth, (C), and test growth in the presence of drug at the five concentration levels ($T_i$)], the percentage growth is calculated at each of the drug concentration levels. Percentage growth inhibition is calculated as: $[(T_i-T_z)/(C-T_z)]\times 100$ for concentrations in which $T_i>/=T_z$ and $[(T_i-T_z)/T_z]\times 100$ for concentrations in which $T_i<T_z$.

Three dose response parameters are calculated for each experimental agent. Growth inhibition of 50% ($GI_{50}$) is calculated from $[(T_i-T_z)/(C-T_z)]100=50$, which is the drug concentration resulting in a 50% reduction in the net protein increase (as measured by SRB staining) in control cells during the drug incubation. The drug concentration resulting in total growth inhibition (TGI) is calculated from $T_i=T_z$. The $LC_{50}$ (concentration of drug resulting in a 50% reduction in the measured protein at the end of the drug treatment as compared to that at the beginning) indicating a net loss of cells following treatment is calculated from $[(T_i-T_z)/T_z]\times 100=-50$. Values are calculated for each of these three parameters if the level of activity is reached. However, if the effect is not reached or is exceeded, the value for that parameter is expressed as greater or less than the maximum or minimum concentration tested.

The results obtained from this study shows compounds of Formula I are effective against the cell lines of the 60 human tumor cell lines panel. Inhibition of human cancer cell lines in vitro by representative compounds of Formula (I) are shown in Table 11 (Example 1), Table 12 (Example 25), Table 13 (Example 26) and Table 14 (Example 29).

Inhibition of Tumor Growth in Mouse Xenograft Models:
Efficacy on Tumor Growth in Hollow Fiber Assay (HFA)

Hollow fibre assay in vivo pharmacodynamic studies were carried out. This in vivo animal model uses semi-permeable biocompatible fibres that are filled with cancer cells, heat-sealed and implanted surgically (s.c. or i.p.) in mice or rats, which can then be treated with chemotherapeutics. Many different cell lines from different tissue origins and cellular characteristics can be encapsulated within the fibres, providing a cost-effective screening method.

The Oncology Program Screening and Characterization Strategy group at NCI uses HFA, which provides quantitative indices of drug efficacy with minimal expenditures of time and materials. Thus, the HFA is being utilized as the initial in vivo experience for compounds of Formula I.

A total of 3 different tumor lines are prepared for each experiment so that each mouse receives 3 intraperitoneal implants (1 of each tumor line) and 3 subcutaneous implants (1 of each tumor line). A compound is considered for xenograft testing if it produces cell kill of any cell line at either dose level evaluated, or it has a combined ip+sc score of 20 or greater, a sc score of 8 or greater. This scoring system has been validated by DCTDC statisticians in CTEP to represent a level of detection expected to score current "standard" agents as active.

The compound of Example 1 was evaluated in an HFA assay via ip administration at two doses; a 75 mg/kg/dose and a 35.5 mg/kg/dose, QD λ 4. A standard panel of 12 tumor cell lines was used for hollow fiber screening of compound of Formula I. These include NCI-H23 and NCI-H522 for non-small cell lung cancer, MDA-MB-231 for breast cancer, MDA-MB-435, LOX IMVI and UACC-62 for melanoma, SW-620 and COLO 205 for colon cancer, OVCAR-3 and OVCAR-5 for ovarian cancer, and U251 and SF-295 for CNS (central nervous system) cancer. The compound of Example 1 of Formula I produced cell killing of multiple cell lines at either of the two doses (75 mg/kg/dose and 35.5 mg/kg/dose).

Efficacy on Tumor Growth in Leukemia AML2 Xenograft Models:

Sublethally irradiated NOD-SCID mice bearing an established human tumor xenograft derived from RL and BALB/c mice challenged with the murine tumor cell line AML2 were treated twice weekly on days 1 and 2 (QD×2) with a dose of 30 mg/kg to 200 mg/kg of the compound of Example 1 by oral gavage. Dosing began on Day 6 post tumor challenge. Results demonstrated that compounds of Formula I exhibit antitumor response. For example, the compound of Example 1 of Formula I exhibits an antitumor response of greater than 40% tumor growth inhibition in the AML2 mouse xenograft leukemia model at 30 mg/kg with no observed gross adverse effects including reductions in body weight or alterations in behaviour.

Efficacy on Tumor Growth Inhibition in Myeloma MM.1S Mouse Xenograft Models:

The mice were irradiated (200 rads) using a Co60 irradiator source. After 24 his, each mouse was inoculated subcutaneously with $5\times 10^6$ MM.1S tumor cells in 0.1 ml PBS for tumor development. Treatments were started when the tumor volume reached 100 $mm^3$. Each treatment group consisted of 10 mice. The compound of Example 1 was administrated to the tumor-bearing mice according to a specific predetermined regimen. The compound from Example 1 at dose levels of 50 mg/kg (p.o, qd×28 days) and 100 mg/kg (p.o, days 1, 3, 5/wk×4 wks) produced statically significant antitumor activity vs. control with no observed gross adverse effects including reductions in body weight or alterations in behaviour.

While the present application has been described with reference to what are presently considered to be the preferred examples, it is to be understood that the present application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Compound # | Structure | Nomenclature | Appearance | Yield (%) |
|---|---|---|---|---|
| II(b)(ii) | 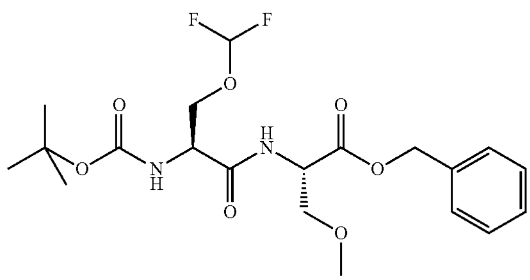 [SMILES: COC[C@H](NC(=O)[C@H](COC(F)F)NC(=O)OC(C)(C)C)C(=O)OCc1ccccc1] | Benzyl-(2S)-2-[[(2S)-2-(tert-butoxycarbonylamino)-3-(difluoromethoxy)propanoyl]-amino]-3-methoxy-propanoate | off-white powder | 71 |

$^1$H NMR (300 MHz, CDCl$_3$): δ(ppm): 7.41-7.39 (m, 5H), 7.18 (td, 1H), 6.21 (wt, 1H), 5.25-5.20 (m, 1H), 5.19 (s, 2H), 4.82 (td, 1H), 4.42 (br s, 1H), 4.31 (td, 1H), 4.20-4.15 (m, 2H), 4.01 (dd, 1H), 3.25 (s, 3H), 1.41 (s, 9H).

| | | | | |
|---|---|---|---|---|
| II(c)(ii) | | Benzyl-(2S)-2-[[(2S)-2-(tert-butoxycarbonylamino)-3-methoxy-propanoyl]amino-3-(difluoromethoxy)propanoate | off-white solid | 86 |

$^1$H NMR (300 MHz, CDCl$_3$): δ(ppm): 7.42-7.38 (m, 5H), 7.20 (td, 1H), 6.23 (wt, 1H), 5.22-5.26 (m, 1H), 5.18 (s, 2H), 4.79 (td, 1H), 4.41 (br s, 1H), 4.33 (td, 1H), 4.19-4.16 (m, 2H), 4.03 (dd, 1H), 3.26 (s, 3H), 1.43 (s, 9H).

| | | | | |
|---|---|---|---|---|
| II(d)(ii) | | Benzyl-(2S)-2-[[(2S)-2-(tert-butoxycarbonylamino)-3-(difluoromethoxy)propanoyl]amino]-4-methyl-pentanoate | white solid | 76 |

$^1$H NMR (CDCl$_3$, 400 MHz): δ 7.42-7.35 (m, 5H), 6.87-6.81 (m, 1H), 6.13 (t, J = 74 Hz, 1H), 5.22-5.17 (m, 2H), 4.89-4.77 (m, 2H), 4.33-4.25 (m, 1H), 4.18-4.09 (m, 2H), 1.75-1.61 (m, 2H), 1.54-1.39 (m, 1H), 0.99-0.87 (m, 6H).

| | | | | |
|---|---|---|---|---|
| II(e)(ii) | | Benzyl-(2S)-2-[[(2S)-2-(tert-butoxycarbonylamino)-4-methyl-pentanoyl]amino]-3-(difluoromethoxy)propanoate | clear sticky oil | 85 |

$^1$H NMR (CDCl$_3$, 400 MHz): δ 7.40-7.31 (m, 5H), 6.89-6.83 (m, 1H), 6.14 (t, J = 74 Hz, 1H), 5.24-5.18 (m, 2H), 4.87-4.79 (m, 2H), 4.32-4.26 (m, 1H), 4.18-4.09 (m, 2H), 1.73-1.62 (m, 2H), 1.53-1.40 (m, 1H), 0.98-0.88 (m, 6H).

TABLE 1-continued

| Compound # | Structure | Nomenclature | Appearance | Yield (%) |
|---|---|---|---|---|
| II(f)(ii) | 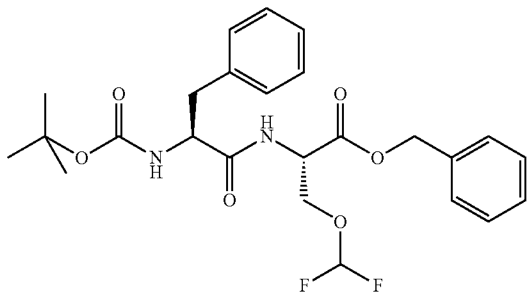 [SMILES: CC(C)(C)OC(=O)N[C@@H](Cc1ccccc1)C(=O)N[C@@H](COC(F)F)C(=O)OCc1ccccc1] | benzyl (2S)-2-[[(2S)-2-(tert-butoxycarbonylamino)-3-phenyl-propanoyl]amino]-3-(difluoromethoxy)propanoate | white solid | 94 |
| II(g)(ii) | 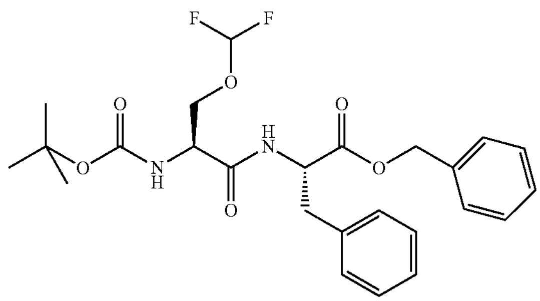 [SMILES: CC(C)(C)OC(=O)N[C@@H](COC(F)F)C(=O)N[C@@H](Cc1ccccc1)C(=O)OCc1ccccc1] | Benzyl-(2S)-2-[[(2S)-2-(tert-butoxycarbonylamino)-3-(difluoromethoxy)propanoyl]amino]-3-phenylpropanoate | white solid | 78 |

TABLE 2

| Compound # | Structure | Nomenclature | Appearance | Yield (%) |
|---|---|---|---|---|
| II(b)(i) | 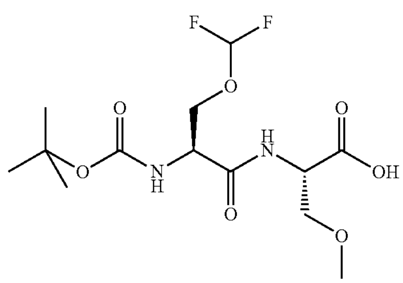 [SMILES: COC[C@H](NC(=O)[C@H](COC(F)F)NC(=O)OC(C)(C)C)C(=O)O] | (2S)-2-[[(2S)-2-(tert-butoxycarbonylamino)-3-(difluoromethoxy)propanoyl]-amino]-3-methoxypropanoic acid | off-white foam | 98 |

NMR (d$_6$-DMSO, 400 MHz): δ 8.36 (d, J = 8 Hz, 1H), 7.12 (d, J = 8 Hz, 1H), 6.63 (t, J = 76 Hz, 1H), 4.57-4.51 (m, 1H), 4.37-4.29 (m, 1H), 4.15-4.09 (m, 1H), 4.04-3.97 (m, 2H), 3.92-3.83 (m, 1H), 3.21 (s, 3H), 1.37 (s, 9H).

| II(c)(i) | 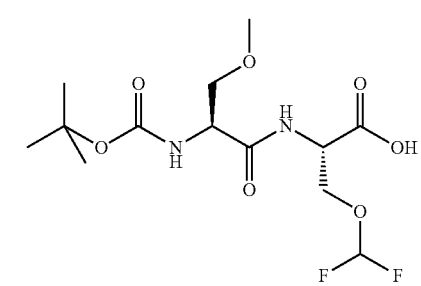 [SMILES: COC[C@H](NC(=O)OC(C)(C)C)C(=O)N[C@@H](COC(F)F)C(=O)O] | (2S)-2-[[(2S)-2-(tert-butoxycarbonylamino)-3-methoxy-propanoyl]amino]-3(difluoromethoxy)propanoic acid | clear sticky oil | 99 |

NMR (d$_6$-DMSO, 400 MHz): δ 8.33 (d, 1H), 7.14 (d, J = 8 Hz, 1H), 6.63 (t, J = 75 Hz, 1H), 4.59-4.49 (m, 1H), 4.38-4.27 (m, 1H), 4.17-4.10 (m, 1H), 4.06-3.97 (m, 2H), 3.95-3.80 (m, 1H), 3.22 (s, 3H), 1.38 (s, 9H).

TABLE 2-continued

| Compound # | Structure | Nomenclature | Appearance | Yield (%) |
|---|---|---|---|---|
| II(f)(i) | 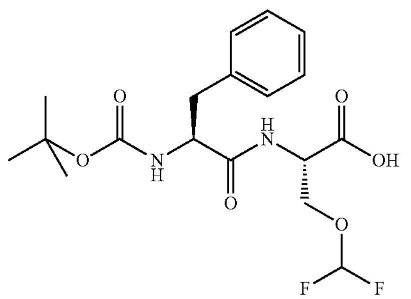 [SMILES: CC(C)(C)OC(=O)N[C@@H](Cc1ccccc1)C(=O)N[C@@H](COC(F)F)C(=O)O] | (2S)-2-[[(2S)-2-(tert-butoxycarbonylamino)-3-phenyl-propanoyl]amino]-3-(difluoromethoxy)propanoic acid | white solid | 100 |
| II(g)(i) | 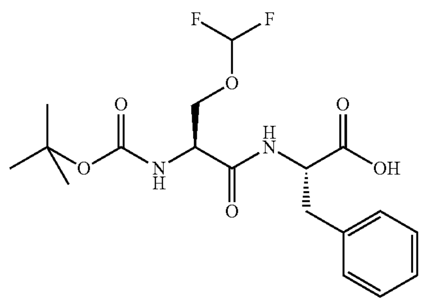 [SMILES: CC(C)(C)OC(=O)N[C@@H](COC(F)F)C(=O)N[C@@H](Cc1ccccc1)C(=O)O] | (2S)-2-[[(2S)-2-(tert-butoxycarbonylamino)-3-(difluoromethoxy)propanoyl]amino]-3-phenyl-propanoic acid | white powder | 98 |
| II(d)(i) | 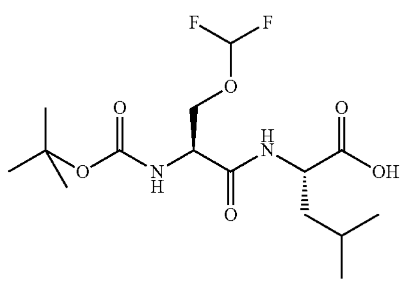 [SMILES: CC(C)C[C@H](NC(=O)[C@H](COC(F)F)NC(=O)OC(C)(C)C)C(=O)O] | (2S)-2-[[(2S)-2-(tert-butoxycarbonylamino)-3-(difluoromethoxy)propanoyl]amino]-4-methyl-pentanoic acid | off-white yellowish foam | 66 |

$^1$H NMR (d$_6$-DMSO, 400 MHz): 8.35 (d, 1H), 6.11 (t, J = 74 Hz, 1H), 5.17-5.05 (m, 1H), 4.79-4.71 (m, 1H), 4.29-4.16 (m, 1H), 4.11-4.01 (m, 1H), 1.68-1.52 (m, 2H), 1.50-1.27 (m, 1H), 1.38 (s, 9H), 0.91-0.83 (m, 6H).

| Compound # | Structure | Nomenclature | Appearance | Yield (%) |
|---|---|---|---|---|
| II(e)(i) | | (2S)-2-[[(2S)-2-(tert-butoxycarbonylamino)-4-methyl-pentanoyl]amino]-3-(difluoromethoxy)propanoic acid | clear oil | 85 |

$^1$H NMR (d$_6$-DMSO, 400 MHz): 8.37 (d, 1H), 6.13 (t, J = 74 Hz, 1H), 5.15-5.01 (m, 1H), 4.81-4.75 (m, 1H), 4.28-4.15 (m, 1H), 4.13-4.02 (m, 1H), 1.71-1.55 (m, 2H), 1.52-1.26 (m, 1H), 1.38 (s, 9H), 0.94-0.82 (m, 6H).

TABLE 3

| Compound # | Structure | Formula and Nomenclature | Appearance | Yield (%) |
|---|---|---|---|---|
| XIV(b) | 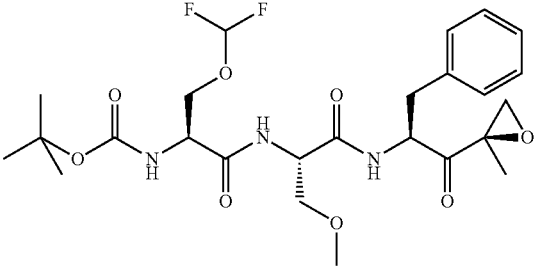 [SMILES: COC[C@H](NC(=O)[C@H](COC(F)F)NC(=O)OC(C)(C)C)C(=O)N[C@@H](Cc1ccccc1)C(=O)[C@@]1(C)CO1] | $C_{25}H_{35}F_2N_3O_8$<br>((S)-1-{(S)-1-[(S)-1-Benzyl-2-((R)-2-methyl-oxiranyl)-2-oxo-ethylcarbamoyl]-2-methoxyethylcarbamoyl}-2-difluoromethoxyethyl)-carbamic acid tert-butyl ester | off-white solid | 85 |

$^1$H-NMR (300 MHz, CDCl$_3$): δ 7.21-7.35 (m, 3H), 7.18 (dd, 2H), 6.80 (wd, 1H), 6.72 (wd, 1H), 6.21 (w t, 1H), 5.29 (br s, 1H), 4.79 (td, 1H), 4.58 (td, 1H), 4.36 (m, 1H), 4.35-4.12 (m, 2H), 4.10 (dd, 1H), 3.87 (dd, 1H), 3.26 (d, 1H), 3.25 (s, 3H), 3.14 (dd, 1H), 2.87 (d, 1H), 2.87 (dd, 1H), 1.49 (s, 3H), 1.43 (s, 9H).

| Compound # | Structure | Formula and Nomenclature | Appearance | Yield (%) |
|---|---|---|---|---|
| XIV(c) | 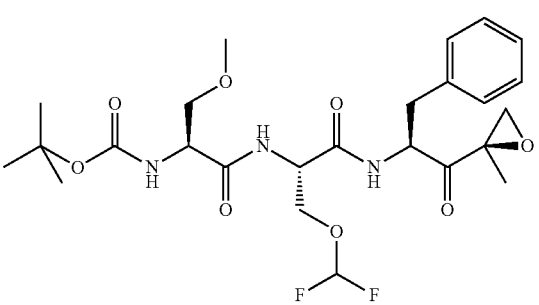 [SMILES: COC[C@H](NC(=O)OC(C)(C)C)C(=O)N[C@@H](COC(F)F)C(=O)N[C@@H](Cc1ccccc1)C(=O)[C@@]1(C)CO1] | $C_{25}H_{35}F_2N_3O_8$<br>((S)-1-{(S)-1-[(S)-1-Benzyl-2((R)-2-methyl-oxiranyl)-2-oxo-ethylcarbamoyl]-2-difluoromethoxyethylcarbamoyl}-2-methoxyethyl)-carbamic acid tert-butyl ester | off-white powder | 83 |

$^1$H-NMR (300 MHz, CDCl$_3$): δ 7.20-7.28 (m, 3H), 7.20 (dd, 2H), 6.83 (wd, 1H), 6.75 (wd, 1H), 6.71 (w t, 1H), 5.27 (br s, 1H), 4.81 (td, 1H), 4.60 (td, 1H), 4.38 (m, 1H), 4.38-4.09 (m, 2H), 4.12 (dd, 1H), 3.91 (dd, 1H), 3.29 (d, 1H), 3.26 (s, 3H), 3.16 (dd, 1H), 2.84 (d, 1H), 2.81 (dd, 1H), 1.50 (s, 3H), 1.41 (s, 9H).

| Compound # | Structure | Formula and Nomenclature | Appearance | Yield (%) |
|---|---|---|---|---|
| XIV(d) | 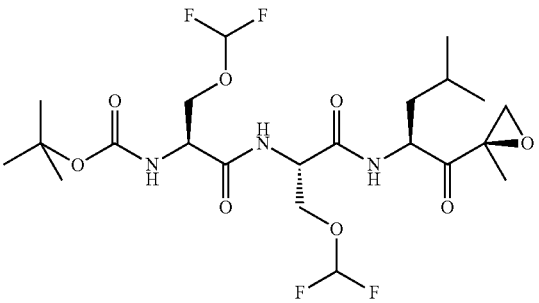 [SMILES: CC(C)C[C@H](NC(=O)[C@H](COC(F)F)NC(=O)[C@H](COC(F)F)NC(=O)OC(C)(C)C)C(=O)[C@@]1(C)CO1] | $C_{22}H_{35}FN_3O_8$<br>(S)-2-Difluoromethoxy-1-{(S)-2-difluoromethoxy-1-[(S)-3-methyl-1-((R)-2-methyl-oxiranecarbonyl)-butylcarbamoyl]-ethylcarbamoyl}-ethyl)-carbamic acid tert-butyl ester | off-white powder | 99 |

$^1$H-NMR (CDCl$_3$, 300 MHz): δ 7.02 (d, J = 6 Hz, 1H), 6.74-6.64 (m, 1H), 6.25 (t, J = 75 Hz, 1H), 6.21 (t, J = 75 Hz, 1H), 5.34-5.24 (m, 1H), 4.69-4.58 (m, 3H), 4.44-4.24 (m, 4H), 4.10-4.04 (m, 1H), 3.99-3.92 (m, 1H), 3.24 (d, J = 6 Hz, 1H), 2.91-2.87 (m, 2H), 1.82-1.72 (m, 1H), 1.51 (s, 3H), 1.46 (s, 9H), 0.96-0.90 (m, 6H).

| Compound # | Structure | Formula and Nomenclature | Appearance | Yield (%) |
|---|---|---|---|---|
| XIV(e) | 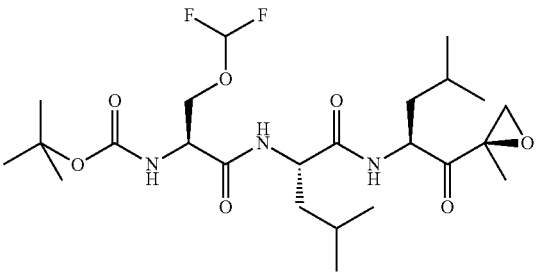 [SMILES: CC(C)C[C@H](NC(=O)[C@H](COC(F)F)NC(=O)OC(C)(C)C)C(=O)N[C@@H](CC(C)C)C(=O)[C@@]1(C)CO1] | $C_{24}H_{41}F_2N_3O_7$<br>((S)-2-Difluoromethoxy-1-{(S)-3-methyl-1-[(S)-3-methyl-1-((R)-2-methyl-oxiranecarbonyl)-butylcarbamoyl]-butylcarbamoyl}-ethyl)-carbamic acid tert-butyl ester | white powder | 70 |

NMR (CDCl$_3$, 300 MHz): δ 6.98 (d, 1H), 6.74-6.64 (m, 1H), 6.22 (t, J = 75 Hz, 1H), 5.33-5.24 (m, 1H), 4.69-4.58 (m, 3H), 4.44-4.24 (m, 4H), 4.10-4.04 (m, 1H), 3.99-3.92 (m, 1H), 3.21 (d, J = 6 Hz, 1H), 2.94-2.85 (m, 2H), 1.80-1.69 (m, 1H), 1.50 (s, 3H), 1.43 (s, 9H), 1.01-0.89 (m, 12H).

TABLE 3-continued

| Compound # | Structure | Formula and Nomenclature | Appearance | Yield (%) |
|---|---|---|---|---|
| XIV(f) | 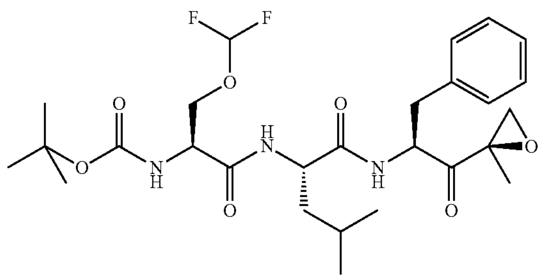 [SMILES: CC(C)C[C@H](NC(=O)[C@H](COC(F)F)NC(=O)OC(C)(C)C)C(=O)N[C@@H](Cc1ccccc1)C(=O)[C@@]1(C)CO1] | C₂₇H₃₉F₂N₃O₇ ((S)-1-{(S)-1-[(S)-1-Benzyl-2-((R)-2-methyl-oxiranyl)-2-oxo-ethylcarbamoyl]-3-methyl-butylcarbamoyl}-2-difluoromethoxyethyl)-carbamic acid tert-butyl ester | off-white powder | 82 |

¹H NMR (300 MHz, CDCl₃): δ(ppm): 7.32-7.20 (m, 3H), 7.13 (dd, 2H), 6.82 (wd, 1H), 6.70 (wd, 1H), 6.51 (w t, 1H), 6.25 (t, J = 75 Hz, 1H), 5.26 (br s, 1H), 4.86 (td, 1H), 4.58 (td, 1H), 4.36 (m, 1H), 4.32-4.08 (m, 2H), 4.01 (dd, 1H), 3.90 (dd, 1H), 3.24 (d, 1H), 3.12 (dd, 1H), 2.90 (d, 1H), 2.85 (dd, 1H), 1.81-1.70 (m, 1H), 1.50 (s, 3H), 1.43 (s, 9H), 1.03-0.88 (m, 6H).

| | | | | |
|---|---|---|---|---|
| XIV(g) | | C₂₇H₃₉F₂N₃O₇ ((S)-1-{(S)-1-[(S)-1-Benzyl-2-((R)-2-methyl-oxiranyl)-2-oxo-ethylcarbamoyl]-2-difluoromethoxy-ethylcarbamoyl}-3-methylbutyl)-carbamic acid tert-butyl ester | off-white powder | 87 |

¹H NMR (300 MHz, CDCl₃): δ(ppm): 7.34-7.21 (m, 3H), 7.12 (dd, 2H), 6.79 (wd, 1H), 6.73 (wd, 1H), 6.49 (wt, 1H), 6.24 (t, J = 75 Hz, 1H), 5.24 (br s, 1H), 4.83 (td, 1H), 4.55 (td, 1H), 4.38 (m, 1H), 4.35-4.03 (m, 2H), 4.06 (dd, 1H), 3.88 (dd, 1H), 3.25 (d, 1H), 3.11 (dd, 1H), 2.89 (d, 1H), 2.83 (dd, 1H), 1.84-1.75 (m, 1H), 1.52 (s, 3H), 1.42 (s, 9H), 1.02-0.91 (m, 6H).

| | | | | |
|---|---|---|---|---|
| XIV(h) | | C₂₄H₄₁F₂N₃O₇ ((S)-1-{(S)-2-Difluoromethoxy-1-[(S)-3-methyl-1-((R)-2-methyl-oxiranecarbonyl)-butylcarbamoyl]-ethylcarbamoyl}-3-methylbutyl)-carbamic acid tert-butyl ester | off-white powder | 67 |

¹H NMR (300 MHz, CDCl₃): δ(ppm): 6.81 (wd, 1H), 6.72 (wd, 1H), 6.51 (wt, 1H), 6.25 (t, J = 75 Hz, 1H), 5.24 (br s, 1H), 4.83 (td, 1H), 4.55 (td, 1H), 4.38 (m, 1H), 4.35-4.03 (m, 2H), 4.06 (dd, 1H), 3.88 (dd, 1H), 3.25 (d, 1H), 3.11 (dd, 1H), 2.89 (d, 1H), 2.83 (dd, 1H), 1.80-1.71 (m, 2H), 1.52 (s, 3H), 1.42 (s, 9H), 1.05-0.93 (m, 12H).

TABLE 4

| Compound # | Structure | Formula and Nomenclature | Appearance | Yield (%) |
|---|---|---|---|---|
| XV(b) | 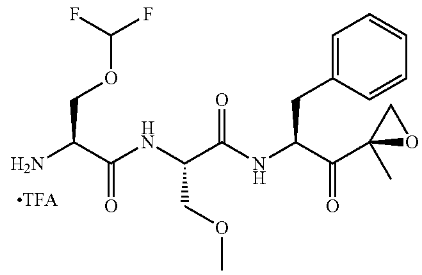 [SMILES: COC[C@H](NC(=O)[C@@H](N)COC(F)F)C(=O)N[C@@H](Cc1ccccc1)C(=O)[C@@]1(C)CO1] | $C_{20}H_{27}F_2N_3O_6$ (free base) (S)-2-Amino-N-{(S)-1-[(S)-1-benzyl-2-((R)-2-methyl-oxiranyl)-2-oxo-ethylcarbamoyl]-2-methoxyethyl}-3-difluoromethoxypropionamide | off-yellow solid | 98 |

$^1$H NMR (300 MHz, d$_6$-DMSO): δ(ppm): 7.39-7.25 (m, 3H), 7.24 (dd, 2H), 6.87 (wd, 1H), 6.66 (wd, 1H), 6.55 (br s, 1H), 6.13 (w t, 1H), 6.02 (wt, 1H), 5.15 (br s, 1H), 4.81 (td, 1H), 4.49 (td, 1H), 4.32 (m, 1H), 4.93-3.31 (m, 2H), 3.99 (dd, 1H), 3.88 (dd, 1H), 3.55 (s, 3H). 3.21 (d, 1H), 3.12 (dd, 1H), 2.81 (d, 1H), 2.78 (dd, 1H), 1.43 (s, 3H).

| Compound # | Structure | Formula and Nomenclature | Appearance | Yield (%) |
|---|---|---|---|---|
| XV(c) | | $C_{20}H_{27}F_2N_3O_6$ (free base) (S)-2-Amino-N-{(S)-1-[(S)-1-benzyl-2-((R)-2-methyl-oxiranyl)-2-oxo-ethylcarbamoyl]-2-difluoromethoxyethyl}-3-methoxypropionamide | off-yellow solid | 85 |

$^1$H NMR (300 MHz, d$_6$-DMSO): δ(ppm): 7.33-7.27 (m, 3H), 7.25 (dd, 2H), 6.87 (d, 1H), 6.59 (wd, 1H), 6.57 (br s, 1H), 6.09 (w t, 1H), 6.11 (t, 1H), 5.21 (br s, 1H), 4.76 (td, 1H), 4.52 (td, 1H), 4.41 (m, 1H), 4.33-3.98 (m, 2H), 3.95 (dd, 1H), 3.89 (dd, 1H), 3.51 (s, 3H). 3.18 (d, 1H), 3.09 (dd, 1H), 2.83 (d, 1H), 2.76 (dd, 1H), 1.44 (s, 3H).

| Compound # | Structure | Formula and Nomenclature | Appearance | Yield (%) |
|---|---|---|---|---|
| XV(d) | | $C_{17}H_{27}F_4N_3O_6$ (free base) (S)-2-Amino-3-difluoromethoxy-N-{(S)-2-difluoromethoxy-1-[(S)-3-methyl-1-((R)-2-methyloxiranecarbonyl)-butylcarbamoyl]-ethyl}-propionamide | sticky yellow powder | 73 |

$^1$H NMR (300 MHz, d$_6$-DMSO): δ(ppm): 6.97 (d, 1H), 6.69-6.65 (m, 1H), 6.45 (br. s, 2H), 6.16 (t, J = 75 Hz, 1H), 6.13 (t, J = 75 Hz, 1H), 5.35-5.26 (m, 1H), 4.69-4.58 (m, 3H), 4.44-4.24 (m, 4H), 4.10-4.04 (m, 1H), 3.99-3.92 (m, 1H), 3.24 (d, J = 6 Hz, 1H), 2.91-2.87 (m, 2H), 1.72-1.69 (m, 1H), 1.49 (s, 3H), 0.94-0.91 (m, 6H).

| Compound # | Structure | Formula and Nomenclature | Appearance | Yield (%) |
|---|---|---|---|---|
| XV(e) | | $C_{19}H_{33}F_2N_3O_5$ (free base) (S)-2((S)-2-Amino-3-difluoromethoxy-propionylamino)-4-methyl-pentanoic acid [(S)-3-methyl-1((R)-2-methyloxiranecarbonyl)-butyl]amide | white powder | 65 |

$^1$H NMR (300 MHz, d$_6$-DMSO): δ(ppm): 6.89 (d, 1H), 6.70-6.59 (m, 1H), 6.55 (br. s, 2H), 6.17, (t, J = 75 Hz, 1H), 5.35-5.24 (m, 1H), 4.71-4.63 (m, 3H), 4.51-4.53 (m, 4H), 4.13-4.01 (m, 1H), 3.97-3.91 (m, 1H), 3.23 (d, 1H), 2.98-2.81 (m, 2H), 1.78-1.65 (m, 1H), 1.48 (s, 3H), 0.98-0.83 (m, 12H).

TABLE 4-continued

| Compound # | Structure | Formula and Nomenclature | Appearance | Yield (%) |
|---|---|---|---|---|
| XV(f) | [structure] | $C_{22}H_{31}F_2N_3O_5$ (free base) (S)-2-((S)-2-Amino-3-difluoromethoxy-propionylamino)-4-methyl-pentanoic acid [(S)-1-benzyl-2-((R)-2-methyloxiranyl)-2-oxo-ethyl]-amide | off-white powder | 62 |

$^1$H NMR (300 MHz, $d_6$-DMSO): δ(ppm): 7.29-7.18 (m, 3H), 7.09 (dd, 2H), 6.74 (wd, 1H), 6.67 (br. s, 2H), 6.65 (d, 1H), 6.48 (t, 1H), 6.19 (t, J = 75 Hz, 1H), 5.21 (br s, 1H), 4.77 (td, 1H), 4.51 (td, 1H), 4.38-4.34 (m, 1H), 4.19-4.05 (m, 2H), 3.99 (dd, 1H), 3.95-3.92 (m, 1H), 3.18 (d, 1H), 3.14-3.16 (m, 1H), 2.85 (d, 1H), 2.75-7.62 (m, 1H), 1.77-1.69 (m, 1H), 1.48 (s, 3H), 0.97-0.86 (m, 6H).

| | | | | |
|---|---|---|---|---|
| XV(g) | [structure] | $C_{22}H_{31}F_2N_3O_5$ (free base) (S)-2-Amino-4-methyl-pentanoic acid {(S)-1-[(S)-1-benzyl-2-((R)-2-methyloxiranyl)-2-oxo-ethylcarbamoyl]-2-difluoromethoxyethyl}-amide | off-white powder | 76 |

$^1$H NMR (300 MHz, $d_6$-DMSO): δ(ppm): 7.31-7.19 (m, 3H), 7.11 (dd, 2H), 6.76-6.68 (m, 1H), 6.52 (br. s, 2H), 6.49 (d, 1H), 6.45 (t, 1H), 6.21 (t, J = 75 Hz, 1H), 5.18 (br. s, 1H), 4.76-4.68 (m, 1H), 4.54-4.49 (m, 1H), 4.29-4.25 (m, 1H), 4.15-4.01 (m, 2H), 3.98-3.91 (m, 1H), 3.87-3.82 (m, 1H), 3.15 (d, 1H), 3.15-3.11 (m, 1H), 2.76 (d, 1H), 2.77-7.60 (m, 1H), 1.89-1.78 (m, 1H), 1.47 (s, 3H), 0.98-0.87 (m, 6H).

| | | | | |
|---|---|---|---|---|
| XV(h) | [structure] | $C_{19}H_{33}F_2N_3O_5$ (S)-2-Amino-4-methyl-pentanoic acid {(S)-2-difluoromethoxy-1-[(S)-3-methyl-1-((R)-2-methyloxiranecarbonyl)-butylcarbamoyl]-ethyl}-amide | off-white powder | 89 |

$^1$H NMR (300 MHz, $d_6$-DMSO): δ(ppm): 6.92 (wd, 1H), 6.72 (wd, 1H), 6.55-6.50 (m, 1H), 6.15 (t, J = 75 Hz, 1H), 5.09 (br. s, 1H), 4.81-4.78 (m, 1H), 4.57-4.52 (m, 1H), 4.28-4.19 (m, 1H), 4.17-4.02 (m, 2H), 3.99-3.87 (m, 1H), 3.73 (dd, 1H), 3.17 (d, 1H), 3.07 (dd, 1H), 2.75 (d, 1H), 2.81-2.77 (m, 1H), 1.73-1.69 (m, 2H), 1.49 (s, 3H), 0.98-0.91 (m, 12H).

TABLE 5

| Example # | Structure | Nomenclature | Appearance | Yield (%) |
|---|---|---|---|---|
| 2 | [structure] | 2-Methyl-thiazole-5-carboxylic acid-((S)-1-{(S)-1-[(S)-1-benzyl-2((R)-2-methyl-oxiranyl)-2-oxo-ethylcarbamoyl]-2-methoxy-ethylcarbamoyl}-2-difluoromethoxyethyl)-amide | white yellowish powder | 73 |

TABLE 5-continued

| Example # | Structure | Nomenclature | Appearance | Yield (%) |
|---|---|---|---|---|
| | ¹H NMR (300 MHz, CDCl₃): δ(ppm): 8.06 (s, 1H), 7.27-7.24 (m, 3H), 7.18 (dd, 2H), 6.79 (d, 1H), 6.77 (d, 1H), 6.64 (d, 1H), 6.13 (wt, 1H), 4.87-4.67 (m, 2H), 4.58 (td, 1H), 4.32 (dd, 1H), 4.27 (dd, 1H), 4.02 (td, 1H), 3.91 (dd, 1H), 3.30 (s, 3H), 3.27 (d, 1H), 3.28 (dd, 1H), 3.16 (d, 1H), 2.88 (dd, 1H), 2.83 (dd, 1H), 2.74 (s, 3H), 1.46 (s, 3H). | | | |
| 3 | 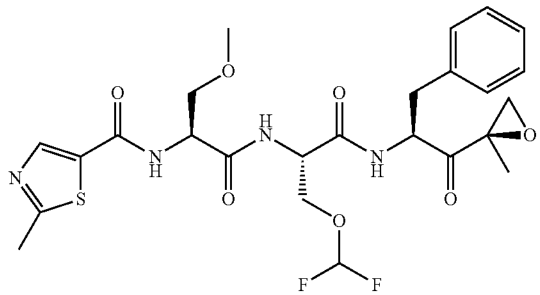 [SMILES: COC[C@H](NC(=O)c1cnc(C)s1)C(=O)N[C@@H](COC(F)F)C(=O)N[C@@H](Cc1ccccc1)C(=O)[C@@]1(C)CO1] | 2-Methyl-thiazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-methoxyethyl)-amide | off-white powder | 65 |
| | ¹H NMR (300 MHz, CDCl₃): δ(ppm): 8.07 (s, 1H), 7.28-7.26 (m, 3H), 7.15 (dd, 2H), 6.81 (d, 1H), 6.82 (d, 1H), 6.71 (d, 1H), 6.21 (wt, 1H), 4.91-4.82 (m, 2H), 4.62 (td, 1H), 4.38 (dd, 1H), 4.31 (dd, 1H), 4.05 (td, 1H), 3.99 (dd, 1H), 3.29 (s, 3H), 3.27 (d, 1H), 3.25 (dd, 1H), 3.15 (d, 1H), 2.91 (dd, 1H), 2.79 (dd, 1H), 2.71 (s, 3H), 1.49 (s, 3H). | | | |
| 4 | 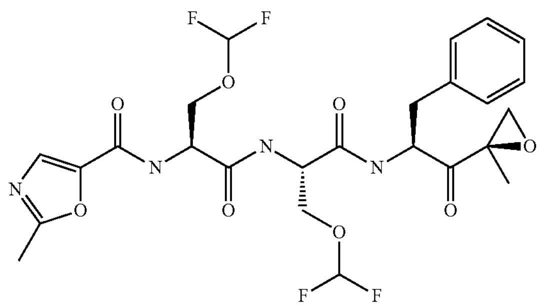 [SMILES: Cc1ncc(C(=O)N[C@@H](COC(F)F)C(=O)N[C@@H](COC(F)F)C(=O)N[C@@H](Cc2ccccc2)C(=O)[C@@]2(C)CO2)o1] | 2-Methyl-oxazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-difluoromethoxyethyl)-amide | off-white powder | 45 |
| | ¹H NMR (300 MHz, CDCl₃): δ(ppm): 8.05 (s, 1H), 7.30-7.27 (m, 3H), 7.18 (dd, 2H), 6.79 (d, 1H), 6.76 (d, 1H), 6.63 (d, 1H), 6.16 (wt, 1H), 6.10 (wt, 1H), 4.88-4.61 (m, 2H), 4.58 (td, 1H), 4.31 (dd, 1H), 4.22 (dd, 1H), 4.01 (td, 1H), 3.89 (dd, 1H), 3.26 (d, 1H), 3.24 (dd, 1H), 3.14 (d, 1H), 2.85 (dd, 1H), 2.85 (dd, 1H), 2.68 (s, 3H), 1.43 (s, 3H). | | | |
| 5 | 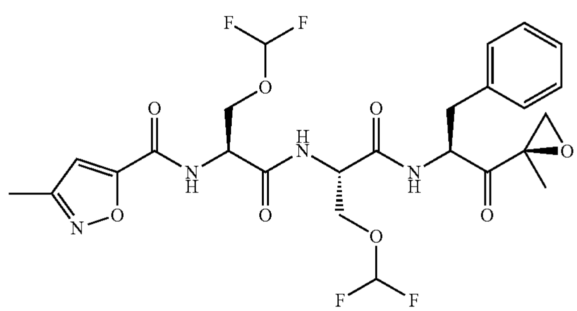 [SMILES: Cc1cc(C(=O)N[C@@H](COC(F)F)C(=O)N[C@@H](COC(F)F)C(=O)N[C@@H](Cc2ccccc2)C(=O)[C@@]2(C)CO2)on1] | 3-Methyl-isoxazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-difluoromethoxyethyl)-amide | white solid | 75 |
| | ¹H NMR (300 MHz, CDCl₃): δ(ppm): 7.87 (s, 1H), 7.31-7.28 (m, 3H), 7.18 (dd, 2H), 6.79 (d, 1H), 6.76 (d, 1H), 6.63 (d, 1H), 6.14 (wt, 1H), 6.14 (wt, 1H), 4.78-4.55 (m, 2H), 4.55 (td, 1H), 4.29 (dd, 1H), 4.19 (dd, 1H), 4.02 (td, 1H), 3.91 (dd, 1H), 3.24 (d, 1H), 3.24 (dd, 1H), 3.14 (d, 1H), 2.85 (dd, 1H), 2.78 (dd, 1H), 2.45 (s, 3H), 1.45 (s, 3H). | | | |
| 6 | 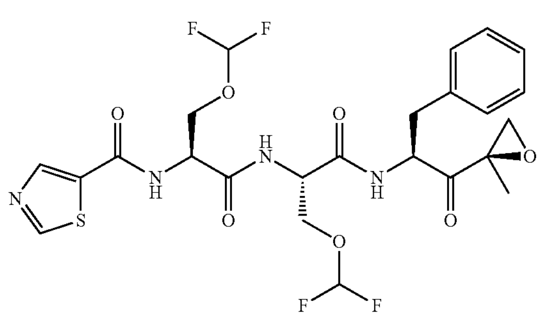 [SMILES: C[C@]1(C(=O)[C@H](Cc2ccccc2)NC(=O)[C@H](COC(F)F)NC(=O)[C@H](COC(F)F)NC(=O)c2cncs2)CO1] | Thiazole-5-carboxylic acid ((S)-1-{(S)-1-[(S)-1-benzyl-2-((R)-2-methyloxiranyl)-2-oxoethylcarbamoyl]-2-difluoromethoxyethyl carbamoyl}-2-difluoromethoxyethyl)amide | off-white yellowish powder | 63 |

TABLE 5-continued

| Example # | Structure | Nomenclature | Appearance | Yield (%) |
|---|---|---|---|---|
| | ¹H NMR (300 MHz, CDCl₃): δ(ppm): 9.35 (s, 1H), 7.31-7.27 (m, 4H), 7.18 (dd, 2H), 6.92 (d, 1H), 6.79 (d, 1H), 6.66 (d, 1H), 6.21 (wt, 1H), 6.16 (wt, 1H), 4.92-4.71 (m, 2H), 4.68 (td, 1H), 4.28 (dd, 1H), 4.19 (dd, 1H), 4.02 (td, 1H), 3.95 (dd, 1H), 3.28 (d, 1H), 3.25 (dd, 1H), 3.13 (d, 1H), 2.88 (dd, 1H), 2.77 (dd, 1H), 1.43 (s, 3H). | | | |
| 7 | [structure] | Oxazole-5-carboxylic acid ((S)-1-{(S)-1-[(S)-1-benzyl-2-((R)-2-methyloxiranyl)-2-oxo-ethylcarbamoyl]-2-difluoromethoxy-ethylcarbamoyl}-2-difluoromethoxyethyl)-amide | off-white powder | 43 |
| | ¹H NMR (300 MHz, CDCl₃): δ(ppm): 8.89 (s, 1H), 7.38-7.25 (m, 4H), 7.15 (dd, 2H), 6.88 (d, 1H), 6.77 (d, 1H), 6.63 (d, 1H), 6.18 (wt, 1H), 6.13 (wt, 1H), 4.83-4.69 (m, 2H), 4.59 (td, 1H), 4.28 (dd, 1H), 4.23 (dd, 1H), 4.05 (td, 1H), 3.98 (dd, 1H), 3.31 (d, 1H), 3.28 (dd, 1H), 3.09 (d, 1H), 2.95 (dd, 1H), 2.89 (dd, 1H), 1.41 (s, 3H). | | | |
| 8 | [structure] | 5-Methyl-thiophene-2-carboxylic acid ((S)-1-{(S)-1-[(S)-1-benzyl-2-((R)-2-methyl-oxiranyl)-2-oxo-ethylcarbamoyl]-2-difluoro-methoxyethylcarbamoyl}-2-difluoromethoxyethyl)-amide | yellow powder | 36 |
| | ¹H NMR (300 MHz, CDCl₃): δ(ppm): 7.95 (s, 1H), 7.76 (s, 1H), 7.36-7.28 (m, 3H), 7.21 (dd, 2H), 6.90 (d, 1H), 6.81 (d, 1H), 6.72 (d, 1H), 6.21 (wt, 1H), 6.22 (wt, 1H), 4.89-4.68 (m, 2H), 4.63 (td, 1H), 4.25 (dd, 1H), 4.14 (dd, 1H), 4.04 (td, 1H), 3.87 (dd, 1H), 3.33 (d, 1H), 3.28 (dd, 1H), 3.18 (d, 1H), 2.81 (dd, 1H), 2.77 (dd, 1H), 2.51 (s, 3H). 1.41 (s, 3H). | | | |
| 9 | [structure] | 5-Methyl-furan-2-carboxylic acid ((S)-1-{(S)-1-[(S)-1-benzyl-24(R)-2-methyloxiranyl)-2-oxo-ethylcarbamoyl1-2-difluoromethoxyethylcarba-moyl}-2-difluoromethoxyethyl)-amide | off-white powder | 69 |
| | ¹H NMR (300 MHz, CDCl₃): δ(ppm): 7.73 (s, 1H), 7.74 (s, 1H), 7.37-7.25 (m, 3H), 7.18 (dd, 2H), 6.87 (d, 1H), 6.78 (d, 1H), 6.69 (d, 1H), 6.22 (wt, 1H), 6.19 (wt, 1H), 4.93-4.72 (m, 2H), 4.71 (td, 1H), 4.29 (dd, 1H), 4.18 (dd, 1H), 4.03 (td, 1H), 3.96 (dd, 1H), 3.41 (d, 1H), 3.34 (dd, 1H), 3.21 (d, 1H), 2.99 (dd, 1H), 2.75 (dd, 1H), 2.46 (s, 3H). 1.42 (s, 3H). | | | |
| 10 | [structure] | Thiophene-2-carboxylic acid ((S)-1-{(S)-1-[(S)-1-benzyl-2-((R)-2-methyloxiranyl)-2-oxo-ethylcarbamoyl]-2-difluoromethoxy-ethylcarbamoyl}-2-difluoromethoxyethyl)-amide | off-white powder | 74 |

TABLE 5-continued

| Example # | Structure | Nomenclature | Appearance | Yield (%) |
|---|---|---|---|---|
| | ¹H NMR (300 MHz, CDCl₃): δ(ppm): 7.95 (d, 1H), 7.77-158 (m, 2H), 7.38-7.26 (m, 3H), 7.19 (dd, 2H), 6.88 (d, 1H), 6.79 (d, 1H), 6.68 (d, 1H), 6.18 (wt, 1H), 6.19 (wt, 1H), 4.91-4.72 (m, 2H), 4.58 (td, 1H), 4.17 (dd, 1H), 4.11 (dd, 1H), 4.01 (td, 1H), 3.91 (dd, 1H), 3.36 (d, 1H), 3.22 (dd, 1H), 3.13 (d, 1H), 2.91 (dd, 1H), 2.68 (dd, 1H), 1.45 (s, 3H). | | | |
| 11 | [structure] | N-[(1S)-2-[[(1S)-2-[[(1S)-1-benzyl-2-[(2R)-2-methyloxiran-2-yl]-2-oxo-ethyl]amino]-1(difluoromethoxymethyl)-2-oxo-ethyl]amino]-1-(difluoromethoxymethyl)-1-(difluoromethyl)-2-oxo-ethyl]-1H-1,2,4-triazole-5-carboxamide | white powder | 6 |
| | ¹H NMR (300 MHz, d₆-DMSO): δ(ppm): 8.58 (d, J = 4 HZ, 1H), 8.49 (d, J = 8 Hz, 1H), 7 29-7.16 (m, 6H), 6.61 (d, J = 76 Hz, 1H), 6.60 (d, J = 76 Hz, 1H), 4.83-4.76 (m, 1H), 4.63-4.54 (m, 2H), 4.14-4.08 (m, 2H), 3.99-3.85 (m, 2H), 3.18 (d, J = 6 Hz, 1H), 2.99-2.91 (m, 2H), 2.73-2.64 (m, 1H), 1.34 (s, 3H). | | | |
| 12 | [structure] | N-[(1S)-1-(difluoromethoxymethyl)-2-[[(1S)-1-(difluoromethoxymethyl)-2-[[(1S)-3-methyl-1-[(2R)-2-methyloxirane-2-carbonyl]butyl]amino]-2-oxo-ethyl]amino]-2-oxo-ethyl]-2-methylthiazole-5-carboxamide | white powder | 75 |
| | ¹H NMR (300 MHz, d₆-DMSO): δ(ppm): 8.88 (d, J = 4 Hz, 1H), 8.50 (d, J = 4 Hz, 1H), 8.34-8.28 (m, 2H), 6.65 (t, J = 76 Hz, 1H), 6.61 (t, J = 76 Hz, 1H), 4.83-4.74 (m, 1H), 4.58-4.49 (m, 1H), 4.40-4.31 (m, 1H), 4.15-4.08 (m, 1H), 4.05-3.88 (m, 3H), 3.12 (d, J = 4 Hz, 1H), 2.98 (d, J = 4 Hz, 1H), 2.65 (s, 3H), 1.67-1.55 (m, 1H), 1.38 (s, 3H), 1.35-1.22 (m, 2H), 0.86 (d, J = 6 Hz, 3H), 0.81 (d, J = 6 Hz, 3H). | | | |
| 13 | [structure] | Pyridine-2-carboxylic acid ((S)-1-((S)-1-[(S)-1-benzyl-2-((R)-2-methyloxiranyl)-2-oxo-ethylcarbamoyl]-2-difluoromethoxy-ethylcarbamoyl}-2-difluoromethoxyethyl)-amide | white powder | 86 |
| | ¹H NMR (300 MHz, d₆-DMSO): δ(ppm): 8.39 (d, 1H), 7.45-7.35 (m, 2H), 7.31-7.14 (m, 6H), 6.59 (wt, J = 75 Hz, 1H), 6.57 (wt, J = 76 Hz, 1H), 4.85-4.78 (m, 1H), 4.71-4.56 (m, 2H), 4.12-4.05 (m, 2H), 4.01-3.87 (m, 2H), 3.19-3.14 (m, 1H), 3.02-2.94 (m, 2H), 2.68-2.58 (m, 1H), 1.36 (s, 3H). | | | |
| 14 | [structure] | N-((S)-1-{(S)-1-[(S)-1-Benzyl-2-((R)-2-methyl-oxiranyl)-2-oxo-ethylcarbamoyl]-2-difluoromethoxyethylcarbamoyl}-2-difluoromethoxyethyl)-nicotinamide | white powder | 77 |

TABLE 5-continued

| Example # | Structure | Nomenclature | Appearance | Yield (%) |
|---|---|---|---|---|
| | ¹H NMR (300 MHz, d₆-DMSO): δ(ppm): 8.33 (s, 1H), 8.28 (dd, 1H), 7.38-7.29 (m, 2H), 7.29-7.17 (m, 5H), 6.62 (wt, J = 75 Hz, 1H), 6.59 (wt, J = 76 Hz, 1H), 4.78-4.67 (m, 1H), 4.83-4.59 (m, 2H), 4.15-4.03 (m, 2H), 3.98-3.83 (m, 2H), 3.21-3.15 (m, 1H), 2.99-2.91 (m, 2H), 2.70-2.56 (m, 1H), 1.35 (s, 3H). | | | |
| 15 | [structure] | Pyridine-2-carboxylic acid ((S)-1-{(S)-1-[[(S)-1-benzyl-2-((R)-2-methyloxiranyl)-2-oxo-ethylcarbamoyl]-2-difluoromethoxy-ethylcarbamoyl}-2-difluoromethoxy-ethyl)-amide | white yellowish powder | 61 |
| | ¹H NMR (300 MHz, d6-DMSO): δ(ppm): 8.65 (s, 1H), 8.41-8.35 (m, 2H), 7.27-7.16 (m, 5H), 6.61 (wt, J = 75 Hz, 1H), 6.58 (wt, J = 76 Hz, 1H), 4.81-4.69 (m, 1H), 4.82-4.57 (m, 2H), 4.21-4.04 (m, 2H), 3.99-3.79 (m, 2H), 3.25-3.18 (m, 1H), 2.99-2.91 (m, 2H), 2.69-2.54 (m, 1H), 1.37 (s, 3H). | | | |
| 16 | [structure] | N-[(1S)-2-[[(1S)-2-{{(1S)-1-benzyl-2-[(2R)-2-methyloxiran-2-yl]-2-oxo-ethyl]amino]-1-(difluoromethoxymethyl)-2-oxo-ethyl]amino]-1-(difluoromethoxymethyl)-2-oxo-ethyl]-pyrimidine-2-carboxamide | white yellowish powder | 56 |
| | ¹H NMR (300 MHz, d₆-DMSO): δ(ppm): 8.55-7.58 (m, 2H), 7.55-745 (m, 1H), 7.29-7.18 (m, 5H), 6.59 (wt, J = 75 Hz, 1H), 6.57 (wt, J = 76 Hz, 1H), 4.78-4.65 (m, 1H), 4.80-4.61 (m, 2H), 4.17-4.01 (m, 2H), 4.02-3.85 (m, 2H), 3.23-3.17 (m, 1H), 2.98-2.87 (m, 2H), 2.70-2.55 (m, 1H), 1.35 (s, 3H). | | | |
| 17 | [structure] | [1,2,4]Triazine-3-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-difluoromethoxy-ethyl)-amide | white solid | 51 |
| | ¹H NMR (300 MHz, d₆-DMSO): δ(ppm): 9.61 (dd, 1H), 9.32 (dd, 1H), 7.32-7.15 (m, 5H), 6.60 (wt, J = 75 Hz, 1H), 6.58 (wt, J = 76 Hz, 1H), 4.71-4.61 (m, 1H), 4.76-4.59 (m, 2H), 4.19-3.99 (m, 2H), 4.03-3.88 (m, 2H), 3.25-3.16 (m, 1H), 2.97-2.85 (m, 2H), 2.68-2.53 (m, 1H), 1.37 (s, 3H). | | | |
| 18 | [structure] | Pyrimidine-4-carboxylic acid ((S)-1-{(S)-1-[(S)-1-benzyl-2-((R)-2-methyloxiranyl)-2-oxo-ethylcarbamoyl]-2-difluoromethoxy-ethylcarbamoyl}-2-difluoromethoxyethyl)-amide | white solid | 39 |

TABLE 5-continued

| Example # | Structure | Nomenclature | Appearance | Yield (%) |
|---|---|---|---|---|
| | ¹H NMR (300 MHz, d₆-DMSO): δ(ppm): 9.73 (s, 1H), 7.93 (dd, 1H), 7.68 (dd, 1H), 7.32-7.15 (m, 5H), 6.60 (wt, J = 75 Hz, 1H), 6.58 (wt, J = 76 Hz, 1H), 4.75-4.61 (m, 1H), 4.83-4.59 (m, 2H), 4.21-4.03 (m, 2H), 4.01-3.84 (m, 2H), 3.19-3.13 (m, 1H), 3.01-2.89 (m, 2H), 2.67-2.51 (m, 1H), 1.37 (s, 3H). | | | |
| 19 | [structure] | 2-Methyl-thiazole-5-carboxylic acid ((S)-1-{(S)-1-[(S)-1-benzyl-2-((R)-2-methyl-oxiranyl)-2-oxo-ethylcarbamoyl]-3-methylbutylcarbamoyl}-2-difluoromethoxyethyl)-amide | white yellowish solid | 48 |
| | ¹H NMR (300 MHz, d₆-DMSO): δ(ppm): 8.77 (s, 1H), 7.31-7.16 (m, 3H), 7.11 (dd, 2H), 6.71 (wd, 1H), 6.63 (d, 1H), 6.41 (t, 1H), 6.17 (t, J = 75 Hz, 1H), 5.21 (br. s, 1H), 4.81-4.78 (m, 1H), 4.53 (td, 1H), 4.41-4.37 (m, 1H), 4.23-4.05 (m, 2H), 4.01 (dd, 1H), 3.97-3.90 (m, 1H), 3.25 (s, 3H), 3.21 (d, 1H), 3.16-3.13 (m, 1H), 2.79 (d, 1H), 2.81-7.65 (m, 1H), 1.79-1.68 (m, 1H), 1.47 (s, 3H), 0.97-0.89 (m, 6H). | | | |
| 20 | [structure] | 2-Methyl-thiazole-5-carboxylic acid ((S)-2-difluoromethoxy-1-{(S)-3-methyl-1-[(S)-3-methyl-1-((R)-2-methyloxiranecarbonyl)-butylcarbamoyl]-butylcarbamoyl}-ethyl)-amide | white yellowish solid | 67 |
| | ¹H NMR (300 MHz, d₆-DMSO): δ(ppm): 8.65 (s, 1H), 6.98 (wd, 1H), 6.83 (wd, 1H), 6.61-6.53 (m, 1H), 6.17 (t, J = 75 Hz, 1H), 6.07 (br. s, 1H), 4.79-4.68 (m, 1H), 4.61-4.55 (m, 1H), 4.26-4.15 (m, 1H), 4.13-4.03 (m, 2H), 3.98-3.86 (m, 1H), 3.81 (dd, 1H), 3.21 (s, 3H) 3.27 (d, 1H), 3.12 (dd, 1H), 2.81 (d, 1H), 2.78-2.75 (m, 1H), 1.71-1.67 (m, 2H), 1.47 (s, 3H), 0.97-0.89 (m, 12H). | | | |
| 21 | [structure] | 2-Methyl-thiazole-5-carboxylic acid ((S)-1-{(S)-2-difluoromethoxy-1-[(S)-3-methyl-1-((R)-2-methyloxiranecarbonyl)-butylcarbamoyl]-ethylcarbamoyl}-3-methylbutyl)-amide | white yellowish solid | 34 |
| | ¹H NMR (300 MHz, d₆-DMSO): δ(ppm): 8.61 (s, 1H), 6.81-6.78 (m, 2H), 6.68-6.61 (m, 1H), 6.16 (t, J = 75 Hz, 1H), 5.99 (br. s, 1H), 4.79-4.59 (m, 2H), 4.26-4.06 (m, 3H), 3.99-3.89 (m, 1H), 3.76 (dd, 1H), 3.27 (d, 1H), 3.18 (s, 3H), 3.15 (dd, 1H), 2.93 (d, 1H), 2.75-2.71 (m, 1H), 1.681.64 (m, 2H), 1.48 (s, 3H), 0.98-0.90 (m, 12H). | | | |
| 22 | [structure] | 2-Methyl-thiazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-3-methylbutyl)-amide | white yellowish solid | 34 |

| Example # | Structure | Nomenclature | Appearance | Yield (%) |
|---|---|---|---|---|
| | ¹H NMR (300 MHz, d₆-DMSO): δ(ppm): 8.65 (s, 1H), 7.28-7.17 (m, 3H), 7.09 (dd, 2H), 7.01-6.71 (m, 1H), 6.65 (d, 1H), 6.38 (t, 1H), 6.15 (t, J = 75 Hz, 1H), 5.98 (br. s, 1H), 4.75-4.67 (m, 1H), 4.45 (td, 1H), 4.45-4.36 (m, 1H), 4.30-4.05 (m, 2H), 3.98 (dd, 1H), 3.95-3.88 (m, 1H), 3.19 (s, 3H), 3.17 (d, 1H), 3.15-3.08 (m, 1H), 2.81 (d, 1H), 2.77-7.60 (m, 1H), 1.81-1.72 (m, 1H), 1.46 (s, 3H), 0.98-0.87 (m, 6H). | | | |
| 23 | 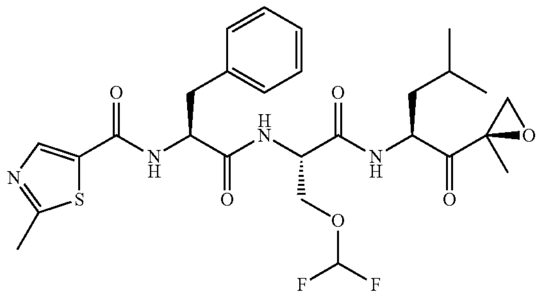 [SMILES: Cc1ncc(C(=O)N[C@@H](Cc2ccccc2)C(=O)N[C@@H](COC(F)F)C(=O)N[C@@H](CC(C)C)C(=O)[C@@]2(C)CO2)s1] | 2-Methyl-thiazole-5-carboxylic acid ((S)-1-{(S)-2-difluoromethoxy-1-[(S)-3-methyl-1-((R)-2-methyl-oxiranecarbonyl)-butylcarbamoyl]-ethylcarbamoyl}-2-phenylethyl)-amide | yellow solid | 28 |
| | ¹H NMR (300 MHz, d₆-DMSO): δ(ppm): 8.69 (s, 1H), 7.32-7.16 (m, 3H), 7.13 (dd, 2H), 7.11-6.91 (m, 1H), 6.72 (d, 1H), 6.48 (t, 1H), 6.17 (t, J = 75 Hz, 1H), 6.08 (br. s, 1H), 4.75-4.67 (m, 1H), 4.45 (td, 1H), 4.45-4.36 (m, 1H), 4.30-4.05 (m, 2H), 3.98 (dd, 1H), 4.01-3.89 (m, 1H), 3.21 (s, 3H), 3.19 (d, 1H), 3.17-3.11 (m, 1H), 2.78 (d, 1H), 2.76-7.62 (m, 1H), 1.85-1.77 (m, 1H), 1.45 (s, 3H), 0.97-0.86 (m, 6H). | | | |
| 24 | 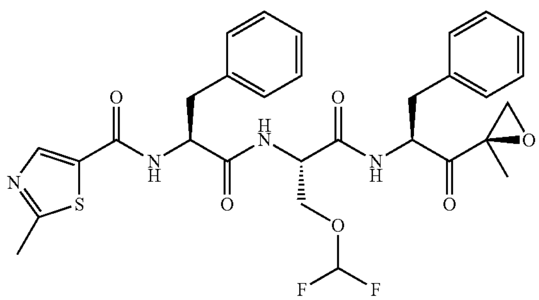 [SMILES: Cc1ncc(C(=O)N[C@@H](Cc2ccccc2)C(=O)N[C@@H](COC(F)F)C(=O)N[C@@H](Cc2ccccc2)C(=O)[C@@]2(C)CO2)s1] | 2-Methyl-thiazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-phenylethyl)-amide | yellow pale solid | 49 |
| | ¹H NMR (400 MHz, CDCl₃): δ(ppm): δ(ppm): 8.45 (s, 1H), 7.35-7.07 (m, 10H), 6.81-6.76 (m, 1H), 6.62-6.57 (m, 1H), 6.19 (t, J = 72 Hz, 1H), 4.78-4.67 m, 1H), 4.63-4.52 (m, 2H), 4.28-4.19 (m, 1H), 4.03-3.93 (m, 1H), 3.55 (br. s, 2H), .53-2.39 (m, 4H), 1.46 (s, 3H). | | | |

TABLE 6

| Compound # | Structure | Nomenclature | Appearance | Yield (%) |
|---|---|---|---|---|
| XVII(b) | 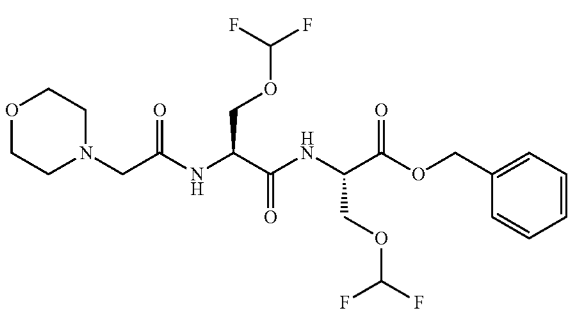 [SMILES: O=C(CN1CCOCC1)N[C@@H](COC(F)F)C(=O)N[C@@H](COC(F)F)C(=O)OCc1ccccc1] | benzyl (2S)-3-(difluoromethoxy)-2-[[(2S)-3-(difluoromethoxy)-2-[(2-morpholinoacetyl)amino]propanoyl]amino]propanoate | white solid | 84 |

¹H NMR (400 MHz, CDCl₃): δ(ppm): 7.89 (m, 1H), 7.41-7.30 (m, 5H), 7.04 (m, 1H), 6.22 (t, J = 74 Hz, 1H), 6.13 (t, J = 74 Hz, 1H), 5.22 (s, 2H), 4.84-4.78 (m, 1H), 4.77-4.72 (m, 1H), 4.32-4.27 (m, 2H), 4.21-4.15 (m, 1H), 4.07-4.00 (m, 1H), 3.76-3.69 (m, 4H), 3.07 (s, 2H), 2.68-2.52 (m, 4H).

TABLE 6-continued

| Compound # | Structure | Nomenclature | Appearance | Yield (%) |
|---|---|---|---|---|
| XVII(c) | 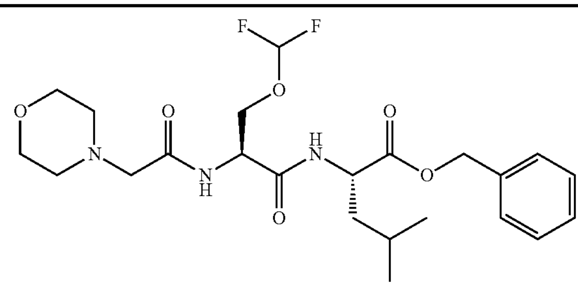 | benzyl(2S)-2-[[(2S)-3-(difluoro-methoxy)-2-[(2-morpholinoacetyl)-amino]-propanoyl]amino]-4-methylpentanoate | off-white powder | 89 |

$^1$H NMR (400 MHz, CDCl$_3$): δ(ppm): 7.85 (m, 1H), 7.40-7.30 (m, 5H), 6.66 (m, 1H), 6.20 (t, J = 74 Hz, 1H), 5.20-5.12 (m, 2H), 4.72-4.58 (m, 2H), 4.26-4.22 (m, 1H), 4.03-3.97 (m, 1H), 3.75-3.67 (m, 4H), 3.06 (s, 2H), 2.55-2.50 (m, 4H), 1.72-1.62 (m, 1H), 0.96-0.85 (m, 6H).

| | | | | |
|---|---|---|---|---|
| XVII(d) | | benzyl (2S)-3(difluoromethoxy)-2-[[(2S)-2-[(2-morpholinoacetyl)amino]-3-phenyl-propanoyl]amino]-propanoate | off-white powder | 76 |

$^1$H NMR (400 MHz, CDCl$_3$): δ(ppm): 7.81 (m, 1H), 7.41-6.95 (m, 10 H), 6.17 (t, J = 74 Hz, 1H), 5.21-5.13 (m, 2H), 4.90-4.83 (m, 1H), 4.72-4.64 (m, 1H), 4.31-4.25 (m, 1H), 401-3.93 (m, 1H), 3.73-3.61 (m, 4H), 3.91-2.49 (m, 4H), 2.51-2.43 (m, 4H).

| | | | | |
|---|---|---|---|---|
| XVII(e) | | benzyl (2S)-3-(difluoromethoxy)-2-[[(2S)-4-methyl-2-[(2-morpholinoacetyl)amino]pentanoyl]amino]propanoate | off-white powder | 87 |

TABLE 7

| Compound # | Structure | Nomenclature | Appearance | Yield (%) |
|---|---|---|---|---|
| XVIII(b) | 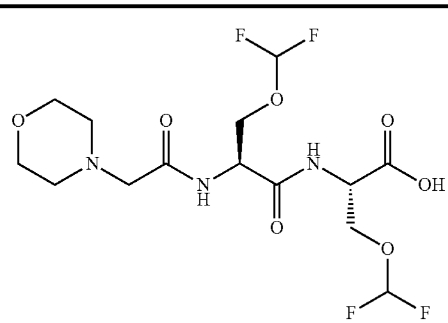 | (2S)-3-(difluoromethoxy)-2-[[(2S)-3-(difluoromethoxy)-2-[(2-morpholino-acetyl)amino]propanoyl]amino]-propanoic acid | white solid | 95 |

TABLE 7-continued

| Compound # | Structure | Nomenclature | Appearance | Yield (%) |
|---|---|---|---|---|
| | ¹H NMR (300 MHz, CDCl₃): δ(ppm): 7.89 (m, 1H), 7.41-7.30 (m, 5H), 7.04 (m, 1H), 6.22 (t, J = 74 Hz, 1H), 6.13 (t, J = 74 Hz, 1H), 5.22 (s, 2H), 4.84-4.78 (m, 1H), 4.77-4.72 (m, 1H), 4.32-4.27 (m, 2H), 4.21-4.15 (m, 1H), 4.07-4.00 (m, 1H), 3.76-3.69 (m, 4H), 3.07 (s, 2H), 2.68-2.52 (m, 4H). | | | |
| XVIII(c) | 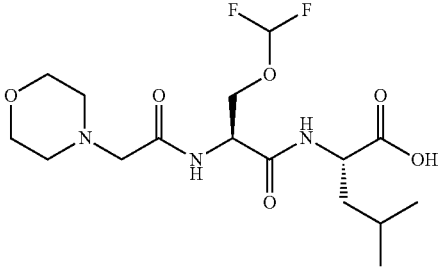 [SMILES: CC(C)C[C@H](NC(=O)[C@H](COC(F)F)NC(=O)CN1CCOCC1)C(=O)O] | (2S)-2-[[(2S)-3-(difluoromethoxy)-2-[(2-morpholinoacetyl)amino]-propanoyl]amino]-4-methylpentanoic acid | off-white sticky solid | 99 |
| | ¹H NMR (300 MHz, CDCl₃): δ(ppm): 7.85 (m, 1H), 7.40-7.30 (m, 5H), 6.66 (m, 1H), 6.20 (t, J = 74 Hz, 1H), 5.20-5.12 (m, 2H), 4.72-4.58 (m, 2H), 4.26-4.22 (m, 1H), 4.03-3.97 (m, 1H), 3.75-3.67 (m, 4H), 3.06 (s, 2H), 2.55-2.50 (m, 4H), 1.72-1.62 (m, 1H), 0.96-0.85 (m, 6H). | | | |

TABLE 8

| Example # | Structure | Nomenclature | Appearance | Yield (%) |
|---|---|---|---|---|
| 26 | 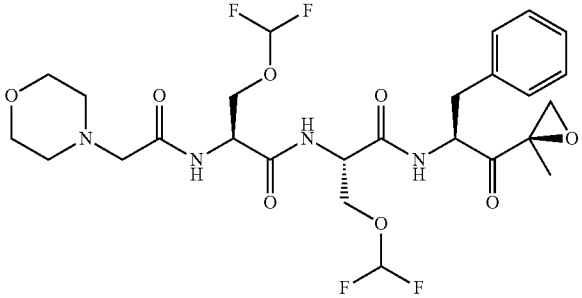 [SMILES: C[C@]1(C(=O)[C@H](Cc2ccccc2)NC(=O)[C@H](COC(F)F)NC(=O)[C@H](COC(F)F)NC(=O)CN2CCOCC2)CO1] | (S)-N-{(S)-1-[(S)-1-Benzyl-2-((R)-2-methyl-oxiranyl)-2-oxo-ethylcarbamoyl]-2-difluoromethoxyethyl}-3-difluoromethoxy-2-(2-morpholin-4-yl-acetylamino)-propionamide | white solid | 53 |
| | ¹H NMR (400 MHz, CDCl₃): δ(ppm): 7.94 (m, 1H), 7.32-7.12 (m, 5H), 6.87 (m, 1H), 6.70 (m, 1H), 6.22 (t, J = 74 Hz, 1H), 6.12 (t, J = 74 Hz, 1H), 4.88-4.78 (m, 1H), 4.66-4.55 (m, 1H), 4.32-4.26 (m, 1H), 4.23-4.14 (m, 1H), 4.08-4.02 (m, 1H), 3.92-3.88 (m, 1H), 3.77-3.68 (m, 4H), 3.28-2.80 (m, 5H), 2.60-2.51 (m, 4H), 1.51 (s, 3H). | | | |
| 27 | 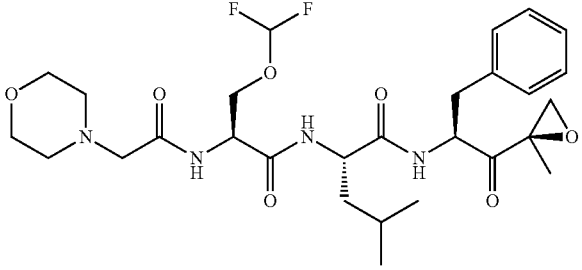 [SMILES: CC(C)C[C@H](NC(=O)[C@H](COC(F)F)NC(=O)CN1CCOCC1)C(=O)N[C@@H](Cc1ccccc1)C(=O)[C@@]1(C)CO1] | (2S)-N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-4-methylpentanamide | off-white solid | 47 |
| | ¹H NMR (400 MHz, CDCl₃): δ(ppm): 7.85 (m, 1H), 7.38-7.12 (m, 5H), 6.82-6.78 (m, 1H), 6.24 (t, J = 74 Hz, 1H), 6.13-6.11 (m, 1H), 4.71-4.58 (m, 3H), 4.42-4.35 (m, 1H), 4.15-4.05 (m, 1H), 3.83-3.75 (m, 4H), 3.33-2.95 (m, 5H), 2.60-2.55 (m, 4H), 2.22 (s, 3H), 1.61-1.42 (m, 3H), 0.98-0.87 (m, 6H). | | | |

TABLE 8-continued

| Example # | Structure | Nomenclature | Appearance | Yield (%) |
|---|---|---|---|---|
| 28 | 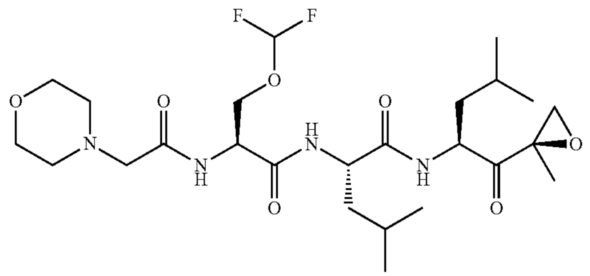 [SMILES: CC(C)C[C@H](NC(=O)[C@H](COC(F)F)NC(=O)CN1CCOCC1)C(=O)N[C@@H](CC(C)C)C(=O)[C@@]1(C)CO1] | (2S)-2-[[(2S)-3-(difluoromethoxy)-2-[(2-morpholino-acetyl)amino] propanoyl]amino]-4-methyl-N-[(1S)-3-methyl-1-[(2R)-2-methyloxirane-2-carbonyl] butyl]pentanamide | pale solid | 71 |

¹H NMR (400 MHz, CDCl₃): δ(ppm): 7.84 (m, 1H), 6.59 (m, 1H), 6.26 (t, J = 74 Hz, 1H), 6.22 (m, 1H), 4.70-4.64 (m, 1H), 4.61-4.55 (m, 1H), 4.43-4.36 (m, 1H), 4.29-4.02 (m, 1H), 3.75-3.71 (m, 4H), 3.28-3.25 (m, 1H), 3.07 (s, 2H), 2.91-2.87 (m, 1H), 2.57-2.53 (m, 4H), 1.68-1.50 (m, 4H), 1.51 (s, 3H), 1.31-1.22 (m, 2H), 0.97-0.89 (m, 12H).

| 29 | | (2S)-N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino] propanoyl]amino]-3-(1-methylcyclohexa-1,3,5-trien-1-yl)propanamide | white powder | 63 |

¹H NMR (400 MHz, CDCl₃): δ(ppm): δ 7.74 (m, 1H), 7.32-6.98 (m, 10H), 6.70 (m, 1H), 6.59 (m, 1H), 6.18 (t, J = 72 Hz, 1H), 4.81-4.68 m, 1H), 4.61-4.51 (m, 2H), 4.23 = 4.17 (m, 1H), 3.99-3.95 (m, 1H), 3.68 (br. s, 2H), 3.10-2.90 (m, 6H), 2.80-2.59 (m, 2H), 2.53-2.39 (m, 4H), 1.48 (s, 3H).

| 30 | | (S)-4-Methyl-2-(2-morpholin-4-yl-acetylamino)-pentanoic acid {(S)-2-difluoromethoxy-1-[(S)-3-methyl-1-((R)-2-methyl-oxiranecarbonyl)-butylcarbamoyl]-ethyl}-amide | off-white solid | 34 |

¹H NMR (400 MHz, CDCl₃): δ(ppm): 7.88-7.76 (m, 1H), 6.63-6.59 (m, 1H), 6.29 (t, J = 75 Hz, 1H), 6.34 (m, 1H), 4.81-4.75 (m, 1H), 4.70-4.63 (m, 1H), 4.47-4.4 (m, 1H), 4.32-4.05 (m, 1H), 3.81-3.74 (m, 4H), 3.36-3.26 (m, 1H), 3.11 (s, 2H), 3.01-2.95 (m, 1H), 2.66-2.61 (m, 4H), 1.73-1.65 (m, 4H), 1.52 (s, 3H), 1.42-1.36 (m, 2H), 0.99-0.91 (m, 12H).

| 31 | | (S)-4-Methyl-2-(2-morpholin-4-yl-acetylamino)-pentanoic acid {(S)-1-[(S)-1-benzyl-2-((R)-2-methyl-oxiranyl)-2-oxo-ethylcarbamoyl]-2-difluoro-methoxyethyl}-amide | off-white solid | 72 |

¹H NMR (400 MHz, CDCl₃): δ(ppm): 8.01 (m, 1H), 7.02 (m, 1H), 6.79 (m, 1H), 6.41 (t, J = 74 Hz, 1H), 6.35 (t, J = 74 Hz, 1H), 4.74-4.68 (m, 3H), 4.88-4.24 (m, 2H), 4.14-4.08 (m, 1H), 3.97-3.89 (m, 1H), 3.76-3.68 (m, 4H), 3.22 (d, J = 4 Hz, 1H), 2.90 (d, J = 4 Hz, 1H), 2.58-2.53 (m, 4H), 1.63-1.50 (m, 2H), 1.51 (s, 3H), 1.36-1.26 (m, 1H), 0.96-0.91 (m, 6H).

TABLE 8-continued

| Example # | Structure | Nomenclature | Appearance | Yield (%) |
|---|---|---|---|---|
| 32 | 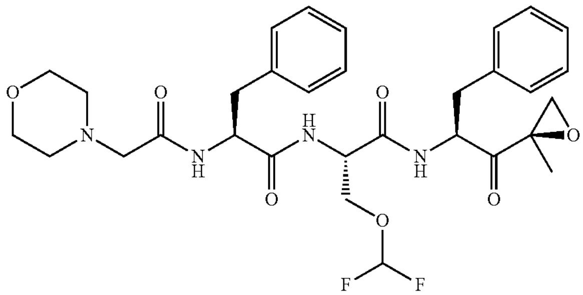 [SMILES: C[C@]1(C(=O)[C@H](Cc2ccccc2)NC(=O)[C@H](COC(F)F)NC(=O)[C@H](Cc2ccccc2)NC(=O)CN2CCOCC2)CO1] | (2S)-N-[(1S)-2-[[(1S)-1-benzyl-2-[(2R)-2-methyloxiran-2-yl]-2-oxo-ethyl]amino]-1(difluoromethoxymethyl)-2-oxo-ethyl]-2-[(2-morpholino acetyl) amino]-3-phenyl-propanamide | off-white powder | 61 |

$^1$H NMR (400 MHz, CDCl$_3$): δ(ppm): 7.82 (m, 1H), 7.42-7.01 (m, 10H), 6.77-6.68 (m, 1H), 6.65-6.58 (m, 1H), 6.18 (t, J = 74 Hz, 1H), 4.86-4.72 (m, 1H), 4.72-4.60 (m, 2H), 4.23-4.21-4.16 (m, 1H), 402-3.98 (m, 1H), 3.71 (br. s, 2H), 3.14-2.95 (m, 6H), 2.82-2.69 (m, 2H), 2.62-2.47 (m, 4H), 1.49 (s, 3H).

| 33 | | (2S)-3-(difluoromethoxy)-N-[(1S)-1-(difluoromethoxymethyl)-2-[[(1S)-3-methyl-1-[(2R)-2-methyloxirane-2-carbonyl]butyl]amino]-2-oxo-ethyl]-2-[(2-morpholinoacetyl) amino]propanamide | off-white powder | 71 |

NMR (CDCl$_3$, 400 MHz): δ(ppm); 7.93 (m, 1H), 6.95 (m, 1H), 6.58 (m, 1H), 6.29 (t, J = 74 Hz, 1H), 6.22 (t, J = 74 Hz, 1H), 4.74-4.68 (m, 3H), 4.88-4.24 (m, 2H), 4.14-4.08 (m, 1H), 3.97-3.89 (m, 1H), 3.76-3.68 (m, 4H), 3.22 (d, J = 4 Hz, 1H), 2.90 (d, J = 4 Hz, 1H), 2.58-2.53 (m, 4H), 1.63-1.50 (m, 2H), 1.51 (s, 3H), 1.36-1.26 (m, 1H), 0.96-0.91 (m, 6H).

TABLE 9

| | Cell line | | | |
|---|---|---|---|---|
| | OCI-AML-2 | | KMS-11 | |
| | IC$_{50}$ (nM)* | | | |
| Example # | Cell Viability | CT-L proteasome activity | Cell Viability | CT-L proteasome activity |
| 1 | 108.7 ± 25.31 | 39.17 ± 2.121 | 30.90 ± 10.71 | 29.62 ± 3.69 |
| 25 | 55.60 ± 19.20 | 153.9 ± 14.81 | 39.55 ± 7.45 | 172.9 ± 14.15 |
| 27 | 400.6 ± 275.4 | 599.9 ± 57.47 | 249.6 ± 25.89 | 742.5 ± 83.71 |
| 28 | 131.6 ± 87.55 | 556.1 ± 122.9 | 100.3 ± 18.69 | 575.1 ± 62.72 |
| 26 | 223.2 ± 10.34 | 358.5 ± 176.8 | 99.67 ± 17.73 | 174.1 ± 434.5 |
| 33 | 140.2 ± 53.47 | 598.8 ± 77.65 | 46.71 ± 9.89 | 703.8 ± 173 |
| 29 | 75.86 ± 14.97 | 131.7 ± 10.38 | 60.4 ± 11.18 | 135.3 ± 12.3 |

*Unless otherwise indicated, all experiments have been performed independently at least twice, and results are presented as the mean ± standard deviation.

TABLE 10*

| | chymotrypsin-like (CT-L) | | | Trypsin-like (T-L) | | | Caspase-like (C-L) | | |
|---|---|---|---|---|---|---|---|---|---|
| Example # (Dose) | 0 | 30 min | 24 hours | 0 | 30 min | 24 hrs | 0 | 30 min | 24 hrs |
| Vehicle | 100% | 98% | 101% | 100% | 100% | 100% | 100% | 100% | 100% |
| 1 (50 mg) | 100% | 27% | 22% | 100% | 100% | 100% | 100% | 100% | 100% |
| 26 (60 mg) | 100% | 33% | 27% | 100% | 100% | 100% | 100% | 100% | 100% |

*Data are presented as mean residual activity (SEM) relative to vehicle treated controls.

TABLE 11

| Panel | Cell Line | | |
|---|---|---|---|
| | $Log_{10}GI_{50}$ | $Log_{10}TGI_{50}$ | $Log_{10}LC_{50}$ |
| Leukemia | | | |
| CCRF-CEM | −7.26 | >−4.00 | >−4.00 |
| HL-60(TB) | −6.56 | >−4.00 | >−4.00 |
| K-562 | −6.50 | >−4.00 | >−4.00 |
| MOLT-4 | −7.37 | >−4.00 | >−4.00 |
| RPMI-8226 | −7.40 | −4.86 | >−4.00 |
| SR | −7.30 | >−4.00 | >−4.00 |
| Non-Small Cell Lung Cancer | | | |
| A549/ATCC | −6.41 | >−4.00 | >−4.00 |
| EKVX | −6.22 | >−4.00 | >−4.00 |
| HOP-62 | −6.41 | >−4.00 | >−4.00 |
| HOP-92 | −6.23 | −5.40 | −4.39 |
| NCI-H226 | −7.44 | −6.84 | — |
| NCI-H23 | −6.85 | −5.92 | −5.27 |
| NCI-H322M | −5.54 | −4.74 | −4.23 |
| NCI-H460 | −6.48 | −5.84 | −5.12 |
| NCI-H522 | −6.86 | −6.15 | −4.15 |
| Colon Cancer | | | |
| COLO 205 | −6.22 | −4.85 | >−4.00 |
| HCC-2998 | −6.74 | −6.45 | −6.15 |
| HCT-116 | −7.32 | −6.71 | −6.17 |
| HCT-15 | −5.65 | −4.93 | −4.16 |
| HT29 | −7.29 | −6.22 | −4.32 |
| KM12 | −6.88 | −6.49 | −6.10 |
| SW-620 | −7.39 | −5.95 | −4.40 |
| CNS Cancer | | | |
| SF-268 | −6.98 | −5.90 | >−4.00 |
| SF-295 | −7.17 | −6.24 | −4.88 |
| SF-539 | −7.15 | −6.44 | −4.27 |
| SNB-19 | −6.49 | >−4.00 | >−4.00 |
| SNB-75 | −6.81 | −6.24 | >−4.00 |
| U251 | −6.55 | −4.94 | >−4.00 |
| Melanoma | | | |
| LOX IMVI | −6.96 | −6.56 | −6.16 |
| MALME-3M | −7.30 | −6.38 | >−4.00 |
| M14 | −6.86 | −6.24 | −4.35 |
| MDA-MB-435 | −7.43 | −6.74 | >−4.00 |
| SK-MEL-28 | −6.85 | −6.12 | −4.69 |
| SK-MEL-5 | −7.15 | −6.34 | −5.47 |
| UACC-257 | −6.87 | −6.20 | >−4.00 |
| UACC-62 | −6.68 | −5.78 | −4.95 |
| Ovarian Cancer | | | |
| OVCAR-3 | −7.46 | −6.90 | −6.30 |
| OVCAR-4 | −6.29 | >−4.00 | >−4.00 |
| OVCAR-5 | −6.18 | −5.30 | −4.17 |
| OVCAR-8 | −5.80 | >−4.00 | >−4.00 |
| NCI/ADR-RES | −5.11 | −4.23 | >−4.00 |
| SK-OV-3 | −6.06 | >−4.00 | >−4.00 |
| Renal Cancer | | | |
| 786-0 | −6.43 | −4.62 | >−4.00 |
| A498 | −8.00 | −6.38 | −4.88 |
| ACHN | −6.53 | −4.81 | >−4.00 |
| CAKI-1 | −6.40 | −5.28 | >−4.00 |
| RXF 393 | −6.79 | −6.41 | −6.02 |
| SN12C | −6.54 | −5.29 | −4.03 |
| TK-10 | −6.71 | −6.06 | — |
| UO-31 | −5.84 | −5.32 | −4.59 |
| Prostate Cancer | | | |
| PC-3 | −6.48 | −4.99 | >−4.00 |
| DU-145 | −6.58 | −5.64 | −5.02 |
| Breast Cancer | | | |
| MCF7 | −7.35 | −4.62 | >−4.00 |
| MDA-MB-231/ATCC | −6.66 | −6.01 | −4.73 |
| HS 578T | −7.33 | −5.44 | >−4.00 |
| BT-549 | −7.49 | −6.87 | −5.74 |
| T-47D | −6.59 | >−4.00 | — |
| MDA-MB-468 | −6.75 | −6.32 | — |

TABLE 12

| Panel | Cell Line | | |
|---|---|---|---|
| | $Log_{10}GI_{50}$ | $Log_{10}TGI_{50}$ | $Log_{10}LC_{50}$ |
| Leukemia | | | |
| HL-60(TB) | −7.45 | −6.35 | >−4.00 |
| K-562 | −7.41 | >−4.00 | >−4.00 |
| MOLT-4 | −7.69 | −7.11 | >−4.00 |
| RPMI-8226 | −7.52 | −7.04 | >−4.00 |
| SR | −7.71 | >−4.00 | >−4.00 |
| Non-Small Cell Lung Cancer | | | |
| A549/ATCC | −7.41 | −6.13 | >−4.00 |
| HOP-62 | −7.75 | −7.42 | −7.09 |
| HOP-92 | −7.65 | −7.16 | −6.35 |
| NCI-H226 | −7.77 | −7.43 | −7.10 |
| NCI-H23 | −7.62 | −7.13 | −5.64 |
| NCI-H322M | −7.10 | −6.33 | >−4.00 |
| NCI-H460 | −7.21 | −6.43 | −4.13 |
| NCI-H522 | −7.67 | −7.19 | >−4.00 |
| Colon Cancer | | | |
| COLO 205 | −7.39 | −6.76 | −6.21 |
| HCC-2998 | −7.74 | −7.47 | −7.20 |
| HCT-116 | −7.70 | −7.30 | −6.55 |
| HCT-15 | −6.47 | >−4.00 | >−4.00 |
| HT29 | −7.45 | −5.84 | >−4.00 |
| KM12 | −7.72 | −7.39 | −7.06 |
| SW-620 | −7.41 | −5.93 | >−4.00 |
| CNS Cancer | | | |
| SF-268 | −7.60 | −7.14 | >−4.00 |
| SF-295 | −7.68 | −7.26 | −6.49 |
| SF-539 | −7.63 | −7.26 | −6.48 |
| SNB-19 | −7.23 | >−4.00 | >−4.00 |
| SNB-75 | −7.71 | −7.24 | −6.35 |
| U251 | −7.44 | −6.75 | >−4.00 |
| Melanoma | | | |
| LOX IMVI | −7.73 | −7.42 | −7.10 |
| MALME-3M | −7.51 | −6.64 | >−4.00 |
| M14 | −7.48 | −6.71 | >−4.00 |
| MDA-MB-435 | −7.75 | −7.42 | −7.10 |
| SK-MEL-2 | −7.54 | −7.03 | −5.46 |
| SK-MEL-28 | −7.38 | −6.69 | −4.82 |
| SK-MEL-5 | −7.60 | −7.17 | −6.49 |
| UACC-257 | −7.18 | −6.32 | >−4.00 |
| UACC-62 | −7.35 | −6.63 | −4.58 |
| Ovarian Cancer | | | |
| IGROV1 | −7.43 | −6.38 | >−4.00 |
| OVCAR-3 | −7.66 | −7.33 | −6.97 |
| OVCAR-4 | −7.50 | −6.75 | >−4.00 |
| OVCAR-5 | −7.36 | −6.44 | >−4.00 |
| OVCAR-8 | −7.32 | −6.41 | >−4.00 |
| NCI/ADR-RES | −5.82 | >−4.00 | >−4.00 |
| SK-OV-3 | −7.30 | −6.60 | — |
| Renal Cancer | | | |
| 786-0 | −7.20 | −6.49 | −5.44 |
| A498 | −7.61 | −7.03 | −6.34 |
| ACHN | −7.01 | >−4.00 | >−4.00 |
| CAKI-1 | −6.72 | −6.09 | >−4.00 |
| RXF 393 | −7.64 | −7.25 | −6.70 |
| SN12C | −7.39 | −6.67 | −5.15 |
| TK-10 | −7.49 | −6.07 | >−4.00 |
| UO-31 | −6.62 | −5.95 | −5.17 |

TABLE 12-continued

| Panel | Cell Line | | |
|---|---|---|---|
| | $Log_{10}GI_{50}$ | $Log_{10}TGI_{50}$ | $Log_{10}LC_{50}$ |
| Prostate Cancer | | | |
| PC-3 | −7.45 | −6.80 | −5.14 |
| DU-145 | −7.27 | −5.32 | >−4.00 |
| Breast Cancer | | | |
| MCF7 | −7.53 | −4.89 | >−4.00 |
| MDA-MB-231/ATCC | −7.52 | −6.80 | −4.21 |
| HS 578T | −7.54 | −6.24 | >−4.00 |
| BT-549 | −7.73 | −7.39 | −7.05 |
| T-47D | −7.78 | −7.46 | — |
| MDA-MB-468 | −7.54 | −6.96 | >−4.00 |

TABLE 13

| Panel | Cell Line | | |
|---|---|---|---|
| | $Log_{10}GI_{50}$ | $Log_{10}TGI_{50}$ | $Log_{10}LC_{50}$ |
| Leukemia | | | |
| HL-60(TB) | −7.45 | −6.35 | >−4.00 |
| K-562 | −7.41 | >−4.00 | >−4.00 |
| MOLT-4 | −7.69 | −7.11 | >−4.00 |
| RPMI-8226 | −7.52 | −7.04 | >−4.00 |
| SR | −7.71 | >−4.00 | >−4.00 |
| Non-Small Cell Lung Cancer | | | |
| A549/ATCC | −7.41 | −6.13 | >−4.00 |
| HOP-62 | −7.75 | −7.42 | −7.09 |
| HOP-92 | −7.65 | −7.16 | −6.35 |
| NCI-H226 | −7.77 | −7.43 | −7.10 |
| NCI-H23 | −7.62 | −7.13 | −5.64 |
| NCI-H322M | −7.10 | −6.33 | >−4.00 |
| NCI-H460 | −7.21 | −6.43 | −4.13 |
| NCI-H522 | −7.67 | −7.19 | >−4.00 |
| Colon Cancer | | | |
| COLO 205 | −7.39 | −6.76 | −6.21 |
| HCC-2998 | −7.74 | −7.47 | −7.20 |
| HCT-116 | −7.70 | −7.30 | −6.55 |
| HCT-15 | −6.47 | >−4.00 | >−4.00 |
| HT29 | −7.45 | −5.84 | >−4.00 |
| KM12 | −7.72 | −7.39 | −7.06 |
| SW-620 | −7.41 | −5.93 | >−4.00 |
| CNS Cancer | | | |
| SF-268 | −7.60 | −7.14 | >−4.00 |
| SF-295 | −7.68 | −7.26 | −6.49 |
| SF-539 | −7.63 | −7.26 | −6.48 |
| SNB-19 | −7.23 | >−4.00 | >−4.00 |
| SNB-75 | −7.71 | −7.24 | −6.35 |
| U251 | −7.44 | −6.75 | >−4.00 |
| Melanoma | | | |
| LOX IMVI | −7.73 | −7.42 | −7.10 |
| MALME-3M | −7.51 | −6.64 | >−4.00 |
| M14 | −7.48 | −6.71 | >−4.00 |
| MDA-MB-435 | −7.75 | −7.42 | −7.10 |
| SK-MEL-2 | −7.54 | −7.03 | −5.46 |
| SK-MEL-28 | −7.38 | −6.69 | −4.82 |
| SK-MEL-5 | −7.60 | −7.17 | −6.49 |
| UACC-257 | −7.18 | −6.32 | >−4.00 |
| UACC-62 | −7.35 | −6.63 | −4.58 |
| Ovarian Cancer | | | |
| IGROV1 | −7.43 | 316.38 | >−4.00 |
| OVCAR-3 | −7.66 | −7.33 | −6.97 |
| OVCAR-4 | −7.50 | −6.75 | >−4.00 |
| OVCAR-5 | −7.36 | −6.44 | >−4.00 |
| OVCAR-8 | −7.32 | −6.41 | >−4.00 |
| NCI/ADR-RES | −5.82 | >−4.00 | >−4.00 |
| SK-OV-3 | −7.30 | −6.60 | |

TABLE 13-continued

| Panel | Cell Line | | |
|---|---|---|---|
| | $Log_{10}GI_{50}$ | $Log_{10}TGI_{50}$ | $Log_{10}LC_{50}$ |
| Renal Cancer | | | |
| 786-0 | −7.20 | −6.49 | −5.44 |
| A498 | −7.61 | −7.03 | −6.34 |
| ACHN | −7.01 | >−4.00 | >−4.00 |
| CAKI-1 | −6.72 | −6.09 | >−4.00 |
| RXF 393 | −7.64 | −7.25 | −6.70 |
| SN12C | −7.39 | −6.67 | −5.15 |
| TK-10 | −7.49 | −6.07 | >−4.00 |
| UO-31 | −6.62 | −5.95 | −5.17 |
| Prostate Cancer | | | |
| PC-3 | −7.45 | −6.80 | −5.14 |
| DU-145 | −7.27 | −5.32 | >−4.00 |
| Breast Cancer | | | |
| MCF7 | −7.53 | −4.89 | >−4.00 |
| MDA-MB-231/ATCC | −7.52 | −6.80 | −4.21 |
| HS 578T | −7.54 | −6.24 | >−4.00 |
| BT-549 | −7.73 | −7.39 | −7.05 |
| T-47D | −7.78 | −7.46 | — |
| MDA-MB-468 | −7.54 | −6.96 | >−4.00 |

TABLE 14

| Panel | Cell Line | | |
|---|---|---|---|
| | $Log_{10}GI_{50}$ | $Log_{10}TGI_{50}$ | $Log_{10}LC_{50}$ |
| Leukemia | | | |
| CCRF-CEM | −7.62 | >−4.00 | >−4.00 |
| K-562 | −7.00 | >−4.00 | >−4.00 |
| MOLT-4 | −7.54 | −7.05 | >−4.00 |
| RPMI-8226 | −7.40 | −6.43 | >−4.00 |
| SR | −7.69 | −4.36 | >−4.00 |
| Non-Small Cell Lung Cancer | | | |
| A549/ATCC | −6.68 | >−4.00 | >−4.00 |
| HOP-62 | −7.31 | −6.53 | −4.32 |
| HOP-92 | −7.18 | −6.55 | −6.03 |
| NCI-H226 | −7.64 | −7.24 | −6.51 |
| NCI-H23 | −7.21 | −5.55 | >−4.00 |
| NCI-H322M | −6.27 | −5.52 | −4.18 |
| NCI-H460 | −6.49 | −5.87 | >−4.00 |
| NCI-H522 | −6.90 | −6.17 | >−4.00 |
| Colon Cancer | | | |
| COLO 205 | −6.90 | −6.32 | −5.34 |
| HCC-2998 | −6.80 | −6.50 | −6.21 |
| HCT-116 | −7.46 | −5.91 | >−4.00 |
| HCT-15 | −6.20 | >−4.00 | >−4.00 |
| HT29 | −7.31 | −4.77 | >−4.00 |
| KM12 | −7.35 | −6.77 | −6.27 |
| SW-620 | −7.40 | −4.92 | >−4.00 |
| CNS Cancer | | | |
| SF-268 | −7.27 | −6.50 | >−4.00 |
| SF-295 | −7.19 | −6.55 | −5.94 |
| SF-539 | −7.39 | −6.76 | −4.49 |
| SNB-19 | −6.51 | >−4.00 | >−4.00 |
| SNB-75 | −6.83 | −6.41 | −5.96 |
| U251 | −6.98 | −5.70 | >−4.00 |
| Melanoma | | | |
| LOX IMVI | −7.50 | −6.90 | −6.35 |
| MALME-3M | −6.69 | −6.15 | >−4.00 |
| M14 | −7.21 | −5.85 | >−4.00 |
| MDA-MB-435 | −7.63 | −7.17 | — |
| SK-MEL-2 | −7.19 | −6.02 | >−4.00 |
| SK-MEL-28 | −7.13 | −6.34 | >−4.00 |
| SK-MEL-5 | −7.22 | −6.66 | −6.20 |

TABLE 14-continued

| Panel | Cell Line | | |
|---|---|---|---|
| | $Log_{10}GI_{50}$ | $Log_{10}TGI_{50}$ | $Log_{10}LC_{50}$ |
| UACC-257 | −6.81 | −6.00 | >−4.00 |
| UACC-62 | −7.00 | −6.37 | >−4.00 |
| Ovarian Cancer | | | |
| IGROV1 | −6.67 | >−4.00 | >−4.00 |
| OVCAR-3 | −7.35 | −6.71 | −5.66 |
| OVCAR-4 | −6.98 | >−4.00 | — |
| OVCAR-5 | −6.65 | −5.58 | >−4.00 |
| OVCAR-8 | −6.59 | >−4.00 | >−4.00 |
| NCI/ADR-RES | −5.58 | >−4.00 | >−4.00 |
| SK-OV-3 | −6.46 | −5.78 | >−4.00 |
| Renal Cancer | | | |
| 786-0 | −6.55 | −5.96 | −4.87 |
| A498 | −6.68 | −6.11 | −5.47 |
| ACHN | −6.59 | >−4.00 | >−4.00 |
| CAKI-1 | −6.56 | −5.94 | >−4.00 |
| RXF 393 | −7.20 | −6.70 | −6.31 |
| SN12C | −6.92 | −6.38 | −4.39 |
| TK-10 | −6.55 | −5.10 | >−4.00 |
| UO-31 | −6.46 | −5.71 | −4.62 |
| Prostate Cancer | | | |
| PC-3 | −7.04 | −6.40 | >−4.00 |
| DU-145 | −7.00 | −5.05 | −4.09 |
| Breast Cancer | | | |
| MCF7 | −7.38 | >−4.00 | >−4.00 |
| MDA-MB-231/ATCC | −7.04 | −6.27 | −4.44 |
| HS 578T | −7.07 | >−4.00 | >−4.00 |
| BT-549 | −7.26 | −6.59 | −4.94 |
| T-47D | −7.16 | −6.62 | — |
| MDA-MB-468 | −6.67 | −6.10 | >−4.00 |

The invention claimed is:

1. A compound of Formula I, or a pharmaceutically acceptable salt, solvate or prodrug thereof:

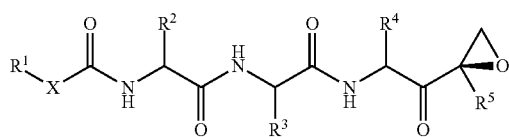

I wherein:

$R^1$ is selected from morpholinyl, 1,4-oxazepanyl, thiomorpholinyl, 1,4-thiazepanyl, 1,4-thiazepanyl-1-oxide, 1,4-thiazepanyl-1,1-dioxide, 1,4-thiazinanyl-1-oxide, 1,4-thiazinanyl-1,1-dioxide, aziridinyl, azetidinyl, pyrrolidinyl, piperazinyl, 1,4-diazepanyl, thiazolyl, isothiazolyl, oxazolyl, isooxazolyl, thiophenyl, furanyl, 1,2,4-triazolyl, pyridyl, pyrazinyl, pyrimidinyl and 1,2,4-triazinyl, wherein $R^1$ is optionally substituted with $C_{1-4}$alkyl;

X is absent or $C_{1-4}$alkylene;

$R^2$, $R^3$ and $R^4$ are each independently selected from $C_{1-6}$alkyl, $C_{1-4}$alkylene-phenyl, $C_{1-4}$alkylene-O—$CH_3$, $C_{1-4}$alkylene-O—$CH_2F$, $C_{1-4}$alkylene-O—$CHF_2$ and $C_{1-4}$alkylene-O—$CF_3$, wherein at least one of $R^2$, $R^3$ and $R^4$ is $C_{1-4}$alkylene-O—$CH_2F$, $C_{1-4}$alkylene-O—$CHF_2$ or $C_{1-4}$alkylene-O—$CF_3$; and $R^5$ is $C_{1-6}$alkyl.

2. The compound of claim 1, wherein $R^1$ is selected from:

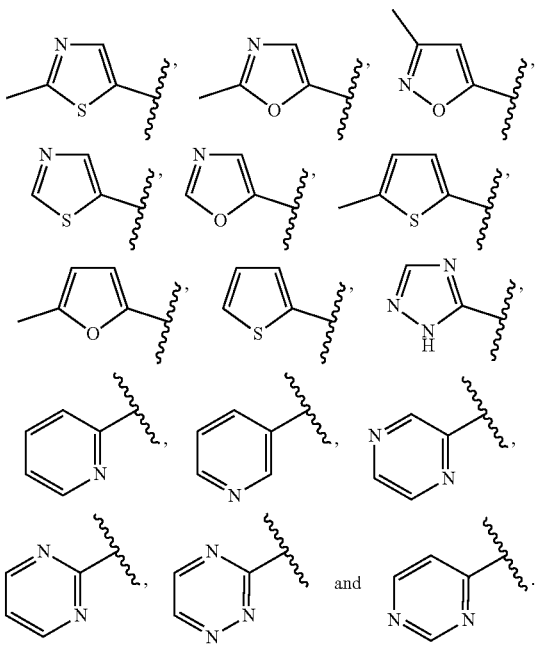

3. The compound of claim 1, wherein X is —$CH_2$—.

4. The compound of claim 1, wherein $R^2$, $R^3$ and $R^4$ are each independently selected from the group consisting of isobutyl, —$CH_2$-Phenyl, —$CH_2$—O—$CH_3$ and —$CH_2$—O—$CHF_2$, wherein at least one of $R^2$ and $R^3$ is —$CH_2$—O—$CHF_2$.

5. The compound of claim 1, wherein $R^5$ is $CH_3$.

6. The compound of claim 1, having the following relative stereochemistry:

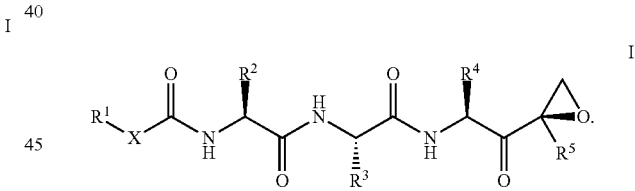

I

7. The compound of claim 1, or a salt, thereof, selected from:

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

2-Methyl-thiazole-5-carboxylic acid-((S)-1-{(S)-1-[(S)-1-benzyl-2-((R)-2-methyloxiranyl)-2-oxo-ethylcarbamoyl]-2-methoxy-ethylcarbamoyl}-2-difluoromethoxyethyl)-amide;

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-methoxy-ethyl)-amide;

2-Methyl-oxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

3-Methyl-isoxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Thiazole-5-carboxylic acid ((S)-1-{(S)-1-[(S)-1-benzyl-2-((R)-2-methyloxiranyl)-2-oxoethylcarbamoyl]-2-difluoromethoxyethylcarbamoyl}-2-difluoromethoxyethyl)amide;

Oxazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

5-Methyl-thiophene-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

5-Methyl-furan-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Thiophene-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N-[(1S)-2-[[(1S)-2-[[(1S)-1-benzyl-2-[(2R)-2-methyloxiran-2-yl]-2-oxo-ethyl]amino]-1-(difluoromethoxymethyl)-2-oxo-ethyl]amino]-1-(difluoromethoxymethyl)-2-oxo-ethyl]-1H-1,2,4-triazole-5-carboxamide;

N-[(1S)-1-(difluoromethoxymethyl)-2-[[(1S)-1-(difluoromethoxymethyl)-2-[[(1S)-3-methyl-1-[(2R)-2-methyloxirane-2-carbonyl]butyl]-amino]-2-oxo-ethyl]amino]-2-oxo-ethyl]-2-methyl-thiazole-5-carboxamide;

Pyridine-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N—((S)-1-{(S)-1-[(S)-1-Benzyl-2-((R)-2-methyl-oxiranyl)-2-oxo-ethylcarbamoyl]-2-difluoromethoxyethylcarbamoyl}-2-difluoromethoxyethyl)-nicotinamide;

Pyridine-2-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

N-[(1S)-2-[[(1S)-2-[[(1S)-1-benzyl-2-[(2R)-2-methyloxiran-2-yl]-2-oxo-ethyl]amino]-1-(difluoromethoxymethyl)-2-oxo-ethyl]amino]-1-(difluoromethoxymethyl)-2-oxo-ethyl]-pyrimidine-2-carboxamide;

[1,2,4]Triazine-3-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

Pyrimidine-4-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-2-difluoromethoxyethyl)-amide;

2-Methyl-thiazole-5-carboxylic acid ((S)-1-{(S)-1-[(S)-1-benzyl-2-((R)-2-methyloxiranyl)-2-oxo-ethylcarbamoyl]-3-methylbutylcarbamoyl}-2-difluoromethoxyethyl)-amide;

2-Methyl-thiazole-5-carboxylic acid ((S)-2-difluoromethoxy-1-{(S)-3-methyl-1-[(S)-3-methyl-1-((R)-2-methyloxiranecarbonyl)-butylcarbamoyl]-butylcarbamoyl}-ethyl)-amide, 2-Methyl-thiazole-5-carboxylic acid ((S)-1-{(S)-2-difluoromethoxy-1-[(S)-3-methyl-1-((R)-2-methyloxiranecarbonyl)-butylcarbamoyl]-ethylcarbamoyl}-3-methylbutyl)-amide;

2-Methyl-thiazole-5-carboxylic acid ((S)-1-{(S)-1-[(S)-1-benzyl-2-((R)-2-methyloxiranyl)-2-oxo-ethylcarbamoyl]-2-difluoromethoxyethylcarbamoyl}-3-methylbutyl)-amide;

2-Methyl-thiazole-5-carboxylic acid ((S)-1-{(S)-2-difluoromethoxy-1-[(S)-3-methyl-1-((R)-2-methyloxiranecarbonyl)-butylcarbamoyl]-ethylcarbamoyl}-2-phenylethyl)-amide;

2-Methyl-thiazole-5-carboxylic acid ((S)-1-{(S)-1-[(S)-1-benzyl-2-((R)-2-methyl-oxiranyl)-2-oxo-ethylcarbamoyl]-2-difluoromethoxyethylcarbamoyl}-2-phenylethyl)-amide;

2S)-2-[[(2S)-3-(difluoromethoxy)-2-[(2-morpholinoacetyl)amino]propanoyl]amino]-N-[(1S)-3-methyl-1-[(2R)-2-methyloxirane-2-carbonyl]butyl]-3-phenylpropanamide;

(S)—N—{(S)-1-[(S)-1-Benzyl-2-((R)-2-methyloxiranyl)-2-oxo-ethyl-carbamoyl]-2-difluoromethoxyethyl}-3-difluoromethoxy-2-(2-morpholin-4-yl-acetylamino)-propionamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-4-methylpentanamide;

(2S)-2-[[(2S)-3-(difluoromethoxy)-2-[(2-morpholinoacetyl)amino]propanoyl]amino]-4-methyl-N-[(1S)-3-methyl-1-[(2R)-2-methyloxirane-2-carbonyl]butyl]pentanamide;

(2S)—N-[(1S)-1-benzyl-2-[(2R)-2-methyloxiran-2-yl]-2-oxo-ethyl]-2-[[(2S)-3-(difluoromethoxy)-2-[(2-morpholinoacetyl)amino]propanoyl]amino]-3-(1-methylcyclohexa-1,3,5-trien-1-yl)propanamide;

(S)-4-Methyl-2-(2-morpholin-4-yl-acetylamino)-pentanoic acid {(S)-2-difluoromethoxy-1-[(S)-3-methyl-1-((R)-2-methyloxiranecarbonyl)-butylcarbamoyl]-ethyl}-amide;

(S)-4-Methyl-2-(2-morpholin-4-yl-acetylamino)-pentanoic acid {(S)-1-[(S)-1-benzyl-2-((R)-2-methyloxiranyl)-2-oxo-ethylcarbamoyl]-2-difluoromethoxyethyl}-amide;

(2S)—N-[(1S)-2-[[(1S)-1-benzyl-2-[(2R)-2-methyloxiran-2-yl]-2-oxo-ethyl]amino]-1(difluoromethoxymethyl)-2-oxo-ethyl]-2-[(2-morpholinoacetyl)amino]-3-phenylpropanamide; and (2S)-3-(difluoromethoxy)-N-[(1S)-1-(difluoromethoxymethyl)-2-[[(1S)-3-methyl-1-[(2R)-2-methyloxirane-2-carbonyl]butyl]amino]-2-oxo-ethyl]-2-[(2-morpholinoacetyl)amino]-propanamide.

8. The compound of claim 1, wherein the compound is:

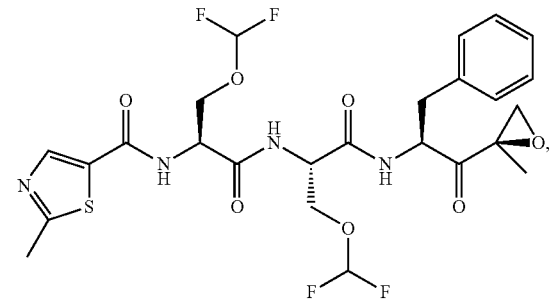 [SMILES: Cc1ncc(C(=O)N[C@@H](COC(F)F)C(=O)N[C@@H](COC(F)F)C(=O)N[C@@H](Cc2ccccc2)C(=O)[C@@]2(C)CO2)s1]

or a salt, thereof.

9. The compound of claim 1, wherein X and $R^1$ together form the structure:

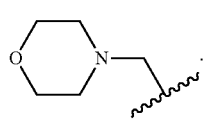

10. The compound of claim 1, wherein $R^1$ is

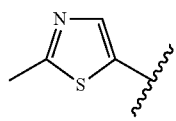 [SMILES: *c1cnc(C)s1]

and X is absent.

11. The compound of claim 1, wherein the compound is:

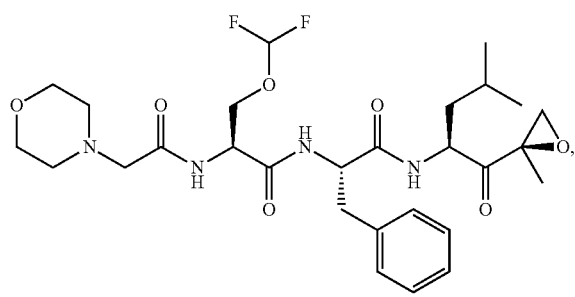 [SMILES: CC(C)C[C@H](NC(=O)[C@H](Cc1ccccc1)NC(=O)[C@H](COC(F)F)NC(=O)CN1CCOCC1)C(=O)[C@@]1(C)CO1]

or a salt thereof.

12. The compound of claim 1, wherein the compound is:

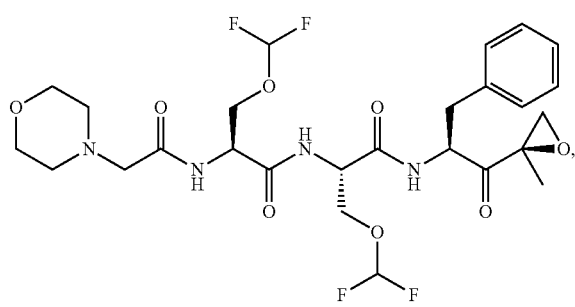 [SMILES: C[C@]1(C(=O)[C@H](Cc2ccccc2)NC(=O)[C@H](COC(F)F)NC(=O)[C@H](COC(F)F)NC(=O)CN2CCOCC2)CO1]

or a salt thereof.

13. The compound of claim 1, wherein the compound is:

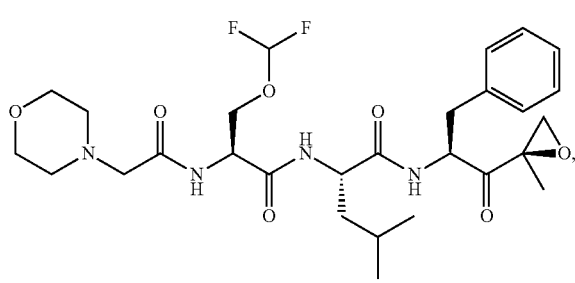 [SMILES: CC(C)C[C@H](NC(=O)[C@H](COC(F)F)NC(=O)CN1CCOCC1)C(=O)N[C@@H](Cc1ccccc1)C(=O)[C@@]1(C)CO1]

or a salt thereof.

14. The compound of claim 1, wherein the compound is:

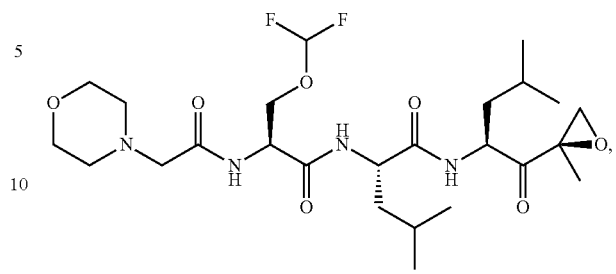

or a salt thereof.

15. The compound of claim 1, wherein the compound is:

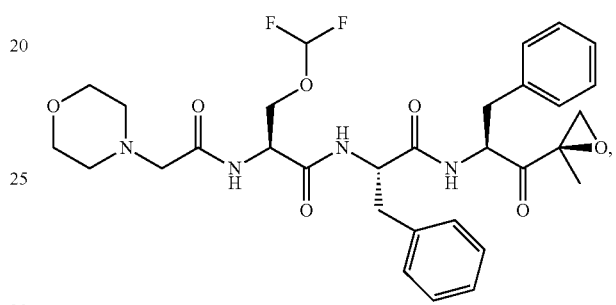

or a salt thereof.

16. The compound of claim 1, wherein the compound is:

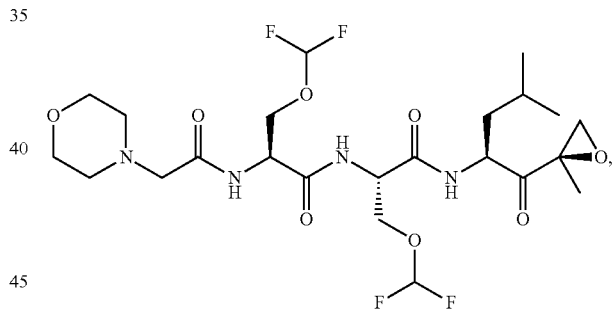

or a salt thereof.

17. A pharmaceutical composition comprising a compound of claim 8 and a pharmaceutically acceptable carrier.

18. The compound of claim 1, wherein the compound is:

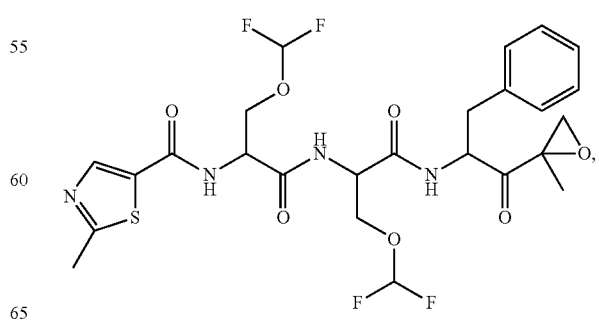

or a salt thereof.

19. A pharmaceutical composition comprising a compound of claim 18 and a pharmaceutically acceptable carrier.

20. A pharmaceutical composition comprising a compound of any one of claims 1, 2, 3, 4, 5 to 7 and 9 to 16 and a pharmaceutically acceptable carrier.

21. A method for inhibiting proteasome in a cell, comprising administering an effective amount of a compound according to claim 1 to the cell.

22. A method of treating a disease, disorder or condition that is mediated by proteasome inhibition, comprising administering a therapeutically effective amount of a compound according to any one of claims 1, 2, 3, 4, 5 to 7 and 9 to 16 to a subject in need thereof, wherein the disease, disorder or condition is selected from cancer and inflammatory disorders.

23. A method of inhibiting the degradation of a protein by a proteasome capable of degrading the protein, comprising contacting the proteasome with an effective amount of a compound according to claim 1.

24. A method of treating accelerated and/or enhanced proteolysis comprising administering a therapeutically effective amount of a compound according to claim 1 to a subject in need thereof.

25. The method of claim 22, wherein the cancer is selected from a cancer of the skin, blood, prostate, colorectum, pancreas, kidney, ovary, breast, liver, tongue and lung.

26. The method of claim 22, wherein the cancer is selected from leukaemia, lymphoma, non-Hodgkin's lymphoma and multiple myeloma.

27. A method of treating a disease, disorder or condition that is mediated by proteasome inhibition, comprising administering a therapeutically effective amount of a compound according to claim 8, wherein the disease, disorder or condition is selected from cancer and inflammatory disorders.

28. A method of treating a disease, disorder or condition that is mediated by proteasome inhibition, comprising administering a therapeutically effective amount of a compound according to claim 8, wherein the disease, disorder or condition is cancer.

29. A method of treating a disease, disorder or condition that is mediated by proteasome inhibition, comprising administering a therapeutically effective amount of a compound according to claim 18, wherein the disease, disorder or condition is selected from cancer and inflammatory diseases.

30. A method of treating a disease, disorder or condition that is mediated by proteasome inhibition, comprising administering a therapeutically effective amount of a compound according to claim 18, wherein the disease, disorder or condition is cancer.

* * * * *